(12) United States Patent
Atkinson et al.

(10) Patent No.: US 8,993,560 B2
(45) Date of Patent: Mar. 31, 2015

(54) COMPOUNDS

(75) Inventors: Francis Louis Atkinson, Stevenage (GB); Michael David Barker, Stevenage (GB); John Liddle, Stevenage (GB); David Matthew Wilson, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 237 days.

(21) Appl. No.: 13/414,873

(22) Filed: Mar. 8, 2012

(65) Prior Publication Data

US 2012/0232061 A1   Sep. 13, 2012

(30) Foreign Application Priority Data

Mar. 11, 2011   (GB) .................................. 1104153.0

(51) Int. Cl.
| | | |
|---|---|---|
| *A61K 31/55* | (2006.01) | |
| *C07D 401/12* | (2006.01) | |
| *C07D 403/12* | (2006.01) | |
| *A61K 31/4725* | (2006.01) | |
| *A61K 45/06* | (2006.01) | |
| *C07D 401/14* | (2006.01) | |

(52) U.S. Cl.
CPC ............ *C07D 401/12* (2013.01); *C07D 403/12* (2013.01); *A61K 31/55* (2013.01); *A61K 31/4725* (2013.01); *A61K 45/06* (2013.01); *C07D 401/14* (2013.01)
USPC ...................................... 514/217.01; 540/594

(58) Field of Classification Search
CPC .............................. A61K 31/55; C07D 401/12
USPC ...................................... 514/217.01; 540/594
See application file for complete search history.

(56) References Cited

U.S. PATENT DOCUMENTS

| | | | |
|---|---|---|---|
| 5,366,982 A | 11/1994 | Dereu et al. | |
| 5,426,196 A | 6/1995 | Fang | |
| 6,017,919 A | 1/2000 | Inaba et al. | |
| 6,432,963 B1 | 8/2002 | Hisamichi et al. | |
| 6,765,021 B2 | 7/2004 | Butera et al. | |
| 7,649,110 B2 | 1/2010 | Akerman et al. | |
| 7,687,526 B2 | 3/2010 | Brown et al. | |

| | | | |
|---|---|---|---|
| 2002/0065315 A1 | 5/2002 | Jensen et al. |
| 2003/0149061 A1 | 8/2003 | Nishihara et al. |
| 2003/0199511 A1 | 10/2003 | Li et al. |
| 2008/0255155 A1 | 10/2008 | Raeppel et al. |
| 2011/0263549 A1 | 10/2011 | Fiegen et al. |

FOREIGN PATENT DOCUMENTS

| | | |
|---|---|---|
| JP | 2005170939 | 6/2005 |
| WO | 9850029 A1 | 11/1998 |
| WO | 9850030 A1 | 11/1998 |
| WO | 9850031 A1 | 11/1998 |
| WO | 9918096 A1 | 4/1999 |
| WO | 9936422 A1 | 7/1999 |
| WO | 0046203 A1 | 8/2000 |
| WO | 0100197 A2 | 1/2001 |
| WO | 0176582 A1 | 10/2001 |
| WO | 03006628 A2 | 1/2003 |
| WO | 03050174 A1 | 6/2003 |
| WO | 2005086904 A2 | 9/2005 |
| WO | 2006084186 A2 | 8/2006 |
| WO | WO 2007/009681 A1 | 1/2007 |
| WO | 2007033002 A1 | 3/2007 |
| WO | WO 2008/058341 A1 | 5/2008 |
| WO | 2011057208 A2 | 5/2011 |

*Primary Examiner* — Brenda Coleman
(74) *Attorney, Agent, or Firm* — Duke M. Fitch; John Lemanowicz; William R. Majarian

(57) ABSTRACT

A compound of formula (I):

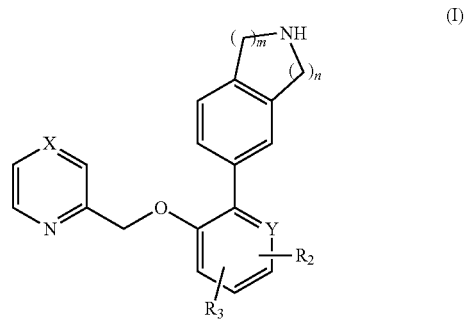

or a salt thereof;
which is an inhibitor of spleen tyrosine kinase (SYK) and therefore potentially of use in treating diseases resulting from inappropriate activation of mast cells, macrophages, and B-cells and related inflammatory responses and tissue damage, for instance inflammatory diseases and/or allergic conditions, in cancer therapy, specifically heme malignancies, and autoimmune conditions.

14 Claims, 6 Drawing Sheets

COMPOUNDS

CROSS-REFERENCE TO RELATED APPLICATIONS

This application claims the benefit of GB Application No. 1104153.0 filed on Mar. 11, 2011 in the United Kingdom.

FIELD OF THE INVENTION

The present invention relates to novel chemical compounds which have activity against spleen tyrosine kinase (Syk), processes for their preparation, pharmaceutically acceptable formulations containing them and their use in therapy.

BACKGROUND

Syk is a non-receptor tyrosine kinase that is involved in coupling activated immunoreceptors to signal downstream events that mediate diverse cellular responses, including proliferation, differentiation, and phagocytosis. Syk is widely expressed in hematopoietic cells. Syk inhibitors have potential anti-inflammatory and immunomodulating activities. They inhibit Syk-mediated IgG Fc epsilon and gamma receptor and BCR receptor signalling, resulting in inhibition of the activation of mast cells, macrophages, and B-cells and related inflammatory responses and tissue damage. Mast cells play a major role in type I hypersensitivity reactions and have been implicated in urticaria, bronchial asthma, anaphylaxis and other allergic conditions. Accordingly, Syk inhibitors have attracted interest in a number of therapeutic areas, including the treatment of rheumatoid arthritis, B-cell lymphoma, asthma, rhinitis and cutaneous disorders such as acute and chronic urticaria, mastocytosis, cutaneous lupus, atopic dermatitis, autoimmune bullous conditions including pemphigus and pemphigoid and other mast cell mediated diseases of the skin.

Acute and chronic urticaria are common skin diseases thought to affect around 25% of the total population within the USA. Although urticaria can be triggered by allergic reactions many cases have an unclear etiology. Chronic urticaria is defined as when wide spread wheals are present for greater than 6 weeks. There are many pathological similarities in chronic urticaria patients, in terms of extent of wheals in the skin, with allergen-induced mast and basophil cell degranulation reactions via IgE activation. Around 40% of chronic urticaria patients contain serum IgG auto-antibodies targeting IgE or the IgE receptor (Fc Epsilon Receptor) and these are thought to drive the histamine and other mediator release via mast and basophil degranulation. Syk inhibitors would inhibit the signalling response post IgE mediated Fc Epsilon activation and inhibit the mediator release known to be involved in chronic pruritis in multiple diseases.

Cutaneous mastocytosis is defined as an excessive accumulation of mast cells in the skin normally seen in both the paediatric and adult population. It is a rare disease thought to be due to a dysregulation in the proliferative capacity of the mast cells. The excessive production of mast cells in the skin leads to an increased release of cytokines and histamines which lead to itching, skin lesions, and in some cases where there is a systemic involvement, anaphylactic shock or low blood pressure.

Cutaneous lupus is a condition of the skin found in some patients with a discoid form of lupus erythematosus. The disorder is characterised by a red raised rash on the face or scalp and other areas of the body and mast cells and antibody deposition are known to be involved in the lesions.

A Syk inhibitor applied topically would decrease the production of cytokines, histamines and other mediators potentially leading to reduced itching and inflammatory infiltration in the skin.

Atopic dermatitis is a very common and sometimes long lasting inflammatory skin disorder characterised by redness and pruritis. The disease often occurs with other allergic conditions such as hay fever or asthma, is found predominantly in young children and is exacerbated by contact with allergens. Mast cell involvement is understood to lead to the characteristic itching and excessive scratching which can lead to an increase in bacterial infections in the skin. Topical application of a Syk inhibitor could reduce these symptoms.

Autoimmune bullous conditions including pemphigus and pemphigoid are acute and chronic skin diseases involving the formation of blisters. Bullous pemphigoid (BP) is a chronic, autoimmune, subepidermal, blistering skin disorder (unlike pemphigus where the blistering is intraepidermal). These rare diseases generally affect people over the age of 70. Autoantibodies are generated against the basement membrane layer of the skin leading to activation of complement and other inflammatory mediators. The inflammatory process initiates a release of enzymes which degrade proteins in the hemidesmosomal layers eventually leading to blisters as the layers of the skin fall apart. An urticarial rash and pruritis generally occur prior to onset of the blisters, so inhibition of mast cell degranulation and cytokine production post IgG antibody activation in macrophages with a Syk inhibitor could be beneficial in these diseases.

Rheumatoid arthritis (RA) is an autoimmune disease affecting approximately 1% of the population. It is characterised by inflammation of articular joints leading to debilitating destruction of bone and cartilage. Recent clinical studies with rituximab, which causes a reversible B cell depletion, (J. C. W. Edwards et al. 2004, New Eng. J. Med. 350: 2572-2581), have shown that targeting B cell function is an appropriate therapeutic strategy in autoimmune diseases such as RA. Clinical benefit correlates with a reduction in auto-reactive antibodies (or rheumatoid F factor) and these studies suggest that B cell function and indeed auto-antibody production are central to the ongoing pathology in the disease Studies using cells from mice deficient in Syk have demonstrated a non-redundant role of this kinase in B cell function. The deficiency in Syk is characterised by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely to block B cell function and hence reduce rheumatoid factor production. In addition to the role of Syk in B cell function, of relevance to the treatment of RA, is the requirement for Syk activity in Fc receptor (FcR) signalling. FcR activation by immune complexes in RA has been suggested to contribute to the release of multiple pro-inflammatory mediators.

The contribution of Syk dependent processes to the pathology of RA has been reviewed by Wong et al (2004, ibid).

The results of a 12 week proof of concept clinical trial for the Syk inhibitor R788 (fostamatinib disodium, Rigel) have been published: Treatment of rheumatoid arthritis with a Syk inhibitor: A twelve-week, randomized, placebo-controlled trial, Arthritis & Rheumatis, 58(11), 2008, 3309-3318.

Syk inhibitors may also be useful in cancer therapy, specifically heme malignancies, particularly Non-Hodgkin's Lymphomas including follicular (FL), mantle cell, Burkitt and diffuse large B cell (DLBCL) lymphomas.

Studies have shown that Syk is dysregulated by overexpression and/or constitutively activation in a variety of primary B-lymphoma tumours and also in B-lymphoma cell lines. Syk, through the PI3K/AKT pathway, the PLD pathway and AKT independent signalling, activates mTOR (mammalian target of rapamycin) which in turn increases B-cell survival and proliferation. Inhibition of Syk in vitro, results in decreased mTOR activation and a reduction of clonicity in FL cells. Inhibition of Syk with curcumin in a murine model of B lymphoma (BKS-2) gave a significant reduction of tumour burden as measured by the total splenocyte number. (Leseux L. et al. Blood 15 Dec. 2006, Vol 108, No 13 pp 4156-4162 and Gururajan M. et al. Journal of Immunology, 2007, 178 pp 111-121).

Results of a Phase 2 clinical trial of R788 (fostamatinib disodium) in patients with relapsed or refractory B-Cell non-Hodgkin's lymphoma (NHL) show that the compound is well-tolerated by these patients, as well as a therapeutic benefit in patients suffering from diffuse large B-Cell lymphoma (DLBCL) and chronic lymphocytic leukemia/small lymphocytic lymphoma (CLL/SLL). Despite the fact that the patients enrolled in this trial had advanced disease and had failed treatment with marketed therapies, a significant number of them were particularly responsive to Syk inhibition with R788 (Chen et al. Blood 2008 Vol 111 pp 2230-2237, www.Rigel.com)

Syk inhibitors may also be useful in the treatment of asthma and allergic rhinitis as they are important in transducing the downstream cellular signals associated with cross-linking FcεR1 and or FcγR1 receptors, and Syk is positioned early in the signalling cascade. In mast cells, for example, the early sequence of FcεR1 signalling following allergen cross-linking of receptor-IgE complexes involves first Lyn (a Src family tyrosine kinase) and then Syk.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE (FcεRI) and IgG (FcγRI) become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesised lipid mediators including prostaglandins and leukotrienes.

The Syk inhibitor R112 (Rigel), dosed intranasally in a phase I/II study for the treatment of allergic rhinitis, was shown to give a statistically significant decrease in PGD$_2$, a key immune mediator that is highly correlated with improvements in allergic rhinorrhea, as well as being safe across a range of indicators, thus providing the first evidence for the clinical safety and efficacy of a topical Syk inhibitor (see Meltzer, Eli O.; Berkowitz, Robert B.; Grossbard, Elliott B. An intranasal Syk inhibitor (R112) improves the symptoms of seasonal allergic rhinitis in a park environment. Journal of Allergy and Clinical Immunology (2005), 115(4), 791-796). In a further phase II clinical trial, for allergic rhinitis, R112 was however shown as having a lack of efficacy versus placebo (Clinical Trials.gov Identifier NCT0015089).

WO 03/057695 (Boehringer Ingelheim Pharmaceuticals, Inc) describes 1,6 Naphthyridines that have Syk inhibitory activity. These are further described in "Discovery and SAR of Novel [1,6] Naphthyridines as Potent Inhibitors of Spleen Tyrosine Kinase (SYK) (Bioorganic & Medicinal Chemistry Letters 13 (2003) 1415-1418). This has been followed with two more recent patent applications, WO 2010/015518 and WO 2010/015529 (Boehringer Ingelheim Pharmaceuticals, Inc), describing 4-dimethylamino-phenyl-substituted naphthyridines and substituted naphthyridines, respectively.

WO 04/035604 discloses the structural co-ordinates of the human Syk protein.

There remains however the need to identify further compounds which are inhibitors of Syk.

BRIEF SUMMARY OF THE INVENTION

The present invention relates to novel chemical compounds which have activity against spleen tyrosine kinase (Syk), processes for their preparation, pharmaceutically acceptable formulations containing them and their use in therapy.

DETAILED DESCRIPTION OF THE INVENTION

Figure 1:
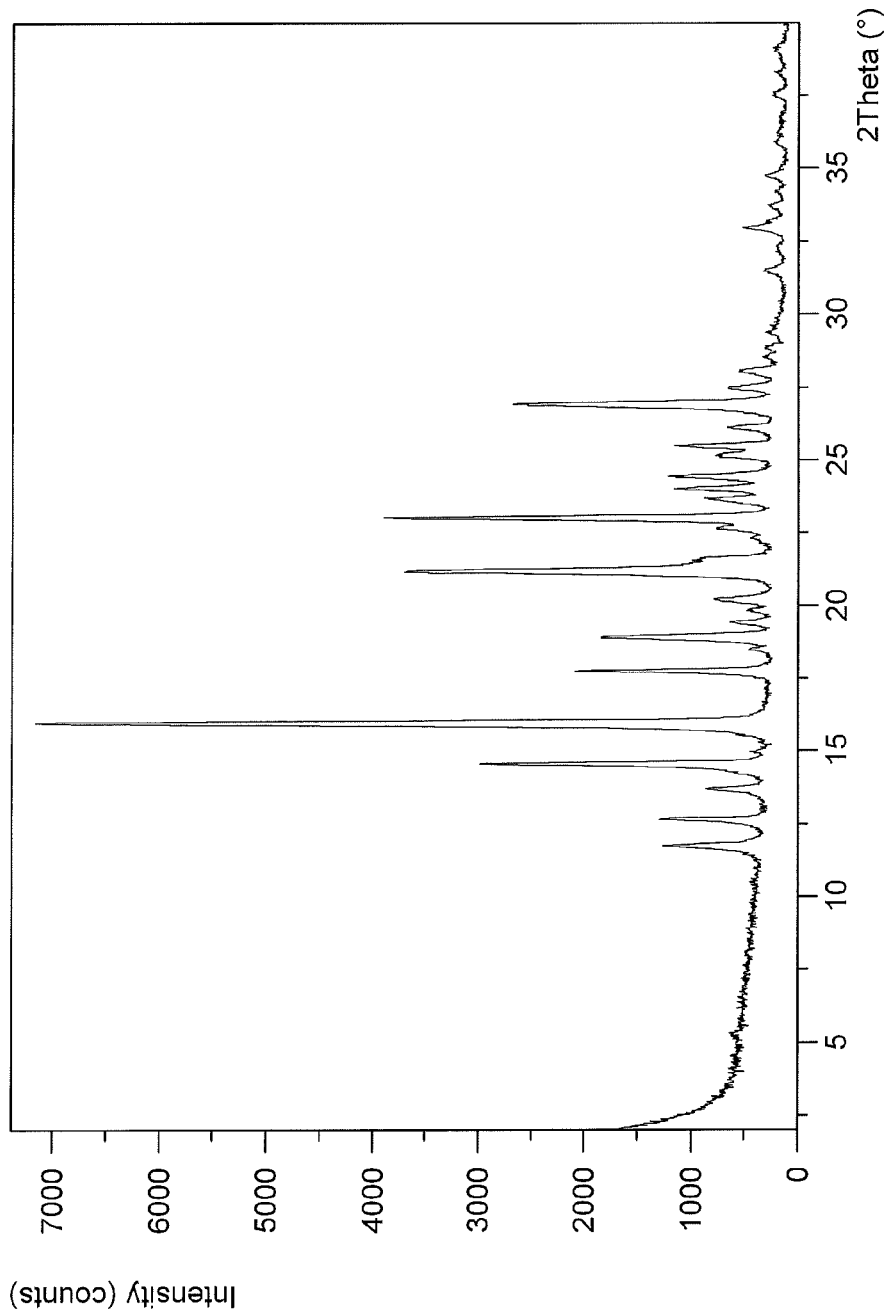
FIG. 1 shows the XRPD diffraction pattern for FORM 1.

Thus, in one embodiment, the present invention provides a compound of formula (I):

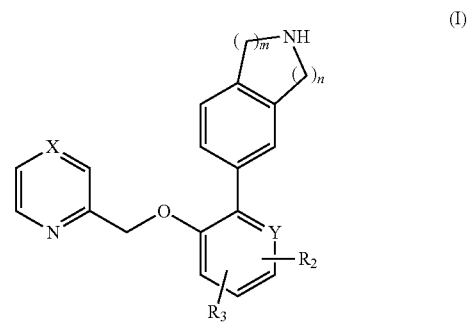

wherein:

X is CR$_1$ or N;

Y is CH, C or N;

R$_1$ is hydrogen, C$_{1-6}$alkoxy or C$_{1-6}$alkyl;

R$_2$ is hydrogen, C$_{1-6}$alkoxy, halo, —C(O)C$_{1-6}$alkyl, CN, Halo-C$_{1-6}$alkyl or C(O)NR$_4$R$_5$;

R$_3$ is hydrogen or C$_{1-6}$alkoxy;

R$_4$ is hydrogen or C$_{1-6}$alkyl:

R$_5$ is hydrogen or C$_{1-6}$alkyl and m and n are integers each independently selected from 1 and 2; or a salt thereof.

In one embodiment, the invention provides a compound of formula (Ia);

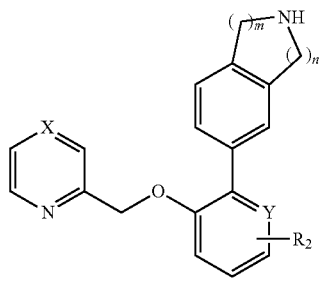

(Ia)

wherein:
X is CR$_1$ or N;
Y is CH, C or N;
R$_1$ is hydrogen, C$_{1-6}$alkoxy or C$_{1-6}$alkyl;
R$_2$ is hydrogen, C$_{1-6}$alkoxy, halo or —C(O)C$_{1-6}$alkyl; and
m and n are integers each independently selected from 1 and 2; or
a salt thereof.

In one embodiment X is CR$_1$ or N. In another embodiment X is CR$_1$.

In one embodiment Y is CH, C or N. In another embodiment Y is CH. In another embodiment Y is C. In a further embodiment Y is N.

In one embodiment R$_1$ is hydrogen, C$_{1-6}$alkoxy or C$_{1-6}$alkyl. In another embodiment R$_1$ is methyl, methoxy or hydrogen.

In one embodiment R$_2$ is hydrogen, C$_{1-6}$alkoxy, halo, —C(O)C$_{1-6}$alkyl, CN, Halo-C$_{1-6}$-alkyl or C(O)NR$_4$R$_5$. In one embodiment R$_2$ is hydrogen, C$_{1-6}$alkoxy, halo or —C(O) C$_{1-6}$alkyl. In another embodiment R$_2$ is hydrogen, methoxy, fluoro, —C(O)CH$_3$ or trifluoromethyl. In another embodiment R$_2$ is hydrogen, methoxy, fluoro or —C(O)CH$_3$. In a further embodiment R$_2$ is hydrogen, methoxy or —C(O)CH$_3$.

In one embodiment R$_3$ is hydrogen or C$_{1-6}$alkoxy. In one embodiment R$_3$ is hydrogen, or methoxy.

In one embodiment R$_4$ is hydrogen or C$_{1-6}$alkyl. In another embodiment R$_4$ is hydrogen or C$_{1-4}$alkyl. In a further embodiment R$_4$ is hydrogen or methyl.

In one embodiment R$_5$ is hydrogen or C$_{1-6}$alkyl. In another embodiment R$_5$ is hydrogen or C$_{1-4}$alkyl. In a further embodiment R$_5$ is hydrogen or methyl.

In one embodiment m and n are integers each independently selected from 1 and 2. In another embodiment m is 2 and n is 1 or 2. In another embodiment n is 1 and m is 1 or 2. In a further embodiment m and n are both 2.

In one embodiment X is CR$_1$, and R$_1$ is methyl. In another embodiment, X is CR$_1$, R$_1$ is methyl and Y is C. In a further embodiment, X is CR$_1$, R$_1$ is methyl, Y is C and R$_2$— is methoxy. In a yet further embodiment, X is CR$_1$, R$_1$ is methyl, Y is C, R$_2$ is methoxy and R$_3$ is hydrogen. In a still further embodiment, X is CR$_1$, R$_1$ is methyl, Y is C, R$_2$ is methoxy, R$_3$ is hydrogen, m is 2 and n is 2.

In one embodiment, the compound of formula (I) is selected from:
7-(3-{[(4-methyl-2-pyridinyl)methyl]oxy}-2-pyridinyl)-2,3,4,5-tetrahydro-1H-3-benzazepine;
7-(2-(methyloxy)-6-{[(4-methyl-2-pyridinyl)methyl]oxy}phenyl)-2,3,4,5-tetrahydro-1H-3-benzazepine;
7-(4-(methyloxy)-2-{[(4-methyl-2-pyridinyl)methyl]oxy}phenyl)-2,3,4,5-tetrahydro-1H-3-benzazepine;
1-[4-{[(4-methyl-2-pyridinyl)methyl]oxy}-3-(2,3,4,5-tetrahydro-1H-3-benzazepin-7-yl)phenyl]ethanone;
7-(6-methyl-3-{[(4-methyl-2-pyridinyl)methyl]oxy}-2-pyridinyl)-2,3,4,5-tetrahydro-1H-3-benzazepine;
1-[4-[(2-pyrazinylmethyl)oxy]-3-(2,3,4,5-tetrahydro-1H-3-benzazepin-7-yl)phenyl]ethanone;
7-(5-fluoro-2-{[(4-methyl-2-pyridinyl)methyl]oxy}phenyl)-1,2,3,4-tetrahydroisoquinoline;
7-(5-methyl-2-{[(4-methyl-2-pyridinyl)methyl]oxy}phenyl)-1,2,3,4-tetrahydroisoquinoline;
7-(2-(methyloxy)-6-{[(4-methyl-2-pyridinyl)methyl]oxy}phenyl)-1,2,3,4-tetrahydroisoquinoline;
7-(5-(ethyloxy)-2-{[(4-methyl-2-pyridinyl)methyl]oxy}phenyl)-1,2,3,4-tetrahydroisoquinoline;
7-(4-(methyloxy)-2-{[(4-methyl-2-pyridinyl)methyl]oxy}phenyl)-1,2,3,4-tetrahydroisoquinoline;
4-{[(4-methyl-2-pyridinyl)methyl]oxy}-3-(1,2,3,4-tetrahydro-7-isoquinolinyl)benzonitrile;
7-[2-{[(4-methyl-2-pyridinyl)methyl]oxy}-5-(trifluoromethyl)phenyl]-1,2,3,4-tetrahydroisoquinoline;
7-(5-(methyloxy)-2-{[(4-methyl-2-pyridinyl)methyl]oxy}phenyl)-1,2,3,4-tetrahydroisoquinoline;
7-(5-(1,1-dimethylethyl)-2-{[(4-methyl-2-pyridinyl)methyl]oxy}phenyl)-1,2,3,4-tetrahydroisoquinoline;
N-methyl-4-{[(4-methyl-2-pyridinyl)methyl]oxy}-3-(2,3,4,5-tetrahydro-1H-3-benzazepin-7-yl)benzamide;
4-{[(4-methyl-2-pyridinyl)methyl]oxy}-3-(2,3,4,5-tetrahydro-1H-3-benzazepin-7-yl)benzamide;
N,N-dimethyl-4-{[(4-methyl-2-pyridinyl)methyl]oxy}-3-(1,2,3,4-tetrahydro-7-isoquinolinyl)benzamide;
4-{[(4-methyl-2-pyridinyl)methyl]oxy}-3-(1,2,3,4-tetrahydro-7-isoquinolinyl)benzamide;
7-(2,3-bis(methyloxy)-6-{[(4-methyl-2-pyridinyl)methyl]oxy}phenyl)-1,2,3,4-tetrahydroisoquinoline;
7-(2,3-bis(methyloxy)-6-{[(4-methyl-2-pyridinyl)methyl]oxy}phenyl)-2,3,4,5-tetrahydro-1H-3-benzazepine;
7-[2-({[4-(methyloxy)-2-pyridinyl]methyl}oxy)phenyl]-2,3,4,5-tetrahydro-1H-3-benzazepine;
1-[4-[(2-pyridinylmethyl)oxy]-3-(2,3,4,5-tetrahydro-1H-3-benzazepin-7-yl)phenyl]ethanone, trifluoroacetate;
7-{6-methyl-3-[(2-pyrazinylmethyl)oxy]-2-pyridinyl}-2,3,4,5-tetrahydro-1H-3-benzazepine, trifluoroacetate;
7-(6-methyl-3-{[(4-methyl-2-pyridinyl)methyl]oxy}-2-pyridinyl)-2,3,4,5-tetrahydro-1H-3-benzazepine, trifluoroacetate;
7-{5-(methyloxy)-2-[(2-pyrazinylmethyl)oxy]phenyl}-2,3,4,5-tetrahydro-1H-3-benzazepine, trifluoroacetate;
7-[5-(methyloxy)-2-({[4-(methyloxy)-2-pyridinyl]methyl}oxy)phenyl]-2,3,4,5-tetrahydro-1H-3-benzazepine;
7-(5-(methyloxy)-2-{[(4-methyl-2-pyridinyl)methyl]oxy}phenyl)-2,3,4,5-tetrahydro-1H-3-benzazepine, trifluoroacetate;
1-[4-({[4-(methyloxy)-2-pyridinyl]methyl}oxy)-3-(2,3,4,5-tetrahydro-1H-3-benzazepin-7-yl)phenyl]ethanone;
1-[4-{[(4-methyl-2-pyridinyl)methyl]oxy}-3-(2,3,4,5-tetrahydro-1H-3-benzazepin-7-yl)phenyl]ethanone, trifluoroacetate;
7-[2-({[4-(methyloxy)-2-pyridinyl]methyl}oxy)phenyl]-2,3,4,5-tetrahydro-1H-3-benzazepine, trifluoroacetate;
1,1-dimethylethyl 7-[6-methyl-3-({[4-(methyloxy)-2-pyridinyl]methyl}oxy)-2-pyridinyl]-1,2,4,5-tetrahydro-3H-3-benzazepine-3-carboxylate;
7-(5-fluoro-2-{[(4-methyl-2-pyridinyl)methyl]oxy}phenyl)-2,3,4,5-tetrahydro-1H-3-benzazepine;
7-(5-methyl-2-{[(4-methyl-2-pyridinyl)methyl]oxy}phenyl)-2,3,4,5-tetrahydro-1H-3-benzazepine;

7-(5-(ethyloxy)-2-{[(4-methyl-2-pyridinyl)methyl]
oxy}phenyl)-2,3,4,5-tetrahydro-1H-3-benzazepine;
7-(5-(methyloxy)-2-{[(4-methyl-2-pyridinyl)methyl]
oxy}phenyl)-2,3,4,5-tetrahydro-1H-3-benzazepine;
4-{[(4-methyl-2-pyridinyl)methyl]oxy}-3-(2,3,4,5-tetrahydro-1H-3-benzazepin-7-yl)benzonitrile;
7-[2-{[(4-methyl-2-pyridinyl)methyl]oxy}-5-(trifluoromethyl)phenyl]-2,3,4,5-tetrahydro-1H-3-benzazepine;
7-(5-(1,1-dimethylethyl)-2-{[(4-methyl-2-pyridinyl)methyl]
oxy}phenyl)-2,3,4,5-tetrahydro-1H-3-benzazepine;
7-(5-chloro-2-{[(4-methyl-2-pyridinyl)methyl]
oxy}phenyl)-2,3,4,5-tetrahydro-1H-3-benzazepine;
7-(3-{[(4-ethyl-2-pyridinyl)methyl]oxy}-6-methyl-2-pyridinyl)-2,3,4,5-tetrahydro-1H-3-benzazepine;
7-(6-(1,1-dimethylethyl)-3-{[(4-methyl-2-pyridinyl)methyl]
oxy}-2-pyridinyl)-2,3,4,5-tetrahydro-1H-3-benzazepine;
1-[4-{[(4-ethyl-2-pyridinyl)methyl]oxy}-3-(2,3,4,5-tetrahydro-1H-3-benzazepin-7-yl)phenyl]ethanone;
1-[4-({[4-(ethyloxy)-2-pyridinyl]methyl}oxy)-3-(2,3,4,5-tetrahydro-1H-3-benzazepin-7-yl)phenyl]ethanone;
1-[4-{[(4-{[2-(methyloxy)ethyl]oxy}-2-pyridinyl)methyl]
oxy}-3-(2,3,4,5-tetrahydro-1H-3-benzazepin-7-yl)phenyl]ethanone;
7-{5-(methyloxy)-2-[(2-pyridinylmethyl)oxy]phenyl}-2,3,4,5-tetrahydro-1H-3-benzazepine;
1-[4-[(2-pyridinylmethyl)oxy]-3-(1,2,3,4-tetrahydro-7-isoquinolinyl)phenyl]ethanone;
7-{5-chloro-2-[(2-pyridinylmethyl)oxy]phenyl}-1,2,3,4-tetrahydroisoquinoline;
7-(6-chloro-3-{[(4-methyl-2-pyridinyl)methyl]oxy}-2-pyridinyl)-2,3,4,5-tetrahydro-1H-3-benzazepine;
7-(6-chloro-3-{[(4-methyl-2-pyridinyl)methyl]oxy}-2-pyridinyl)-1,2,3,4-tetrahydroisoquinoline;
1,1-dimethylethyl 5-{5-acetyl-2-[(2-pyridinylmethyl)oxy]
phenyl}-1,3-dihydro-2H-isoindole-2-carboxylate;
1-[4-[(2-pyridinylmethyl)oxy]-3-(1,2,3,4-tetrahydro-6-isoquinolinyl)phenyl]ethanone; and
7-{2-(methyloxy)-6-[(2-pyrazinylmethyl)oxy]phenyl}-2,3,4,5-tetrahydro-1H-3-benzazepine, hydrochloride; or a salt thereof.

In one embodiment, the compound of formula (I) is selected from:
7-(3-{[(4-methyl-2-pyridinyl)methyl]oxy}-2-pyridinyl)-2,3,4,5-tetrahydro-1H-3-benzazepine;
7-(2-(methyloxy)-6-{[(4-methyl-2-pyridinyl)methyl]
oxy}phenyl)-2,3,4,5-tetrahydro-1H-3-benzazepine;
7-(4-(methyloxy)-2-{[(4-methyl-2-pyridinyl)methyl]
oxy}phenyl)-2,3,4,5-tetrahydro-1H-3-benzazepine;
1-[4-{[(4-methyl-2-pyridinyl)methyl]oxy}-3-(2,3,4,5-tetrahydro-1H-3-benzazepin-7-yl)phenyl]ethanone;
1-[4-[(2-pyrazinylmethyl)oxy]-3-(2,3,4,5-tetrahydro-1H-3-benzazepin-7-yl)phenyl]ethanone;
7-(5-fluoro-2-{[(4-methyl-2-pyridinyl)methyl]oxy}phenyl)-1,2,3,4-tetrahydroisoquinoline;
7-[2-({[4-(methyloxy)-2-pyridinyl]methyl}oxy)phenyl]-2,3,4,5-tetrahydro-1H-3-benzazepine; and
1-[4-[(2-pyridinylmethyl)oxy]-3-(2,3,4,5-tetrahydro-1H-3-benzazepin-7-yl)phenyl]ethanone; or a salt thereof.

In one embodiment the compound of formula (I) is:
7-(3-{[(4-methyl-2-pyridinyl)methyl]oxy}-2-pyridinyl)-2,3,4,5-tetrahydro-1H-3-benzazepine;
or a salt thereof.

In another embodiment the compound of formula (I) is:
7-(2-(methyloxy)-6-{[(4-methyl-2-pyridinyl)methyl]
oxy}phenyl)-2,3,4,5-tetrahydro-1H-3-benzazepine;
or a salt thereof.

In another embodiment the compound of formula (I) is:
7-(4-(methyloxy)-2-{[(4-methyl-2-pyridinyl)methyl]
oxy}phenyl)-2,3,4,5-tetrahydro-1H-3-benzazepine;
or a salt thereof.

In a further embodiment the compound of formula (I) is:
1-[4-{[(4-methyl-2-pyridinyl)methyl]oxy}-3-(2,3,4,5-tetrahydro-1H-3-benzazepin-7-yl)phenyl]ethanone;
or a salt thereof.

It will be appreciated in the following that the phrase "a compound of formula (I)" is intended to include a compound of formula (Ia).

It will be appreciated that compounds of formula (I) and salts thereof may exist in solvated forms. In another embodiment, the present invention provides compounds of formula (I) and salts thereof. In another embodiment, the present invention provides compounds of formula (I) and pharmaceutically acceptable salts thereof. In another embodiment, the present invention provides compounds of formula (I) and solvates thereof. In a further embodiment, the present invention provides compounds of formula (I) as the free base.

Compounds of the present invention are useful as inhibitors of Syk.

As used herein, the term "alkyl" refers to a straight or branched saturated hydrocarbon chain containing the specified number of carbon atoms. For example, $C_{1-6}$alkyl means a straight or branched alkyl group containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched saturated alkoxy chain containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "halo" or, alternatively, "halogen" refers to fluoro, chloro or bromo.

As used herein, the term "haloalkyl" refers to a straight or branched saturated hydrocarbon chain containing the specified number of carbon atoms, substituted with halo atoms. For example, Halo-$C_{1-6}$alkyl means a straight or branched alkyl group containing at least 1, and at most 6, carbon atoms, substituted with 1 to 3 halo atoms per carbon atom. Examples of "haloalkyl" as used herein include, but are not limited to, fluoromethyl, di-fluoromethyl, and tri-fluoromethyl.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problems or complications, commensurate with a reasonable benefit/risk ratio. The skilled artisan will appreciate that pharmaceutically acceptable salts of the compound of Formula (I) may be prepared.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. Indeed, in certain embodiments of the invention, pharmaceutically acceptable salts may be preferred over the respective free base or free acid because such salts impart greater stability or solubility to the molecule thereby facilitating formulation into a dosage form.

The compounds of formula (I) are basic and accordingly generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate),napthalene-2-sulfonate, Ethanedisulfonate, and 2,5-dihydroxybenzoate. In one embodiment, the present invention provides a pharmaceutically acceptable salt of a compound of formula (I) which is the hydrochloride salt, mesylate, fumarate or phosphate. In one embodiment, the present invention provides a pharmaceutically acceptable salt of a compound of formula (I) which is the mesylate.

A compound of formula (I) may exist in solid or liquid form. In the solid state, the compound of formula (I) may exist in crystalline or non-crystalline (amorphous) form, or as a mixture thereof. For a compound of formula (I) that is in crystalline form, the skilled artisan will appreciate that solvates, such as pharmaceutically acceptable solvates, may be formed wherein solvent molecules are incorporated into the crystalline lattice during crystallization. Solvates may involve non-aqueous solvents such as, but not limited to, ethanol, isopropanol, n-butanol, i-butanol, acetone, tetrahydrofuran, dioxane, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates". Hydrates include stoichiometric hydrates as well as compositions containing variable amounts of water.

The skilled artisan will further appreciate that a compound of formula (I) that exists in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

In a further aspect, the present invention provides a crystalline form of 7-(2-(methyloxy)-6-{[(4-methyl-2-pyridinyl) methyl]oxy}phenyl)-2,3,4,5-tetrahydro-1H-3-benzazepine (FORM 1) characterised by substantially the same X-ray powder diffraction (XRPD)pattern as shown in FIG. 1, wherein the XRPD pattern is expressed in terms of 2 theta angles and obtained with a diffractometer using copper Kα-radiation using procedures described herein. The XRPD of FORM 1 shows characteristic 2 theta angle peaks at 11.7, 12.7, 13.7 and 16.0.

Figure 2:
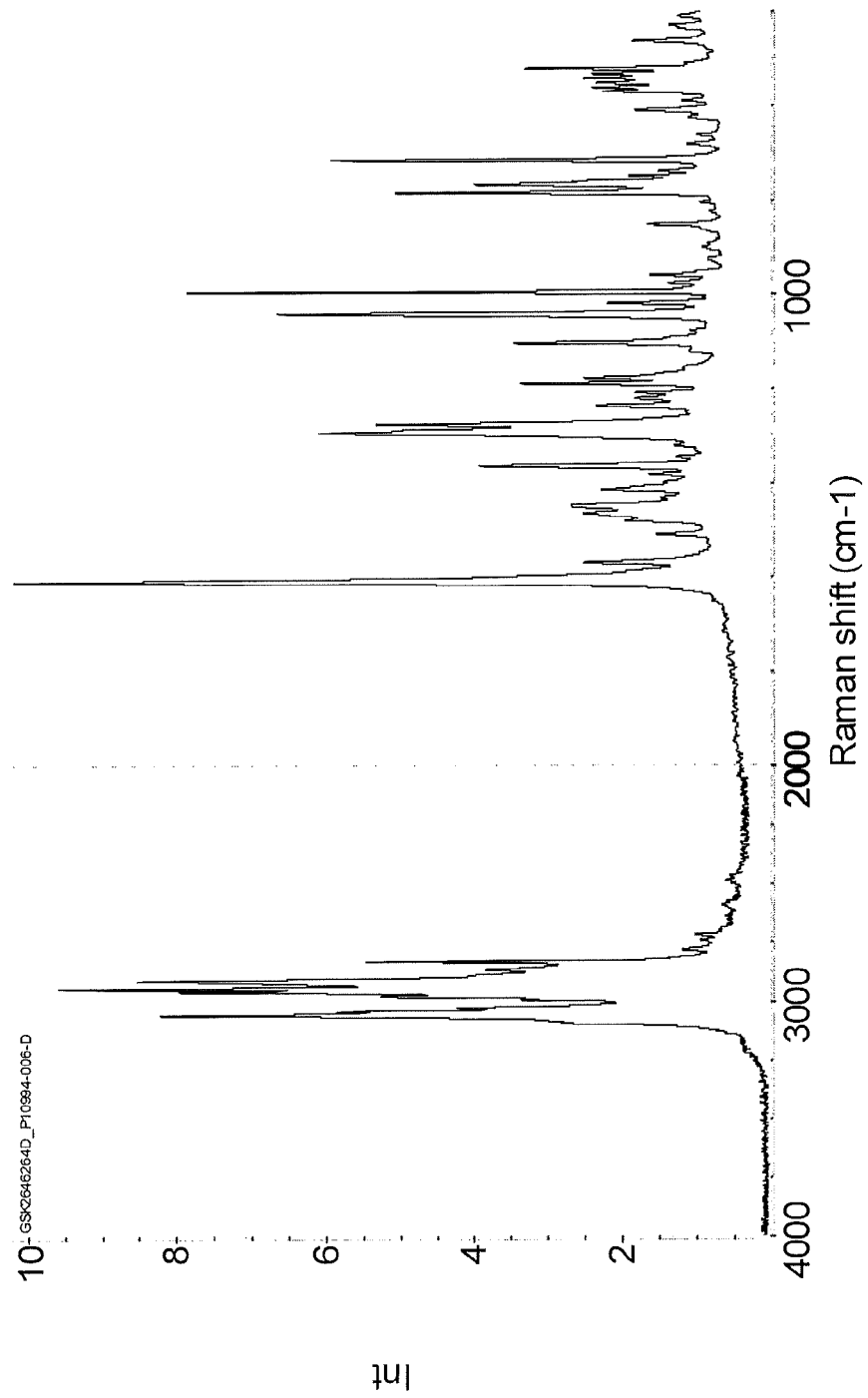
FIG. 2 shows the FT-Raman Spectrum for FORM 1.

Alternatively or additionally, FORM 1 of 7-(2-(methyloxy)-6-{[(4-methyl-2-pyridinyl)methyl]oxy}phenyl)-2,3,4, 5-tetrahydro-1H-3-benzazepine can be characterised by Raman spectroscopy as shown in FIG. 2, wherein the spectrum is expressed in terms of $cm^{-1}$ and obtained using procedures as herein described. The Raman spectrum of FORM 1 has characteristic peaks at 2945, 2832, 1610, 1363, 994 and 784.

Figure 3:
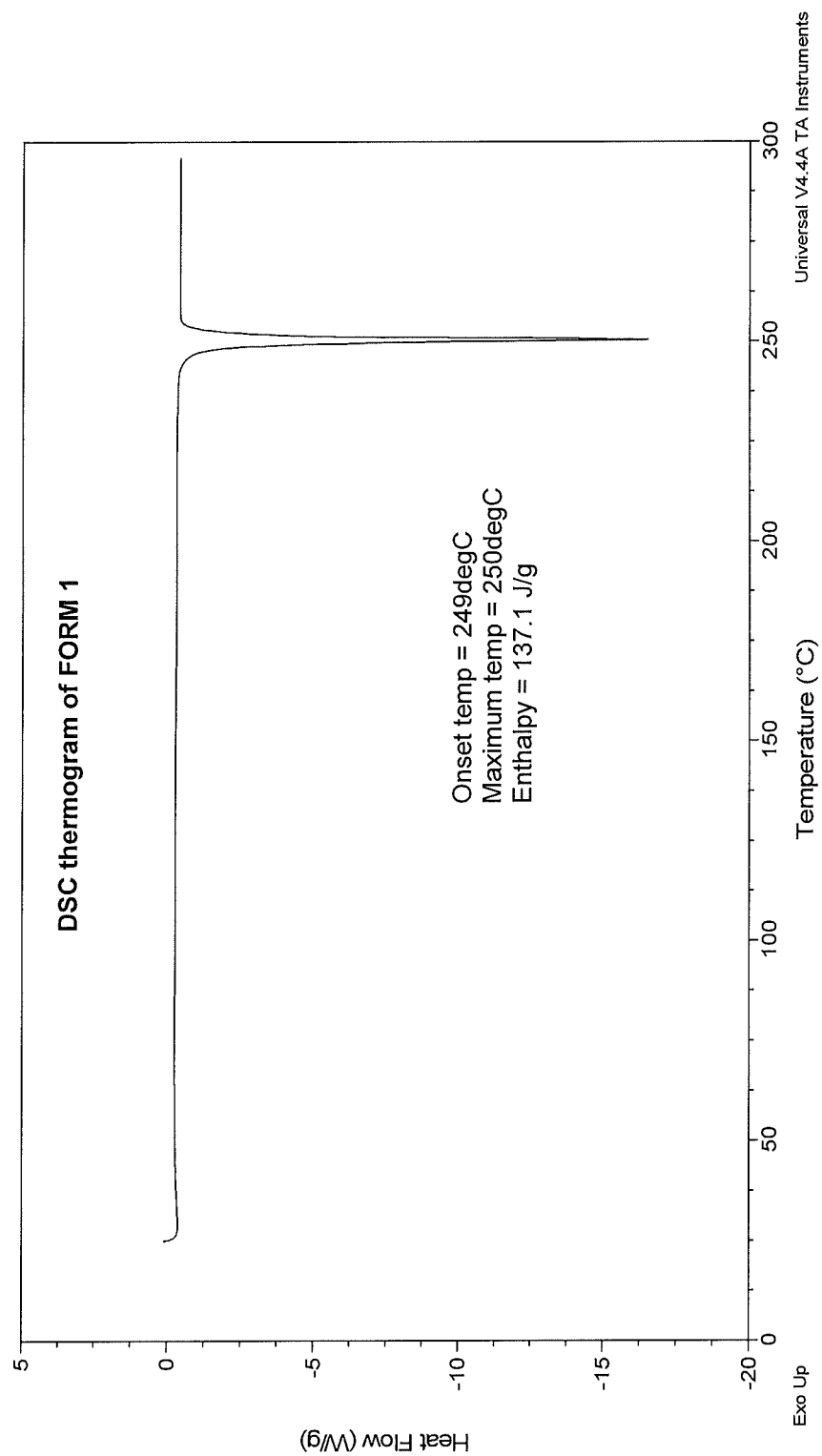
FIG. 3 shows the DSC thermogram of FORM 1.

Alternatively or additionally, FORM 1 of 7-(2-(methyloxy)-6-{[(4-methyl-2-pyridinyl)methyl]oxy}phenyl)-2,3,4, 5-tetrahydro-1H-3-benzazepine can be characterised by differential scanning calorimitry (DSC) thermograms as shown in FIG. 3, wherein the DSC was performed using procedures as herein described.

Figure 4:
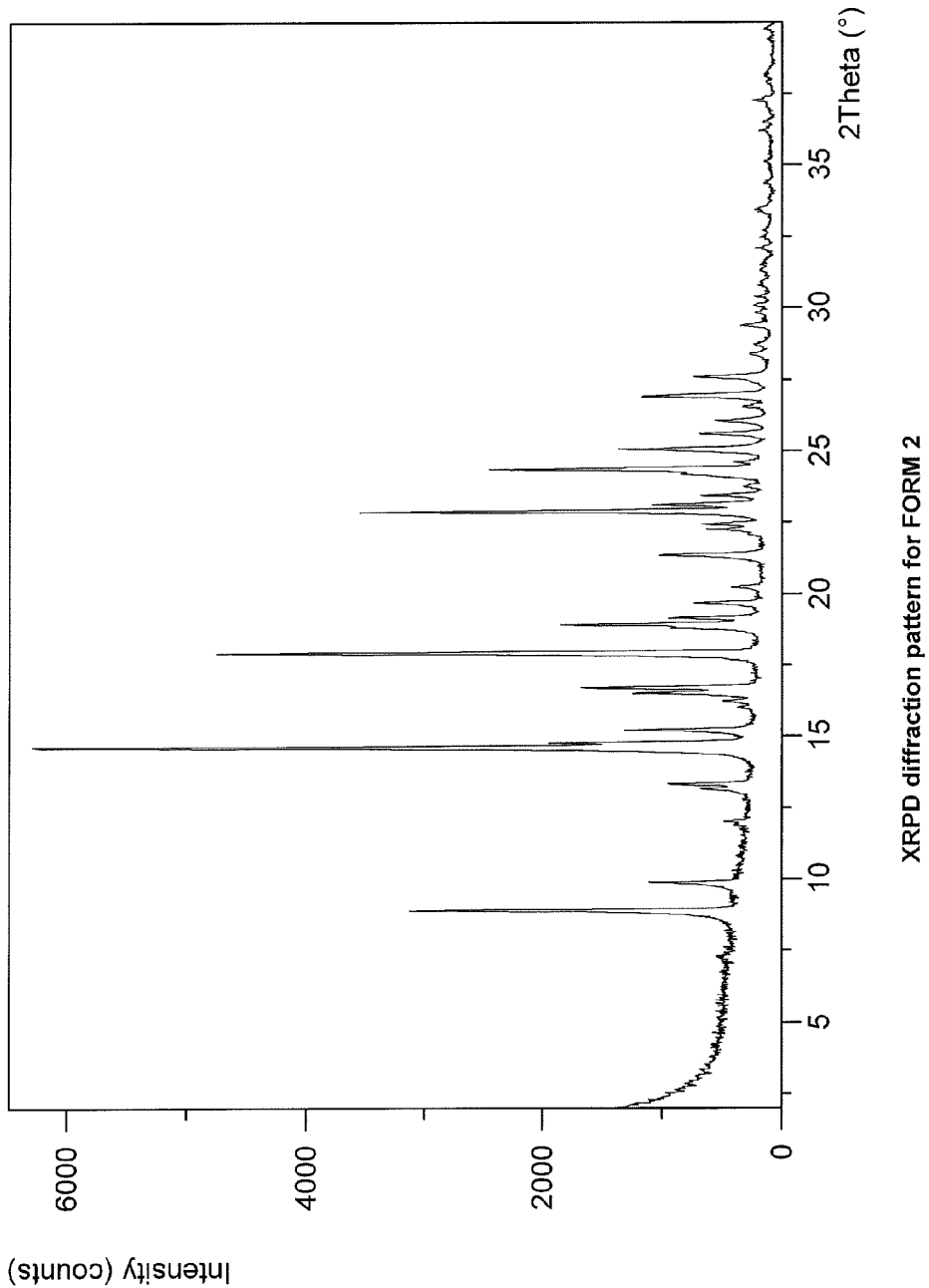
FIG. 4 shows the XRPD diffraction pattern for FORM 2.

In a further aspect, the present invention provides a crystalline form of 7-(2-(methyloxy)-6-{[(4-methyl-2-pyridinyl) methyl]oxy}phenyl)-2,3,4,5-tetrahydro-1H-3-benzazepine (FORM 2) characterised by substantially the same X-ray powder diffraction (XRPD) pattern as shown in FIG. 4, wherein the XRPD pattern is expressed in terms of 2 theta angles and obtained with a diffractometer using copper Kα-radiation using procedures described herein. The XRPD of FORM 1 shows characteristic 2 theta angle peaks at 8.9, 9.9, 13.3, 15.2, 16.7.

Figure 5:
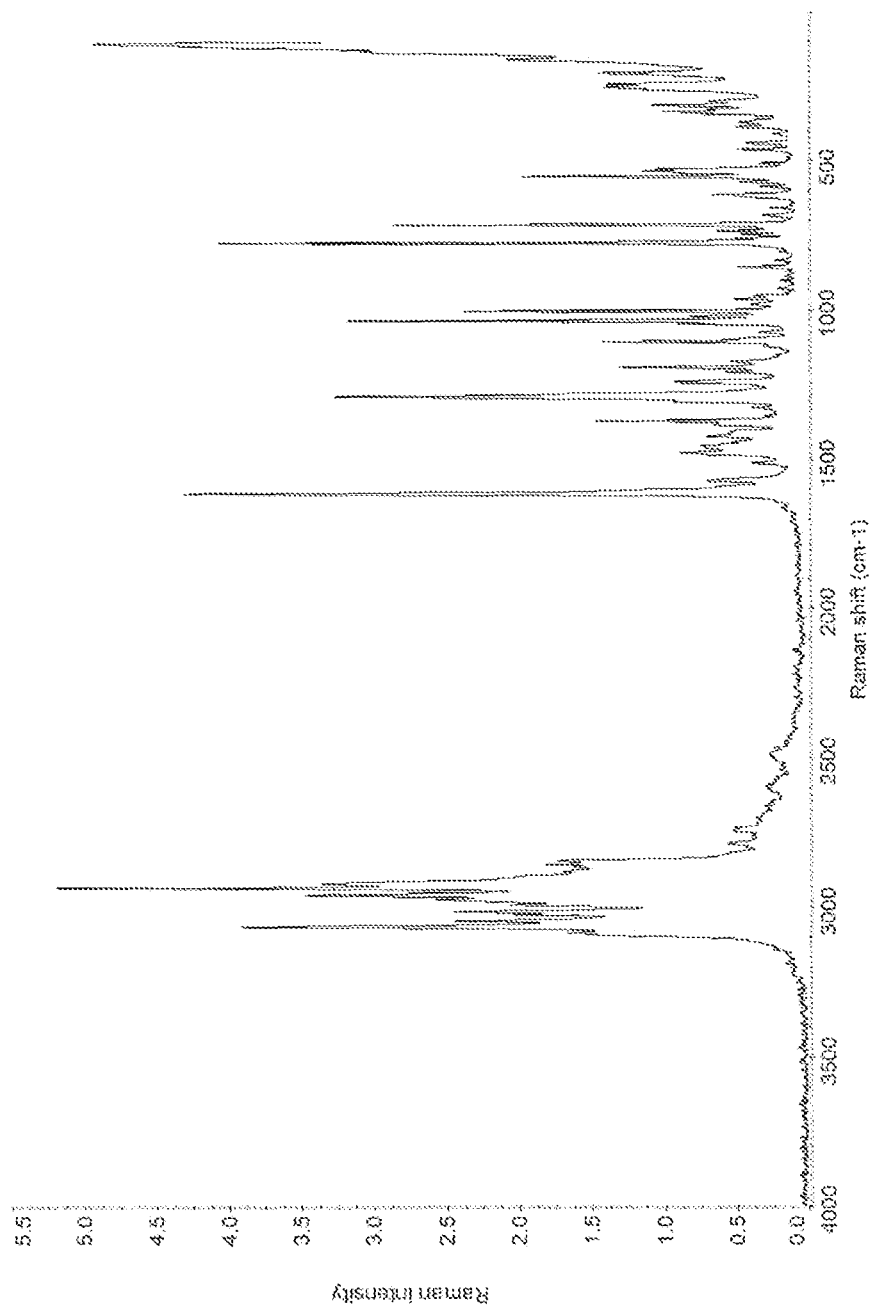
FIG. 5 shows the FT-Ramen Spectrum for FORM 2.

Alternatively or additionally, FORM 2 of 7-(2-(methyloxy)-6-{[(4-methyl-2-pyridinyl)methyl]oxy}phenyl)-2,3,4, 5-tetrahydro-1H-3-benzazepine can be characterised by Raman spectroscopy as shown in FIG. 5, wherein the spectrum is expressed in terms of $cm^{-1}$ and obtained using procedures as herein described. The Raman spectrum of FORM 1 has characteristic peaks at 2934, 1614, 1371, 1005 and 777.

Figure 6:
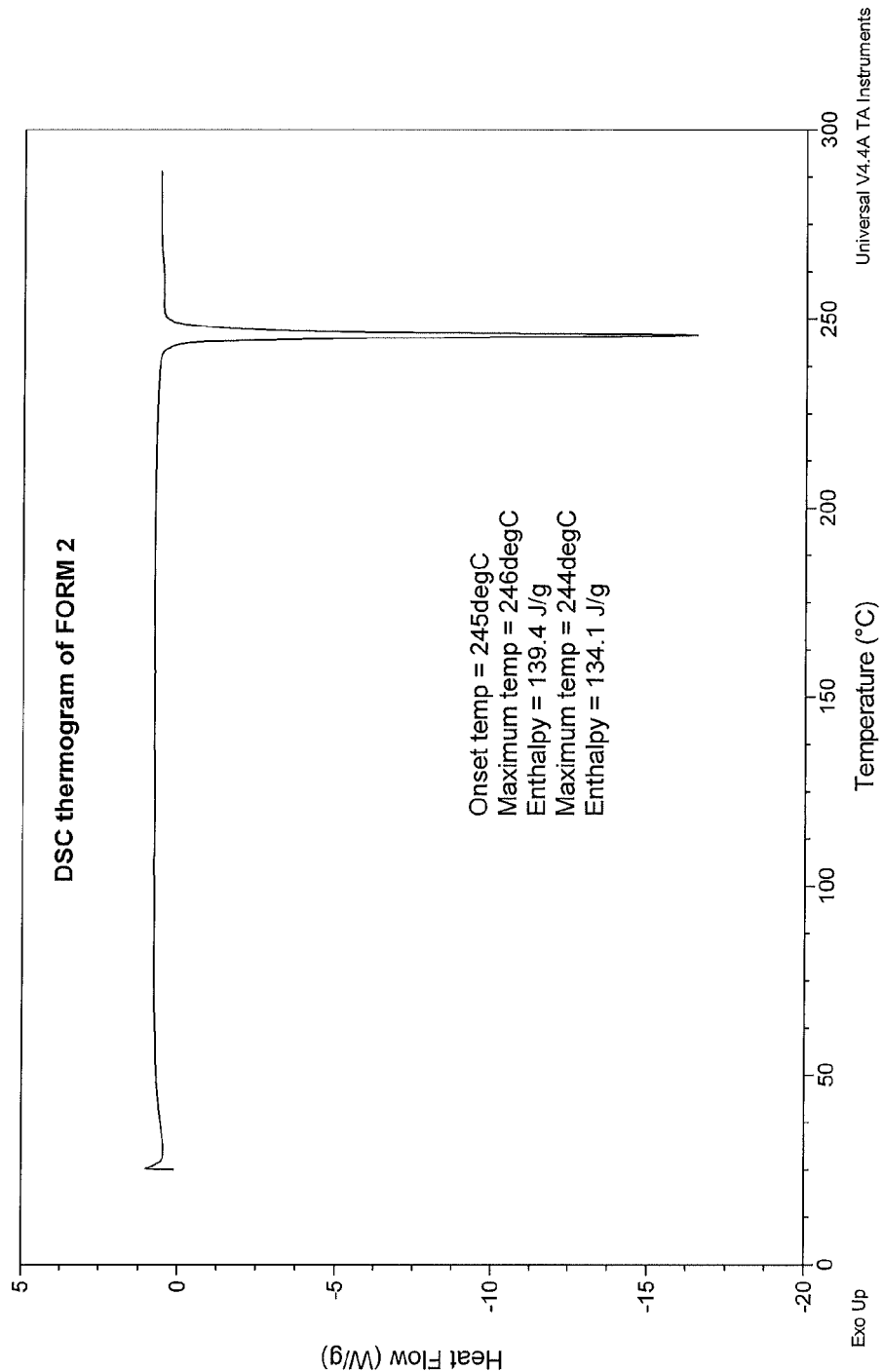
FIG. 6 shows DSC thermogram of FORM 2.

Alternatively or additionally, FORM 2 of 7-(2-(methyloxy)-6-{[(4-methyl-2-pyridinyl)methyl]oxy}phenyl)-2,3,4, 5-tetrahydro-1H-3-benzazepine can be characterised by differential scanning calorimitry (DSC) thermograms as shown in FIG. 6, wherein the DSC was performed using methods as described herein.

A compound of formula (I) may be prepared by the general synthetic schemes described hereinafter.

Scheme 1:

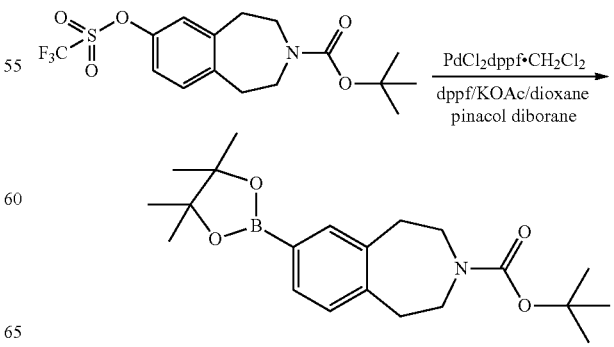

Scheme 2:
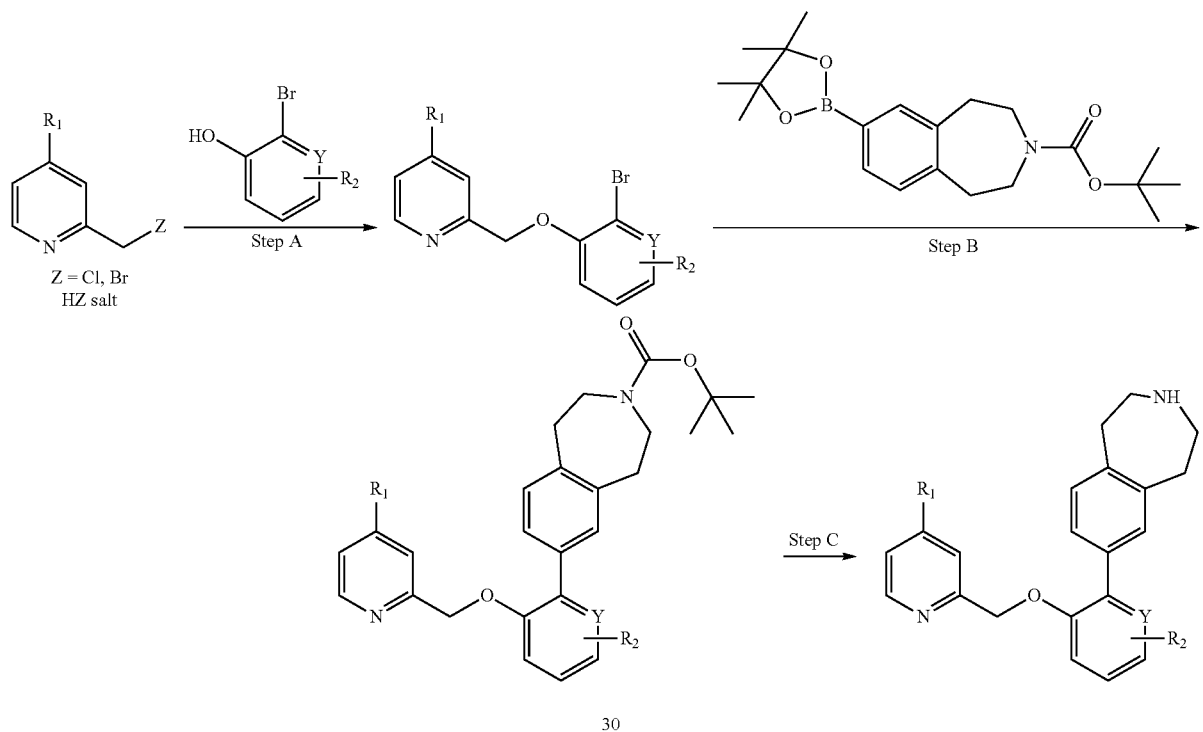
wherein Y, $R_1$ and $R_2$ are as hereinbefore defined.
Step A: Potassium carbonate/DMF
Step B: $PdCl_2$.dppf/caesium carbonate/aqueous dioxane/heat; or
tetrakis/sodium carbonate/aqueous DME/heat
Step C: HCl in dioxane; or
trifluoroacetic acid in dichloromethane
Scheme 3:
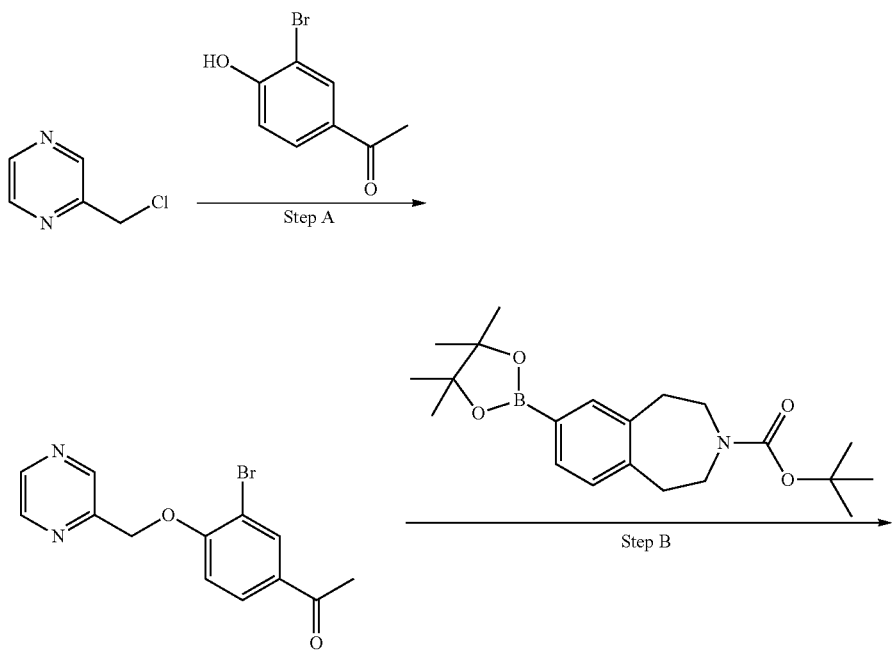

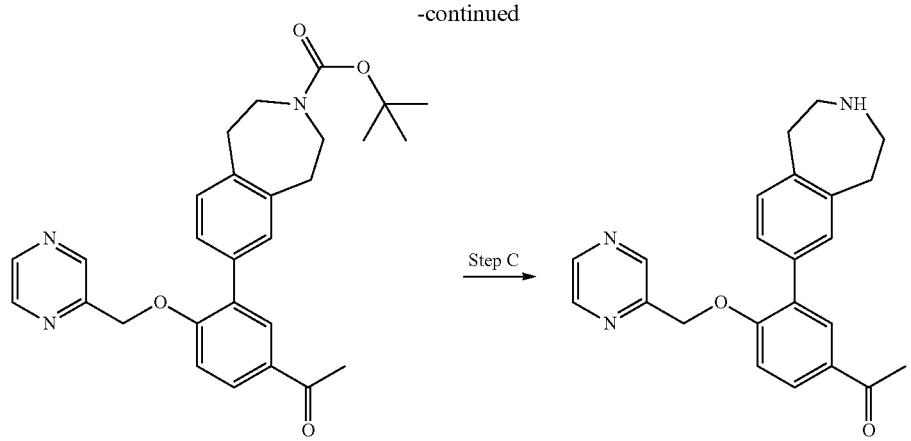
Step A: Potassium carbonate/DMF
Step B: Tetrakis/sodium carbonate/aqueous DME/heat
Step C: HCl in dioxane; or trifluoroacetic acid in dichloromethane
Scheme 4:
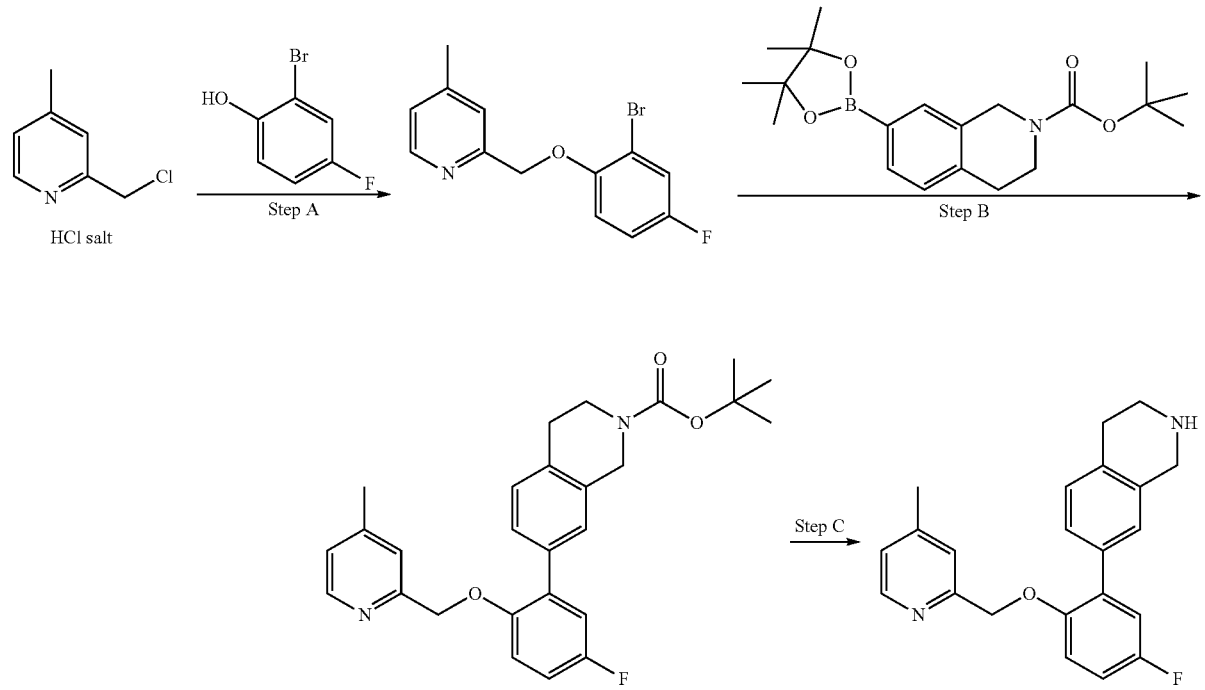
Step A: Potassium carbonate/DMF
Step B: PdCl$_2$•dppf/caesium carbonate/aqueous dioxane/heat
Step C: HCl in dioxane; or trifluoroacetic acid in dichloromethane
Scheme 5:
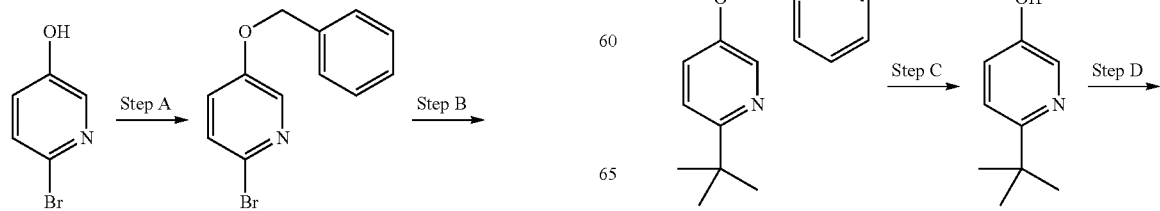

15
-continued

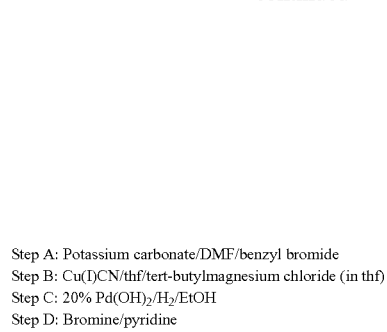

Step A: Potassium carbonate/DMF/benzyl bromide
Step B: Cu(I)CN/thf/tert-butylmagnesium chloride (in thf)
Step C: 20% Pd(OH)$_2$/H$_2$/EtOH
Step D: Bromine/pyridine Scheme 6:

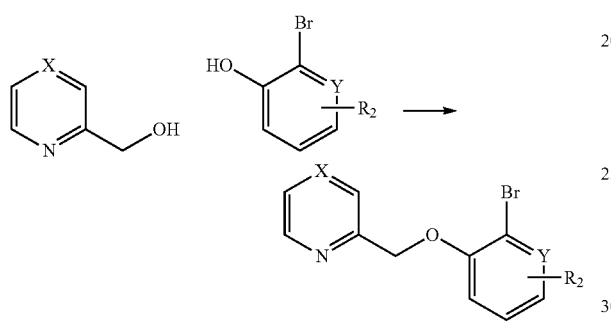

Step A: DEAD/PPh$_3$/thf

Scheme 7:

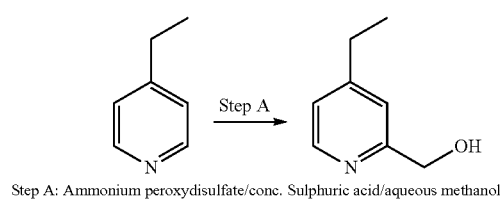

Step A: Ammonium peroxydisulfate/conc. Sulphuric acid/aqueous methanol

Scheme 8:

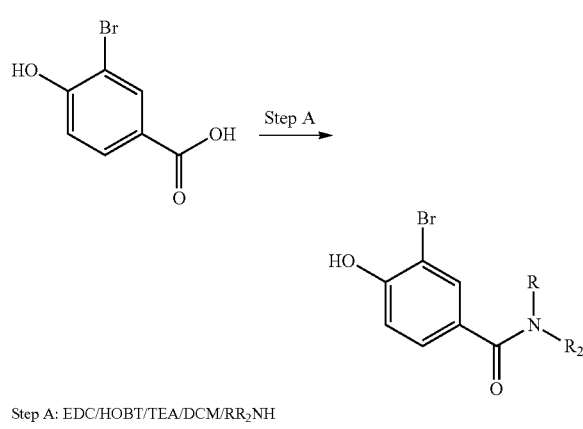

Step A: EDC/HOBT/TEA/DCM/RR$_2$NH

Scheme 9:

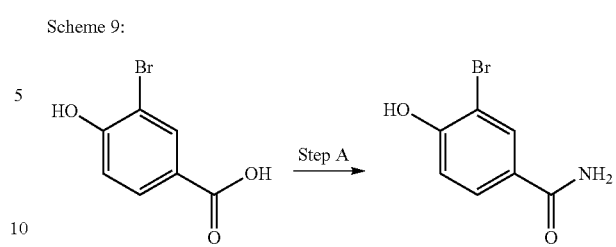

Step A: (i) DCM/DMF/oxalyl chloride. (ii) NH$_3$

Scheme 10:

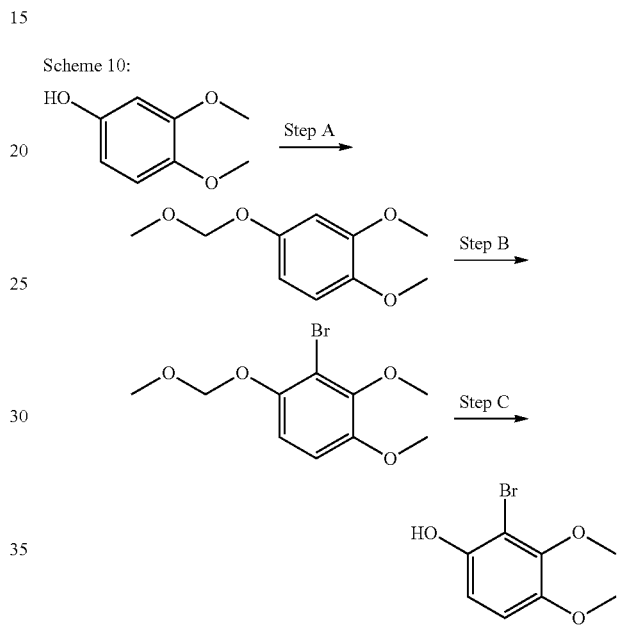

Step A: chloromethyl methyl ether/DIPEA/DCM
Step B: (i) TMEDA/tert-BuLi/Et$_2$O (ii) Bromine
Step C: Conc. Hydrochloric acid/methanol Scheme 11

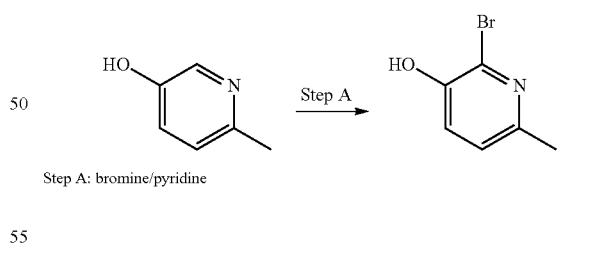

Step A: bromine/pyridine

Scheme 12

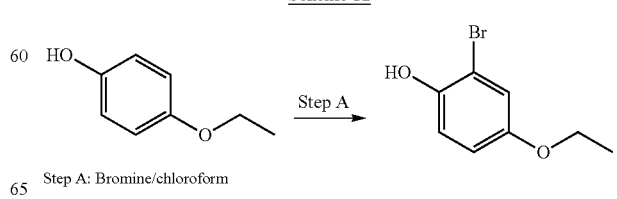

Step A: Bromine/chloroform

Scheme 13
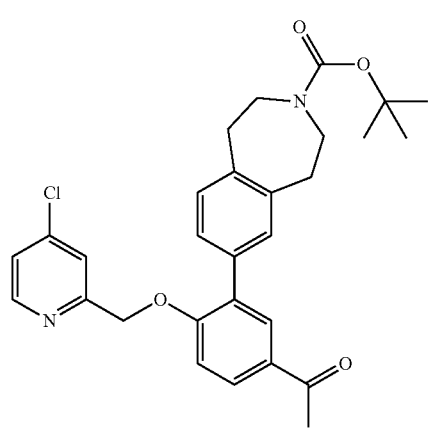
Step A →
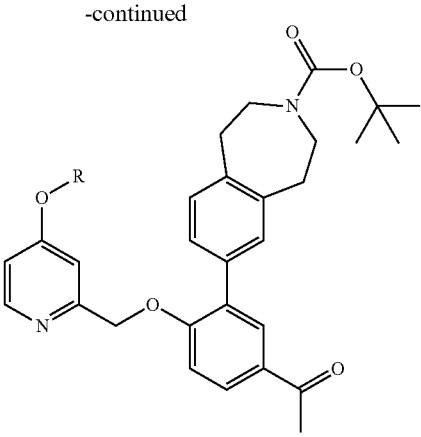
Step A: KOtBu/ROH/110° C.

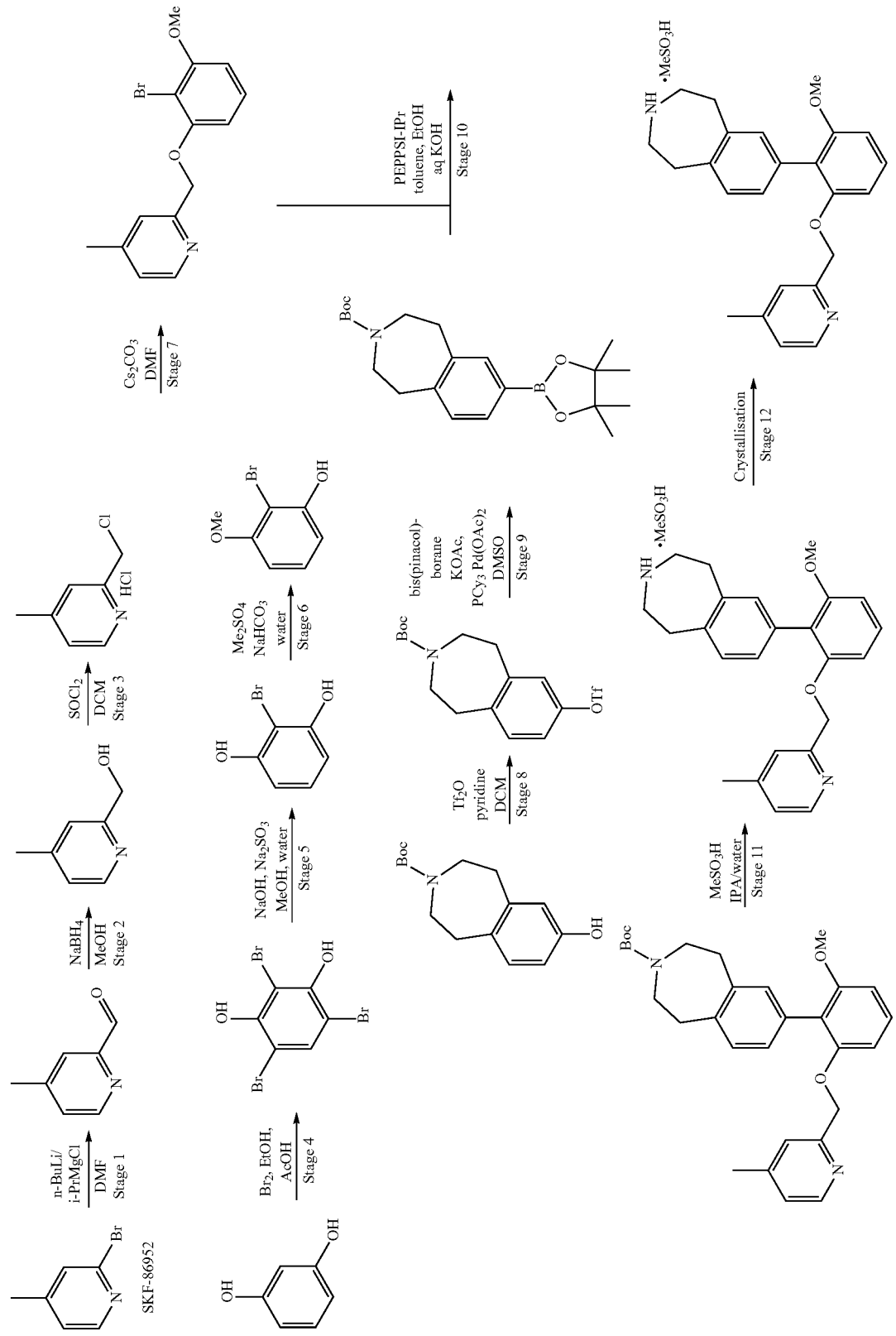

Thus, in a further aspect, the present invention provides a process for preparing a compound of formula (I) which process comprises reacting a compound of formula (II):

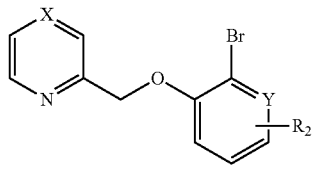

(II)

wherein X, Y and $R_2$ are as hereinbefore defined;
with a boronic ester or acid of formula (III):

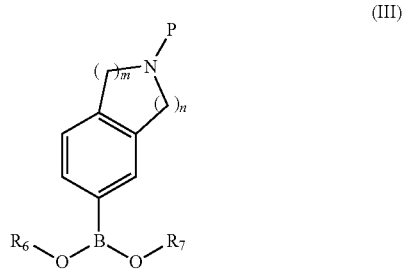

(III)

wherein $R_6$ and $R_7$ which may be the same or different are each hydrogen, $C_{1-6}$alkyl or $R_6$ and $R_7$ may be joined to form a $C_{1-3}$alkylene group optionally substituted by up to four methyl groups, for instance —C(Me)$_2$C(Me)$_2$—;
P is a protecting group; and
m and n are as hereinbefore defined;
in the presence of a catalyst, under conditions typically used for a boronic ester/acid coupling; and
thereafter, removing any protecting group.

Conditions typically used for a boronic ester/acid coupling includes the use of the Pd(PPh$_3$)$_4$ as catalyst, with caesium carbonate in a solvent such as aqueous 1,4-dioxane. Alternatively conditions that could be used include the use of PEPPSI™ as catalyst, with potassium hydroxide in a solvent such as aqueous dimethoxyethane (DME) with ethanol.

Examples of protecting groups and the means for their removal can be found in T. W. Greene 'Protective Groups in Organic Synthesis' (J. Wiley and Sons, 1991). Suitable amine protecting groups include, but are not restricted to, sulphonyl (such as tosyl), acyl (such as benzyloxycarbonyl or t-butoxycarbonyl) and arylalkyl (such as benzyl), which may be removed by hydrolysis or hydrogenolysis as appropriate. Other suitable amine protecting groups include trifluoroacetyl (—C(O)CF$_3$), which may be removed by base catalysed hydrolysis, or a solid phase resin bound benzyl group, such as a Merrifield resin bound 2,6-dimethoxybenzyl group (Ellman linker) which may be removed by acid catalysed hydrolysis (using, for example, trifluoroacetic acid).

In one embodiment of the present invention the protecting group (P) is selected from tert-butyloxycarbonyl "BOC" and 9-fluorenylmethyloxycarbonyl "FmoC".

Compounds of formula (I) are useful as inhibitors of Syk and thus potentially of use in treating some cancer therapies, in particular heme malignancies, as well as inflammatory conditions which involve B cells, and also diseases resulting from inappropriate mast cell activation, for instance allergic and inflammatory diseases such as cutaneous mast cell mediated diseases including acute and chronic urticaria, mastocytosis, atopic dermatitis and autoimmune diseases such as cutaneous lupus and autoimmune bullous conditions including pemphigus and pemphigoid.

In one aspect, the present invention provides a compound of formula (I) or a pharmaceutically acceptable salt thereof, for use in therapy.

In another aspect, the present invention provides a compound of formula (I) or a pharmaceutically acceptable salt thereof, for use in inhibiting spleen tyrosine kinase (Syk).

In a further aspect, the present invention provides a method comprising administering to a subject, particularly a human subject in need thereof an effective amount of a compound of formula (I) or a pharmaceutically acceptable salt thereof, to inhibit a spleen tyrosine kinase (Syk).

Syk inhibitors may be useful in cancer therapy, specifically heme malignancies, particularly Non-Hodgkin's Lymphomas including follicular (FL), mantle cell, small lymphocytic lymphoma/chronic lymphocytic lymphoma (SLL/CLL), Burkitt and diffuse large B cell (DLBCL) lymphomas. Syk inhibitors may also be useful in the treatment of Acute myeloid leukaemia and retinoblastoma.

In one aspect, the present invention provides a compound of formula (I) or a pharmaceutically acceptable salt thereof, for use in the treatment of cancer, for example, Acute myeloid leukaemia, retinoblastoma, heme malignancies, particularly Non-Hodgkin's lymphomas including follicular (FL), mantle cell, small lymphocytic lymphoma/chronic lymphocytic lymphoma (SLL/CLL), Burkitt and diffuse large B cell (DLBCL) lymphomas.

In another aspect, the present invention provides a method of treating cancer, for example, Acute myeloid leukaemia, retinoblastoma, heme malignancies, particularly Non-Hodgkin's Lymphomas including follicular (FL), mantle cell, small lymphocytic lymphoma/chronic lymphocytic lymphoma (SLL/CLL), Burkitt and diffuse large B cell (DLBCL) lymphomas, which method comprises administering to a subject, particularly a human subject in need thereof a therapeutically effective amount of a compound of formula (I) or a pharmaceutically acceptable salt thereof.

In a further aspect, the present invention provides the use of a compound of formula (I) or a pharmaceutically acceptable salt thereof, for the manufacture of a medicament for the treatment of cancer, for example, Acute myeloid leukaemia, retinoblastoma, heme malignancies, particularly Non-Hodgkin's lymphomas including follicular (FL), mantle cell, small lymphocytic lymphoma/chronic lymphocytic lymphoma (SLL/CLL), Burkitt and diffuse large B cell (DLBCL) lymphomas.

Compounds of formula (I) may also be used in cancer chemotherapy in combination with other classes of cancer chemotherapy agents which are known in the art. Representative classes of agents for use in such combinations for Non-Hodgkin's Lymphomas include rituximab, BEXXAR (tositumomab and Iodine I 131 tositumomab) and pixantrone. Compounds of the Formula (I) may also be used in combination with the CHOP drug regime (cyclophosphamide, adriamycin, vincristine, prednisone) or CHOP plus rituximab (CHOP+R).

Compounds of formula (I) are potentially of use in treating autoimmune conditions which involve B cells and/or macrophage activation, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, chronic idiopathic urticaria with and without auto-antibody status (chronic autoimmune urticaria (New concepts in chronic urticaria, Current Opinions in Immunology 2008 20:709-716)), glomerulonephritis, chronic transplant rejection, and rheumatoid arthritis.

In one aspect, the present invention provides a compound of formula (I) or a pharmaceutically acceptable salt thereof, for use in the treatment of an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, chronic idiopathic urticaria with and without auto-antibody status (chronic autoimmune urticaria (New concepts in chronic urticaria, Current Opinions in Immunology 2008 20:709-716)), glomerulonephritis, chronic transplant rejection, and rheumatoid arthritis. In one embodiment, the present invention provides a compound of formula (I) or a pharmaceutically acceptable salt thereof for use in the treatment of an autoimmune condition which is chronic idiopathic urticaria with and without auto-antibody status. In another embodiment, the present invention provides a compound of formula (I) or a pharmaceutically acceptable salt thereof for use in the treatment of an autoimmune condition which is discoid (cutaneous) lupus.

In another aspect, the present invention provides a method of treating an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, chronic idiopathic urticaria with and without auto-antibody status, glomerulonephritis, chronic transplant rejection and rheumatoid arthritis, which method comprises administering to a subject, particularly a human subject in need thereof a therapeutically effective amount of a compound of formula (I) or a pharmaceutically acceptable salt thereof. In one embodiment, the present invention provides a method of treating an autoimmune disease which is chronic idiopathic urticaria with and without auto-antibody status, which method comprises administering to a subject, particularly a human subject in need thereof a therapeutically effective amount of a compound of formula (I) or a pharmaceutically acceptable salt thereof. In another embodiment, the present invention provides a method of treating an autoimmune disease which is discoid (cutaneous) lupus, which method comprises administering to a subject, particularly a human subjectin need thereof a therapeutically effective amount of a compound of formula (I) or a pharmaceutically acceptable salt thereof.

In a further aspect, the present invention provides the use of a compound of formula (I) or a pharmaceutically acceptable salt thereof, for the manufacture of a medicament for the treatment of an autoimmune condition, for example systemic lupus erythematosus (SLE), discoid (cutaneous) lupus, Sjorgens syndrome, Wegners granulomatosis and other vasculitides, bullous pemphigoid and pemphigus, idiopathic thrombocytopenic purpura (ITP), giant cell arteriosis, chronic idiopathic urticaria with and without auto-antibody status, glomerulonephritis, chronic transplant rejection and rheumatoid arthritis. In one embodiment, the present invention provides the use of a compound of formula (I) or a pharmaceutically acceptable salt thereof for the manufacture of a medicament for the treatment of an autoimmune condition which is chronic idiopathic urticaria with and without auto-antibody status. In another embodiment, the present invention provides the use of a compound of formula (I) or a pharmaceutically acceptable salt thereof for the manufacture of a medicament for the treatment of an autoimmune condition which is discoid (cutaneous) lupus.

In one aspect, the present invention provides a compound of formula (I) or a pharmaceutically acceptable salt thereof, for use in the treatment of an inflammatory disease which involves B cells.

In another aspect, the present invention provides a method of treating an inflammatory disease which involves B cells which method comprises administering to a subject, particularly a human subject in need thereof a therapeutically effective amount of a compound of formula (I) or a pharmaceutically acceptable salt thereof.

In a further aspect, the present invention provides the use of a compound of formula (I) or a pharmaceutically acceptable salt thereof, for the manufacture of a medicament for the treatment of an inflammatory disease which involves B cells.

Compounds of formula (I) are potentially of use in treating diseases resulting from inappropriate mast cell activation, for instance allergic and inflammatory diseases particularly with skin manifestations.

In one aspect, the present invention provides a compound of formula (I) or a pharmaceutically acceptable salt thereof, for use in the treatment of a disease associated with inappropriate mast cell activation.

In another aspect, the present invention provides a method of treating a disease associated with inappropriate mast cell activation which method comprises administering to a subject, particularly a human subject in need thereof a therapeutically effective amount of a compound of formula (I) or a pharmaceutically acceptable salt thereof.

In a further aspect, the present invention provides the use of a compound of formula (I) or a pharmaceutically acceptable salt thereof, for the manufacture of a medicament for the treatment of a disease associated with inappropriate mast cell activation.

In one aspect, the present invention provides a compound of formula (I) or a pharmaceutically acceptable salt thereof, for use in the treatment of an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis.

In another aspect, the present invention provides a method of treating an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis, which method comprises administering to a subject, particularly a human subject in need thereof a therapeutically effective amount of a compound of formula (I) or a pharmaceutically acceptable salt thereof.

In a further aspect, the present invention provides the use of a compound of formula (I) or a pharmaceutically acceptable salt thereof, for the manufacture of a medicament for the treatment of an inflammatory disease and/or allergic disorder for example, chronic obstructive pulmonary disease (COPD), adult respiratory distress syndrome (ARDS), asthma, severe asthma, ulcerative colitis, Crohn's disease, bronchitis, conjunctivitis, psoriasis, scleroderma, dermatitis, allergy, rhinitis, cutaneous lupus, autoimmune bullous conditions including pemphigus and pemphigoid, mastocytosis and anaphylaxis.

Compounds of formula (I) may also be used in combination with other classes of therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines.

In another embodiment, compounds of formula (I) may be used in combination with other classes of therapeutic agents which are known in the art for treating autoimmune diseases, for instance disease modifying anti-rheumatic drugs including cyclosporine, methotrexate, sulphasalazine, prednisone, leflunomide, and chloroquine/hydrochloroquine and also biopharmaceutical agents such as humanised monoclonal antibodies (mabs), for example including anti-TNF alpha blockers such as remicade, enbrel and humira, B cell depleting therapies such as rituximab and ofatumumab, and anti-Blys mabs such as belilumab.

The invention thus provides, a combination comprising a compound of formula (I) or a pharmaceutically acceptable salt thereof together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, an antihistamine, a disease modifying anti-rheumatic drug, and a biopharmaceutical agent such as humanised monoclonal antibodies (mabs), B cell depleting therapies and anti-Blys mabs. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine, and/or a disease modifying anti-rheumatic drug, and/or a biopharmaceutical agent.

One embodiment of the invention encompasses combinations comprising one or two other therapeutically active agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

Other $\beta_2$-adrenoreceptor agonists include those described in WO02/066422, WO02/070490, WO02/076933, WO03/024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino) heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Examples of corticosteroids may include those described in WO02/088167, WO02/100879, WO02/12265, WO02/12266, WO05/005451, WO05/005452, WO06/072599 and WO06/072600.

Anti-inflammatory corticosteroids are well known in the art. Representative examples include fluticasone propionate (e.g. see U.S. Pat. No. 4,335,121), fluticasone furoate (e.g. see U.S. Pat. No. 7,101,866), beclomethasone 17-propionate ester, beclomethasone 17,21-dipropionate ester, dexamethasone or an ester thereof, mometasone or an ester thereof (e.g. mometasone furoate), ciclesonide, budesonide, flunisolide, methyl prednisolone, prednisolone, dexamethasone and $6\alpha,9\alpha$-difluoro-11$\beta$-hydroxy-16$\alpha$-methyl-3-oxo-17$\alpha$-(2,2,3,3-tetramethycyclopropylcarbonyl)oxy-androsta-1,4-diene-17$\beta$-carbothioic acid S-cyanomethyl ester. Further examples of anti-inflammatory corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those covered in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000334 and WO07/054294.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

Examples of PDE4 inhibitors include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms (e.g. see U.S. Pat. No. 5,552,438).

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (e.g. see WO99/47505) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;

(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I), or a pharmaceutically acceptable salt thereof, together with an H1 antagonist. Examples of H1 antagonists include, without limitation, methapyrilene, desloratadine, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I), or a pharmaceutically acceptable salt thereof, together with an H3 antagonist (and/or inverse agonist). Examples of H3 antagonists include, for example, those compounds disclosed in WO2004/035556 and in WO2006/045416. Other histamine receptor antagonists which may be used in combination with the compounds of formula (I), or a pharmaceutically acceptable salt thereof, include antagonists (and/or inverse agonists) of the H4 receptor, for example, the compounds disclosed in Jablonowski et al., *J. Med. Chem.* 46:3957-3960 (2003).

In one embodiment there is provided, a combination comprising a compound of formula (I) or a pharmaceutically acceptable salt thereof together with a corticosteroid. In another embodiment there is provided, a combination comprising a compound of formula (I) or a pharmaceutically acceptable salt thereof together with an NSAID. In another embodiment there is provided, a combination comprising a compound of formula (I) or a pharmaceutically acceptable salt thereof together with an anticholinergic. In another embodiment there is provided, a combination comprising a compound of formula (I) or a pharmaceutically acceptable salt thereof together with a $\beta_2$-adrenoreceptor agonist. In another embodiment there is provided, a combination comprising a compound of formula (I) or a pharmaceutically acceptable salt thereof together with an antiinfective. In another embodiment there is provided, a combination comprising a compound of formula (I) or a pharmaceutically acceptable salt thereof together with an antihistamine. In another embodiment there is provided, a combination comprising a compound of formula (I) or a pharmaceutically acceptable salt thereof together with a disease modifying anti-rheumatic drug. In a further embodiment there is provided, a combination comprising a compound of formula (I) or a pharmaceutically acceptable salt thereof together with a biopharmaceutical agent.

A compound of formula (I) will normally, but not necessarily, be formulated into pharmaceutical compositions prior to administration to a patient. Accordingly, in another aspect the invention is directed to pharmaceutical compositions comprising a compound of formula (I), or a pharmaceutically acceptable salt thereof, and one or more pharmaceutically acceptable carriers, diluents or excipients.

The pharmaceutical compositions of compounds of formula (I) may be prepared and packaged in bulk form wherein a safe and effective amount of a compound of the formula (I) can be extracted and then given to the patient, such as with powders or syrups. Alternatively, the pharmaceutical compositions of compounds of formula (I) may be prepared and packaged in unit dosage form wherein each physically discrete unit contains a safe and effective amount of a compound of the formula (I). The pharmaceutical compositions of compounds of formula (I) may also be prepared and packaged in a sub-unit dosage form wherein two or more sub-unit dosage forms provide the unit dosage form. When prepared in unit dosage form, the pharmaceutical compositions of compounds of formula (I) typically contain from about 0.1 to 99.9 wt. %, of the compound of formula (I), depending on the nature of the formulation.

In addition, the pharmaceutical compositions of compounds of formula (I) may optionally further comprise one or more additional therapeutically active compounds.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of formula (I) when administered to a patient and would result in pharmaceutically unacceptable compositions are avoided. In addition, each excipient must of course be of sufficiently high purity to render it pharmaceutically acceptable.

Compositions comprising a compound of formula (I), or a pharmaceutically acceptable salt thereof and one or more pharmaceutically acceptable carriers, diluents or excipients will typically be provided as a dosage form adapted for administration to the patient by the desired route of administration. For example, dosage forms include those adapted for: (1) oral administration, such as tablets, capsules, caplets, pills, troches, powders, syrups, elixers, suspensions, solutions, emulsions, sachets, and cachets; (2) topical dermal administration, such as creams, ointments, lotions, solutions, pastes, sprays, foams, and gels, (3) inhalation, such as aerosols and solutions; (4) intranasal administration, such as solutions or sprays; (5) parenteral administration, such as sterile solutions, suspensions, and powders for reconstitution and (6) intravitreal administration.

In one embodiment there is provided a dosage form adapted for topical dermal administration.

It will be appreciated that dosage forms adapted for oral administration are commonly used for treating autoimmune disease including rheumatoid arthritis and systemic lupus erythematosus, chronic idiopathic urticarias and heme malignancies. Dosage forms adapted for topical administration to the skin are commonly used for treating atopic dermatitis, psoriasis and chronic and acute urticaria conditions, and autoimmune bullous conditions including pemphigus and pemphigoid. Dosage forms adapted for inhalation or oral administration are commonly used for treating COPD; whilst dosage forms adapted for intranasal administration are commonly used for treating allergic rhinitis.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of formula (I) once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavouring agents, flavour masking agents, colouring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), Remington: The Science and Practice of Pharmacy, (Lippincott Williams & Wilkins), The Handbook of Pharmaceutical Additives (Gower Publishing Limited), and The Handbook of Pharmaceutical Excipients (the American Pharmaceutical Association and the Pharmaceutical Press).

The pharmaceutical compositions of compounds of formula (I) are prepared using techniques and methods known to those skilled in the art. Some of the methods commonly used in the art are described in Remington's Pharmaceutical Sciences (Mack Publishing Company).

Oral solid dosage forms such as tablets will typically comprise one or more pharmaceutically acceptable excipients, which may for example help impart satisfactory processing and compression characteristics, or provide additional desirable physical characteristics to the tablet. Such pharmaceutically acceptable excipients may be selected from diluents, binders, glidants, lubricants, disintegrants, colorants, flavourants, sweetening agents, polymers, waxes or other solubility-modulating materials.

Dosage forms for topical administration to the skin may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [ibid]. The pH of such IV fluids may vary, and will typically be from 3.5 to 8, as known in the art.

Dosage forms for nasal or inhaled administration may conveniently be formulated as aerosols, solutions, drops, gels or dry powders.

Dosage forms for topical administration to the nasal cavity (nasal administration) include pressurised aerosol formulations and aqueous formulations administered to the nose by pressurised pump. Formulations which are non-pressurised and adapted for nasal administration are of particular interest. Suitable formulations contain water as the diluent or carrier for this purpose. Aqueous formulations for administration to the nose may be provided with conventional excipients such as buffering agents, tonicity modifying agents and the like. Aqueous formulations may also be administered to the nose by nebulisation.

Dosage forms for nasal administration are provided in a metered dose device. The dosage form may be provided as a fluid formulation for delivery from a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. In one embodiment, the fluid dispenser is of the general type described and illustrated in WO2005/044354A1. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO2005/044354A1.

Aerosol compositions, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, a compound of formula (I) (preferably in particle-size-reduced form, e.g. in micronised form), and optionally a performance modifier such as L-leucine or another amino acid, cellobiose octaacetate and/or metals salts of stearic acid such as magnesium or calcium stearate. Preferably, the dry powder inhalable composition comprises a dry powder blend of lactose and a compound of formula (I). The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device, marketed by GlaxoSmithKline. The DISKUS® inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

A composition of invention compound of formula (I), for intranasal administration, may also be adapted for dosing by insufflation, as a dry powder formulation.

For dosage forms for inhaled administration, where the compound of formula (I) is present as a dry powder or in suspension, then it is preferred that it is in a particle-size-reduced form. Preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

It will be appreciated that when the compounds of formula (I) are administered in combination with other therapeutic agents normally administered by the inhaled, intravenous, oral, topical or intranasal route, that the resultant pharmaceutical composition may be administered by the same routes.

The composition may contain from 0.1% to 100% by weight, for example from 10 to 60% by weight, of the active material, depending on the method of administration.

The composition may contain from 0% to 99% by weight, for example 40% to 90% by weight, of the carrier, depending on the method of administration. The compounds of the formula (I) may conveniently be administered in amounts of, for example, 1 µg to 2 g. The precise dose will of course depend on the age and condition of the patient and the particular route of administration chosen.

Biological Test Methods

Compounds may be tested for in vitro activity in accordance with the following assays:

1. Basic SYK Enzyme Activity

3 µl of SYK lysate diluted 16-fold in assay buffer (20 mM TRIS pH 7.4, 0.01% BSA, 0.1% Pluronic F-68) was added to wells containing 0.1 µl of various concentrations of compound or DMSO vehicle (1.7% final) in a Greiner low volume 384 well black plate. Following 15 minutes pre-incubation at room temperature, the reaction was initiated by the addition of 3 µl of substrate reagent containing Y7 Sox peptide, (Invitrogen Cat. # KNZ3071, 5 µM final), ATP (35 µM final) and $MgCl_2$ (10 mM final) in assay buffer. The reaction was incubated at room temperature before measuring fluorescence intensity ($\lambda_{ex}$ 360/$\lambda_{em}$ 485) on an Envision plate reader (Perkin Elmer Life Sciences, Waltham, Mass., USA) at 15 minutes and 55 minutes post-substrate addition.

The compounds of the Examples were tested essentially as described above, and were found to have a $pIC_{50}$ of 5.5 to 7.5. The compounds of Examples 1 to 8 were tested essentially as described above and were found to have an average $pIC_{50}$ value in this assay of 6.0. The compound of Example 2 was tested essentially as described above and was found to have a $pIC_{50}$ of 7.1.

Those of skill in the art will recognize that in vitro binding assays and cell-based assays for functional activity are subject to variability. Accordingly, it is to be understood that the values for the $pIC_{50}$s recited above are exemplary only.

Preparation of SYK Lysate i. Preparation of Ramos Cell Lysates

Ramos B Cells (human B cells of Burkitt's lymphoma, clone 296.4C10, ATCC) were cultured in suspension in growth medium (RPMI-1640, Sigma; supplemented with 2 mM L-glutamine, Gibco; 10 mM Hepes, Sigma; 1 mM sodium pyruvate, Sigma; 10% v/v heat-inactivated FCS, Gibco). Cells were grown in Corning Cellstacks (6360 $cm^2$) in 1 liter volume and viability and cell density were monitored daily. Cells were maintained at <1.5×10e6/ml and >92% viability Large scale production runs were generated from Large Scale Intermediate Aliquots (LSIA's) of frozen Ramos cells as this was found to give greater reproducibility than production from a continuously growing culture of Ramos cells.

The large scale production run cells were generated in four steps:

1. Thaw LSIA into 1× Cellstack;
2. Expand culture into 4× Cellstack;
3. Expand from 4 to 12× Cellstacks;
4. Harvest all 12 Cellstacks Cellstacks were harvested in 2 L centrifuge bottles using a Sorvall Mistral centrifuge, 2000 rpm, 10 minutes, 4° C. (2 L×2×$10^6$ cells/ml=4×$10^9$ cells total)

(Notes for cell scale-up: If the cell density exceeded 1.8× 10e6/ml or viability dropped below 90% the Syk prep obtained post-stimulation was likely to be of lower activity).

Also, repeated passage of the Ramos cells seemed to have a detrimental effect on Syk activity when cell growth is done at scale (this did not seem to be the case in small scale cultures)—it is recommended always to use LSIA's and modular scale-up for large scale preps.

ii. Stimulation of Ramos Cells with Anti-IgM Ab to Produce Syk & Preparation of Lysates Cells were stimulated at $20 \times 10^6$ cells/ml using 15 ug/ml (final concentration) anti-IgM antibody. Following harvest (as described above), a total of $4 \times 10^9$ cells were resuspended in 180 mls pre-warmed (37° C.) DPBS in a Corning 500 ml centrifuge bottle. 20 mls anti-IgM antibody at 150 ug/ml were added to each 500 ml centrifuge bottle. (working stock made up in DPBS pre-warmed to 37° C.). Cells were incubated for exactly 5 minutes at 37° C. following the addition of anti IgM antibody. Following 5 minutes stimulation, 300 mls ice-cold DPBS were added to each bottle to stop the stimulation (temperature drops to ~12 deg C.) then cells were centrifuged at 2000 rpm (Sorvall Legend RT+ centrifuge—pre-chilled to 4 deg C.). Cells were washed by resuspension in ice-cold DPBS and centrifugation as above. The cell pellet was then lysed in ice-cold lysis buffer containing 1% triton-x-100 at a ratio of 150 ul/$1 \times 10^7$ cells (i.e. 48 mls lysis buffer). Following the addition of lysis buffer, the cells were pipetted up & down & kept on ice for 15 minutes. The clarified lysate was then obtained by centrifugation (Sorvall Evolution RC (SLA-1500 rotor, ~20,000 g (~14,500 rpm), 45 min, 4° C.).

Lysate was aliquoted, snap-frozen on dry-ice & stored at −80° C. prior to assay.

Materials

Ramos Cells: Human B cells of Burkitts lymphoma, clone 296.4C10 (ATCC).

Growth Media: 500 ml RPMI, 10% heat inactivated FCS, 2 mM L-Glutamine, 2 mM

HEPES, 1 mM sodium pyruvate.
    RPMI: Sigma R0883, stores CT5652
    Foetal Calf Serum: Gibco 10099-141, stores CT2509
    L-Glutamine: 200 mM, Gibco 25030, stores CT3005
    HEPES: 1M, Sigma H0887, stores CT5637
    Sodium Pyruvate: 100 mM, Sigma S8636, stores CT7741
    Anti-IgM Ab: Goat anti-human IgM ((Fab')$_2$ fragments) in PBS. Invitrogen, custom-made preparation (azide free and low endotoxin levels). Catalogue no. NON0687, Lot 1411913. 2.74 mg/ml.
    D-PBS: Dulbeccos phosphate buffered saline, Sigma D8537
    Lysis Buffer: 50 mM TRIS pH7.5+150 mM NaCl+1% Triton-X-100+2 mM EGTA+1:100 dilution inhibitor cocktails (Phosphatase inhibitor cocktail set II, Calbiochem cat no. 524625 & Protease inhibitor cocktail set V, Calbiochem cat no. 539137)
    Triton-X-100: Roche 10 789 704 001 (GI 198233X, SC/159824). Made up as a 20% stock in water.
    EGTA: Sigma E4378. Added solid directly to buffer.

2. B Cell Activity Assays 2.1. Ramos pErk Assay

Principle of the Assay

Ramos B cells (human B cells of Burkitt's Lymphoma) are stimulated using anti-IgM. This results in the recruitment of SYK to the B cell receptor. The subsequent autophosphorylation of Syk leads to initiation of a signalling cascade resulting in B cell activation via the Erk MAP Kinase pathway. As a result Erk is phosphorylated and following cell lysis is detected by an immune capture assay.

Stimulation of Ramos Cells with Anti-IgM

Cells were plated at a density of $2.5 \times 10^5$/well in a volume of 25 µl assay medium (RPMI containing 10% heat inactivated foetal calf serum, 1% L-glutamine) in 96 v-well polypropylene plates. 25 µl appropriately diluted compound solution was added and the plate incubated for 30 min at 37° C. with 5% $CO_2$. Cells were stimulated with 5 µl Fab'$_2$ fragments of goat anti-human IgM (5 µg/ml final) for 7 min at 37° C. Cells are lysed by the addition of 55 µL 2×RIPA lysis buffer for 2 h at 4° C. Lysate may be frozen at this point at −80° C.

pErk MSD Assay

50 µl cell lysate was transferred to a 96 well MSD plate coated with anti-pErk1/2 (Thr/Tyr:202/204; 185/187) capture antibody and incubated for 16 hours at 4° C. or 3 hours at room temperature. The plate was washed and an anti-pErk detection antibody added (25 µl/well) for 1 hour at room temperature. This was removed, 150 µL MSD read buffer added and the resultant electrochemiluminescence signal measured.

Compound Preparation

Compound was prepared as a 10 mM stock in DMSO and a dilution series prepared in DMSO using 9 successive 5-fold dilutions. This dilution series was diluted a further 1:100 with assay medium to give the final concentration range to be tested of $5 \times 10^{-5}$ to $2.56 \times 10^{-11}$ M. Compound dilutions were prepared using the Biomek 2000 and Biomek Nx automated robotic pipetting systems.

Compounds of Examples 1-4, 6, 7, 9, 10-12, 15-17, 19, 20, 22, 24, 26-39, 41, 45, 46, 48 and 49 were tested essentially as described above, and were found to have average $pIC_{50}$ values of 5.2 to 6.8. The compounds of Examples 1, 2, 3 and 4 were tested essentially as described above and were found to have an average $pIC_{50}$ value in this assay of 6.0.

Those of skill in the art will recognize that in vitro binding assays and cell-based assays for functional activity are subject to variability. Accordingly, it is to be understood that the values for the $pIC_{50}$s recited above are exemplary only.

INTERMEDIATES AND EXAMPLES

General

All temperatures are in ° C.
BOC refers to tert-butoxycarbonyl
BOC$_2$O refers to Di-tert-butyl dicarbonate
BuOH refers to butanol
Cs$_2$CO$_3$ refers to caesium carbonate
DCM/CH$_2$Cl$_2$ refers to dichloromethane
DEAD refers to diethyl azodicarboxylate
Dioxane refers to 1,4-dioxane
DIPEA refers to N,N-diisopropylethylamine
DMSO refers to dimethylsulfoxide
DME refers to 1,2-dimethoxyethane
DMF refers to N,N-dimethylformamide
Dppf refers to 1,1'-Bis(diphenylphosphino)ferrocene
EA refers to ethyl acetate
EDC refers to N-(3-Dimethylaminopropyl)-N'-ethylcarbodiimide
Et$_3$N refers to triethylamine
Ether refers to diethyl ether
EA/EtOAc refers to ethyl acetate
h refers to hours
HCl refers to hydrogen chloride
HOBT refers to 1-hydroxybenzotriazole
HPLC refers to high performance liquid chromatography
K$_2$CO$_3$ refers to potassium carbonate
KOH refers to potassium hydroxide
LCMS refers to liquid chromatography-mass spectroscopy MDAP refers to mass directed automated preparative chromatography
min refers to minutes
NaHCO$_3$ refers to sodium bicarbonate
NH$_4$Cl refers to ammonium chloride
NMP refers to N-methylpyrrolidone
PEPPSI refers to Pyridine-Enhanced Precatalyst Preparation Stabilization and Initiation
Pd/C refers to palladium on carbon
PdCl$_2$.dppf refers to [1,1'-bis(diphenylphosphino)ferrocene] dichloropalladium
Pd(PPh$_3$)$_4$ or Tetrakis refers to tetrakis(triphenylphosphine) palladium (0)
Pinacol diborane refers to 4,4,4',4',5,5,5',5'-octamethyl-2,2'-bi-1,3,2-dioxaborolane
r.t. refers to room temperature
Rt refers to retention time
SiO$_2$ refers to silicon dioxide
TEA refers to triethylamine
Tf refers to trifluoromethanesulfonyl
TFA refers to trifluoroacetic acid
THF refers to tetrahydrofuran
TLC/tlc refers to thin layer chromatography
$^1$H NMR spectra were recorded using a Bruker DPX 400 MHz, referenced to tetramethylsilane.

Mass spectra were recorded on a SHIMADZU LCMS 2010 EV Spectrometer using Positive/negative electrospray. Sample preparation was done in 100% methanol and the samples were injected via direct injection port Silica chromatography techniques include either automated (Flashmaster, Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance compound Y (EP 0 123 456), this means that the compound may be prepared as described in the named reference.

The names of the above mentioned Examples have been obtained using the compound naming programme "ACD Name Pro 6.02".

General HPLC Method:

HPLC was carried out using X-Bridge C18 250×4.6 mm, 5 micron at 267 nm. Column flow was 1 mL/min and solvents used were 0.1% TFA in water HPLC grade (A) and 0.1% TFA in MeCN Gradient grade (B), with an injection volume of 10 µL. Sample preparation in 250 ppm in Water:MeCN.

Method is as described below.

| Time (min) | A | B % |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

General LC-MS Methods:
Method-A

LC-MS was carried out using X-bridge C18 150×4.6 mm, 5 micron column. The UV detection was done at wavelength of maximum absorption (mentioned on individual spectra). The mass spectra were recorded on a SHIMADZU LCMS 2010EV Spectrometer using Positive/negative electro spray. Column flow was 1 mL/min and solvents used were 0.1% formic acid in HPLC grade water (A) and 0.1% formic acid in MeCN HPLC grade (B), with an injection volume of 10 µL. Sample preparation was at 250 ppm in MeCN+water.

Method is as described below.

| Time (min) | A | B % |
|---|---|---|
| 0.01 | 90 | 10 |
| 5.00 | 10 | 90 |
| 6.00 | 0 | 100 |
| 10.00 | 0 | 100 |
| 10.01 | 90 | 10 |
| 12.00 | 90 | 10 |

Method-B

LC-MS was carried out using X-bridge C18 150×4.6 mm, 5 micron column. The UV detection was done at wavelength of maximum absorption (mentioned on individual spectra). The mass spectra were recorded on a SHIMADZU LCMS 2010 EV Spectrometer using Positive/negative electro spray. Column flow was 1 mL/min and solvents used were 0.05% Ammonium Acetate in HPLC grade water (A) and 0.05% Ammonium acetate in Methanol HPLC grade (B), with an injection volume of 10 µL. Sample preparation was at 250 ppm in MeOH+ water.

Method is as described below.

| Time (min) | A | B % |
|---|---|---|
| 0.01 | 90 | 10 |
| 5.00 | 10 | 90 |
| 6.00 | 0 | 100 |
| 10.00 | 0 | 100 |
| 10.01 | 90 | 10 |
| 12.00 | 90 | 10 |

Method C

LC/MS (Aglient) was conducted on a HALO C18 column (50 mm×4.6 mm i.d. 2.7 µm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1 min 5% B, 1-2.01 min 95% B, 2.01-2.5 min 5% B at a flow rate of 1.8 ml/min. The UV detection was a summed signal at wavelength: 214 nm and 254 nm. MS: Ion Source: ESI; Drying Gas Flow: 10 L/min; Nebulizer Pressure: 45 psi; Drying Gas Temperature: 330° C.; Capillary Voltage: 4000V.

Preparative HPLC Method Used for the Purification of Compound Example 5:

Preparative HPLC was carried out on Waters Delta 600 using Gemini C18 150×21.2 mm, 5 micron column with the UV detection at 251 nm on a UV detector. Column flow was 21 mL/min. and solvents used were 0.1% TFA in water HPLC grade (A) and 0.1% TFA in Acetonitrile HPLC grade (B). Sample was prepared in 1:1 Water & Acetonitrile.

Method is as described below.

| Time (min) | B % |
|---|---|
| 0.01 | 25 |
| 5.5 | 55 |
| 5.51 | 100 |
| 9.0 | 100 |

-continued

| Time (min) | B % |
|---|---|
| 9.01 | 25 |
| 11 | 25 |

Preparative HPLC Method Used for the Purification of Compound Example 6:

Preparative HPLC was carried out using ACE C$_{18}$ 250× 21.2 mm, 5 micron column with the UV detection at 249 nm on a PDA detector. Column flow was 21 mL/min. and solvents used were 0.1% TFA in water HPLC grade (A) and 0.1% TFA in MeCN Gradient grade (B). Sample was prepared in a mixture of water and acetonitrile.

Method is as described below.

| Time (min) | B % |
|---|---|
| 0.01 | 30 |
| 7.00 | 50 |
| 8.00 | 100 |
| 12.00 | 100 |
| 12.01 | 30 |
| 14.00 | 30 |

Other compounds purified by preparative HPLC were purified by methods similar to those described above for examples 5 and 6

Intermediate 1: 1,1-dimethylethyl 7-(4,4,5,5-tetramethyl-1,3,2-dioxaborolan-2-yl)-1,2,4,5-tetrahydro-3H-3-benzazepine-3-carboxylate

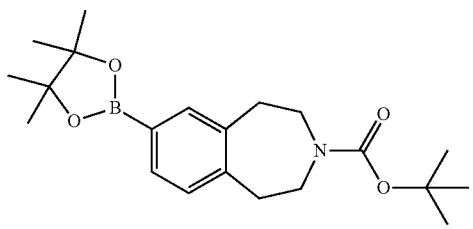 [SMILES: CC(C)(C)OC(=O)N1CCc2ccc(B3OC(C)(C)C(C)(C)O3)cc2CC1]

To a degassed mixture of 1,1-dimethylethyl 7-{[(trifluoromethyl)sulfonyl]oxy}-1,2,4,5-tetrahydro-3H-3-benzazepine-3-carboxylate (9.9 g) (which can be prepared according to J. Med Chem. 2007, 50(21) 5076-5089), 4,4,4',4',5,5,5',5'-octamethyl-2,2'-bi-1,3,2-dioxaborolane (7.6 g), potassium acetate (7.3 g) and dppf (0.833 g) in dioxane (165 ml) was added PdCl$_2$dppf.CH$_2$Cl$_2$ (1.2 g). The reaction mixture was again degassed with nitrogen/vacuum cycles. This was heated at 100° C. for 18 h. It was diluted with ethyl acetate and filtered through celite. The filtrate was concentrated to yield a crude product. This was purified by column chromatography eluting with a 0-6% gradient of ethyl acetate in hexane to give the title compound as a white solid (6.2 g)

LCMS (Method B): Rt=8.00 min, [MH]+−100=274 (loss of BOC group as artefact of the mass spectroscopy conditions)

Intermediate 18, 2-bromo-6-methyl-3-pyridinol

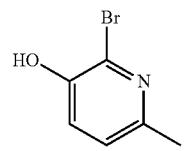

To a solution of 5-hydroxy-2-methylpyridine (Commercial, Aldrich, 44.5 g) in pyridine (400 ml) is added dropwise over 30 min at room temperature a solution of bromine (71.64 g) in pyridine (550 ml). The reaction mixture was stirred for an additional 1.5 h. The reaction mixture was poured into water (4 liters), stirred for a few minutes and extracted with diethyl ether (4×300 ml). The combined organics were dried over sodium sulphate and concentrated in vacuo to give a brown solid that was purified through silica using a 0-30% ethyl acetate in hexane system, to give the title compound as a beige solid, 37 g.

NMR $^1$H NMR (400 MHz, DMSO-d6) δ ppm 10.43 (1H, s, OH), 7.16 ppm (1H, d, CH), 7.06 (1H, d, CH), 2.31 (3H, s, CH3)

Intermediate 19, (4-ethyl-2-pyridinyl)methanol

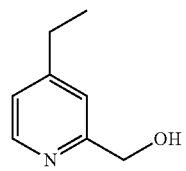

A solution of 4-ethylpyridine (Commercial, e.g. Sigma-Aldrich) (10.7 g), ammonium peroxydisulfate (45.6 g) and concentrated sulphuric acid (4.5 ml) in methanol (150 ml)/water (70 ml) was refluxed for 24 h. The reaction mixture was slowly added onto aqueous sodium bicarbonate and extracted with chloroform (4×500 ml). This was dried over sodium sulphate, concentrated in vacuo and purified through silica using 0-60% ethyl acetate in hexane to give the title compound, 1.16 g Mass Spec: [MH]+=138.0

Intermediate 20, 2-bromo-4-(ethyloxy)phenol

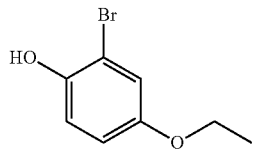

To a solution of 4-(ethyloxy)phenol (Commercial eg Aldrich) (1.0 g) in chloroform (5 ml) cooled to 0° C. was added bromine (1.26 g) dropwise over 20 min. The resulting mixture was stirred at 25 C for 2 h, before washing sequentially with aqueous sodium bicarbonate, and brine. The organics were dried over sodium sulphate, filtered and concentrated in vacuo to yield the title compound, 1.8 g LCMS (Method A): Rt=6.52 min, [MH]+=215, 217

Intermediate 65,
3-bromo-4-hydroxy-N-methylbenzamide

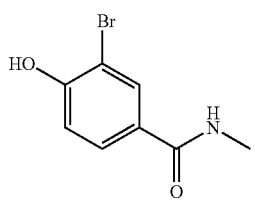

To a stirred solution of 3-bromo-4-hydroxybenzoic acid (Commercial eg Aldrich) (2.0 g), EDC (2.65 g), HOBT (1.41 g) and TEA (6.2 ml) in DCM (60 ml) was added methylamine hydrochloride (1.87 g). This was stirred at 25-30 C for 16 h. The solvent was removed under reduced pressure. The residue was dissolved in water and extracted with ethyl acetate. The organics were dried (sodium sulphate) and concentrated in vacuo to yield the title compound, 0.57 g LCMS (Method B): Rt=4.76 min Prepared similarly using a different amine was intermediate 66.

| Intermediate | Amine | Amount | Characterisation |
|---|---|---|---|
| 66 3-bromo-4-hydroxy-N,N-dimethylbenzamide | Dimethylamine, hydrochloride | 0.52 g | LCMS (Method B): Rt = 5.21 min, [MH]+ = 244, 266 |

Intermediate 67, 3-bromo-4-hydroxybenzamide

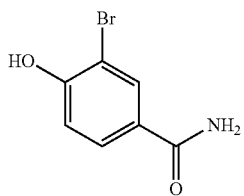 [SMILES: NC(=O)c1ccc(O)c(Br)c1]

To a stirred solution of 3-bromo-4-hydroxybenzoic acid (0.5 g) and DMF (0.1 ml) in DCM (10 ml) was added dropwise oxalyl chloride (0.6 ml). After stirring for 2 h, ammonia gas was purged through. After completion of reaction by tlc, the solvent was removed under reduced pressure. The residue was dissolved in water and extracted with ethyl acetate. The organics were dried over sodium sulphate and concentrated in vacuo to yield the title compound, 0.18 g LCMS (Method A): Rt=4.33 min, [MH]+=216, 218

Intermediate 68 1,2-bis(methyloxy)-4-{[(methyloxy)methyl]oxy}benzene

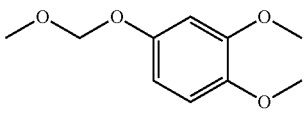

To a stirred solution of 3,4-bis(methyloxy)phenol (Commercial eg Alfa Aesar) (1.0 g) and DIPEA (2.28 ml) in DCM (15 ml) was added chloromethyl methyl ether (0.74 ml) at 0 C. After stirring at 25-30 C for 17 h, the reaction was washed with dilute hydrochloric acid and saturated aqueous sodium bicarbonate. This was dried over sodium sulphate and purified through silica eluting with 0-5% ethyl acetate in hexane, to give the title compound, 0.80 g LCMS (Method A): Rt=5.99 min, [MH]+=199

Intermediate 69 2-bromo-3,4-bis(methyloxy)-1-{[(methyloxy)methyl]oxy}benzene

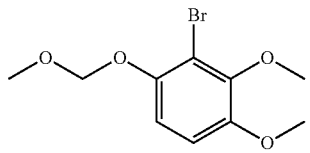

To a stirred solution of 1,2-bis(methyloxy)-4-{[(methyloxy)methyl]oxy}benzene (4.0 g) and TMEDA (3.93 ml) in dry diethyl ether (50 ml) was added tert-butyllithium (1.7M in pentane, 23.76 ml) at −70 C. The reaction was stirred at this temperature for 1 h before adding bromine (0.15 ml). This was allowed to stir at 0 C for 3 h. The reaction was quenched by addition of 20% aqueous sodium dithionite and extracted with ethyl acetate. The organics were washed with dilute hydrochloric acid, aqueous sodium bicarbonate, brine and dried over sodium sulphate to yield a crude product. This was purified through silica, eluting with 0-10% ethyl acetate in hexane to give the title compound, 1.4 g Mass Spec: [MH]+=277, 279

Intermediate 70, 2-bromo-3,4-bis(methyloxy)phenol

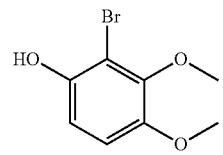

To a stirred solution of 2-bromo-3,4-bis(methyloxy)-1-{[(methyloxy)methyl]oxy}benzenein methanol (10 ml) was added hydrochloric acid (12M, 0.12 ml) at 25 C. The reaction mixture was stirred at 40 C for 5 h. The reaction mixture was partitioned between ethyl acetate and saturated aqueous sodium bicarbonate. The organics were washed with brine, dried over sodium sulphate and concentrated in vacuo. The crude product was purified through silica eluting with 0-4% ethyl acetate in hexane, to give the title compound, 0.65 g LCMS (Method B): Rt=5.58 min, [MH]+=233

Intermediate 2: 2-bromo-3-{[(4-methyl-2-pyridinyl)methyl]oxy}pyridine

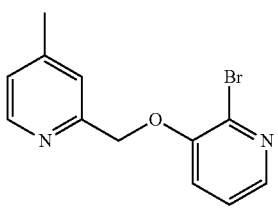 [SMILES: Cc1ccnc(COc2cccnc2Br)c1]

A mixture of 2-bromo-3-pyridinol (commercially available, e.g. from Aldrich) (2.9 g) and potassium carbonate (6.94 g) in DMF (25 ml) was stirred for 20 min before adding 2-(chloromethyl)-4-methylpyridine hydrochloride (for preparation see WO 2008/141011) (3 g). This was stirred at room temperature overnight. The reaction mixture was poured into ice/water and the solid formed was collected by filtration, washed with hexane and dried to give the title compound, 2.87 g (61%).

LCMS (Method A): Rt=4.27 min, [MH]+=279, 281.

The following intermediates were similarly prepared:

| Intermediate | Alkylating agent | Phenol | Amount | Characterisation |
|---|---|---|---|---|
| 3<br>2-({[2-bromo-3-(methyloxy)phenyl]oxy}methyl)-4-methylpyridine | 2-(chloromethyl)-4-methylpyridine, hydrochloride | (structure)<br>Preparation: J. Organic Chem. 2003, 68 (4) 1401-1408 | 1.9 g (39%) | LCMS (Method A): Rt = 5.16 min, [MH]+ = 308, 310 |
| 4<br>2-({[2-bromo-5-(methyloxy)phenyl]oxy}methyl)-4-methylpyridine | 2-(chloromethyl)-4-methylpyridine, hydrochloride | (structure)<br>Preparation: Synthetic Communications, 2007, 37 (2) 323-328 | 3 g (59%) | LCMS (Method A): Rt = 5.71 min, [MH]+ = 308, 310 |
| 5<br>1-(3-bromo-4-{[(4-methyl-2-pyridinyl)methyl]oxy}phenyl)ethanone | 2-(chloromethyl)-4-methylpyridine, hydrochloride | (structure)<br>Preparation: WO 2010/102154 | 2.6 g (49%) | LCMS (Method A): Rt = 5.29 min, [MH]+ = 320, 322 |
| 6<br>2-{[(2-bromo-4-fluorophenyl)oxy]methyl}-4-methylpyridine | 2-(chloromethyl)-4-methylpyridine, hydrochloride | (structure)<br>Commercial (Aldrich) | 1.3 g (81%) | LCMS (Method B): Rt = 7.39 min, [MH]+ = 296, 298 |
| 7<br>1-{3-bromo-4-[(2-pyrazinylmethyl)oxy]phenyl}ethanone | 2-(chloromethyl) pyrazine (Preparation WO 2010/132615 | (structure)<br>Preparation: WO 2010/102154 | *3.1 g (35%) | LCMS (Method B): Rt = 5.29 min, [MH]+ = 307, 309 |

-continued

| Intermediate | Alkylating agent | Phenol | Amount | Characterisation |
|---|---|---|---|---|
| 8<br>2-{[(2-bromophenyl)oxy]-methyl}-4-(methyloxy)pyridine | 2-(chloromethyl)-4-(methyloxy)-pyridine, hydrochloride<br>Commercial eg ABCR GmbH | 2-bromophenol<br>Commercial eg Aldrich | 3.0 g<br>*(99%) | LCMS (Method A):<br>Rt = 4.53 min, [MH]+ = 294, 296 |
| 9<br>1-{3-bromo-4-[(2-pyridinylmethyl)oxy]-phenyl}ethanone | 2-(Bromomethyl) pyridine hydrobromide<br>Commercial (Aldrich) | 3-bromo-4-hydroxyacetophenone<br>Preparation: WO 2010/102154 | #11.6 g<br>(74%) | HPLC: Rt = 10.31 min.<br>Mass Spec: [MH]+ = 305.9 |
| 21<br>2-bromo-6-(1,1-dimethylethyl)-3-{[(4-methyl-2-pyridinyl)methyl]oxy}-pyridine | 2-(chloromethyl)-4-methylpyridine, hydrochloride | 2-bromo-6-tert-butyl-3-hydroxypyridine<br>Preparation: Intermediate 63 | 0.23 g | Mass Spec: [MH]+ = 334.9 |
| 22<br>2-({[2-bromo-4-(methyloxy)phenyl]oxy}-methyl)pyridine | 2-(Bromomethyl) pyridine hydrobromide<br>Commercial (Aldrich) | 2-bromo-4-methoxyphenol<br>Commercial eg TCI (Europe) | #10.38 g | LCMS (Method A):<br>Rt = 7.86 min. [MH]+ = 294, 296 |
| 23<br>2-{[(2-bromo-6-methyl-3-pyridinyl)oxy]methyl}-pyrazine | 2-(chloromethyl) pyrazine | 2-bromo-3-hydroxy-6-methylpyridine<br>Preparation: Intermediate 18 | *1.19 g | HPLC: Rt = 8.66 min. |
| 24<br>2-({[2-bromo-4-(methyloxy)phenyl]oxy}-methyl)pyrazine | 2-(chloromethyl) pyrazine | 2-bromo-4-methoxyphenol<br>Commercial eg Apollo Scientific Ltd. | *2.3 g | HPLC: Rt = 9.54 min. |
| 25<br>2-bromo-6-methyl-3-{[(4-methyl-2-pyridinyl)methyl]oxy}-pyridine | 2-(chloromethyl)-4-methylpyridine, hydrochloride | 2-bromo-3-hydroxy-6-methylpyridine | 11.3 g | Mass Spec: [MH]+ = 292.9, 295<br>LCMS (Method):<br>Rt = 6.53 min. [MH]+ = 293, 295 |

-continued

| Intermediate | Alkylating agent | Phenol | Amount | Characterisation |
|---|---|---|---|---|
| 26<br>2-({[2-bromo-4-(methyloxy)phenyl]oxy}-methyl)-4-(methyloxy)pyridine | 2-(chloromethyl)-4-(methyloxy)-pyridine<br>Commercial eg ChemBridge | 2-bromo-4-methoxyphenol | 0.886 g | Mass Spec: [MH]+ = 323.9 |
| 27<br>2-({[2-bromo-4-methyloxy)phenyl]oxy}-methyl)-4-methylpyridine | 2-(chloromethyl)-4-methylpyridine hydrochloride | 2-bromo-4-methoxyphenol | 0.68 g | Mass Spec: [MH]+ = 307.9 |
| 28<br>1-[3-bromo-4-({[4-(methyloxy)-2-pyridinyl]methyl}oxy)-phenyl]ethanone | 2-(chloromethyl)-4-(methyloxy)-pyridine | 2-bromo-4-methoxyphenol | #0.35 g | Mass Spec: [MH]+ = 335.9 |
| 29<br>2-{[(2-bromo-4-methylphenyl)oxy]-methyl}-4-methylpyridine | 2-(chloromethyl)-4-methylpyridine, hydrochloride | 2-bromo-4-methylphenol<br>Commercial e.g. Aldrich | 1.0 g | LCMS (Method B): Rt = 7.64 min, [MH]+ = 292, 294 |
| 30<br>2-({[2-bromo-4-(ethyloxy)phenyl]oxy}-methyl)-4-methylpyridine | 2-(chloromethyl)-4-methylpyridine, hydrochloride | 2-bromo-4-ethoxyphenol<br>Preparation: WO2008079610 | 1.1 g | LCMS (Method A): Rt = 7.59 min, [MH]+ = 322, 324 |
| 31<br>2-({[2-bromo-4-(trifluoromethyl)phenyl]-oxy}methyl)-4-methylpyridine | 2-(chloromethyl)-4-methylpyridine, hydrochloride | 2-bromo-4-(trifluoromethyl)phenol<br>Commercial eg Fluorochem | 1.3 g | LCMS (Method B): Rt = 7.64 min, [MH]+ = 346, 348 |
| 32<br>3-bromo-4-{[(4-methyl-2-pyridinyl)methyl]oxy}-benzonitrile | 2-(chloromethyl)-4-methylpyridine, hydrochloride | 3-bromo-4-hydroxybenzonitrile<br>Commercial eg Aldrich | 1.1 g | LCMS (Method B): Rt = 6.95 min, [MH]+ = 303, 305 |

-continued

| Intermediate | Alkylating agent | Phenol | Amount | Characterisation |
|---|---|---|---|---|
| 33<br>2-({[2-bromo-4-(1,1-dimethylethyl)phenyl]oxy}-methyl)-4-methylpyridine | 2-(chloromethyl)-4-methylpyridine, hydrochloride | 4-bromo-2-tert-butylphenol<br>Commercial eg Apollo Scientific Ltd | 0.77 g | Mass Spec: [MH]+ = 333.9 |
| 71<br>3-bromo-N-methyl-4-{[(4-methyl-2-pyridinyl)methyl]oxy}-benzamide | 2-(chloromethyl)-4-methylpyridine, hydrochloride | Intermediate 65 | 0.54 g | LCMS (Method B): Rt = 6.44 min, [MH]+ = 335, 337 |
| 72<br>3-bromo-4-{[(4-methyl-2-pyridinyl)methyl]oxy}-benzamide | 2-(chloromethyl)-4-methylpyridine, hydrochloride | Intermediate 67 | 0.49 g | LCMS (Method A): Rt = 6.20 min, [MH]+ = 321, 323 |
| 73<br>3-bromo-N,N-dimethyl-4-{[(4-methyl-2-pyridinyl)methyl]oxy}-benzamide | 2-(chloromethyl)-4-methylpyridine, hydrochloride | Intermediate 66 | 0.51 g | LCMS (Method B): Rt = 6.54 min, [MH]+ = 349, 351 |
| 74<br>2-({[2-bromo-3,4-bis(methyloxy)phenyl]oxy}-methyl)-4-methylpyridine | 2-(chloromethyl)-4-methylpyridine, hydrochloride | Intermediate 70 | 0.547 g | LCMS (Method B): Rt = 5.07 min, [MH]+ = 338, 340 |
| 75<br>2-{[(2-bromo-4-chlorophenyl)oxy]-methyl}-4-methylpyridine | 2-(chloromethyl)-4-methylpyridine, hydrochloride | 2-bromo-4-chlorophenol<br>Commercial eg Aldrich | 0.63 g | LCMS (Method A): Rt = 7.75 min, [MH]+ = 313.85 |

| Intermediate | Alkylating agent | Phenol | Amount | Characterisation |
|---|---|---|---|---|
| 85 2-bromo-6-methyl-3-({[4-(methyloxy)-2-pyridinyl]methyl}oxy)-pyridine | 2-(chloromethyl)-4-(methyloxy)-pyridine | (Br, HO, N, Me pyridine structure) | 1.80 g | $^1$H NMR (400 MHz, DMSO-d6) δ ppm 8.40 (1H, d, CH), 7.52 (1H, d, CH), 7.24 (1H, d, CH), 7.14 (1H, d, CH), 6.96 (1H, s), 6.95 (1H, m, 1H), 5.23 (2H, s, CH$_2$), 3.85 (3H, s, OMe), 2.39 (3H, s, Me) |
| 86 2-bromo-6-chloro-3-{[(4-methyl-2-pyridinyl)methyl]oxy}-pyridine | 2-(chloromethyl)-4-methylpyridine, hydrochloride | (Br, HO, N, Cl pyridine structure) Commercial e.g. Combi-Blocks Inc. | 0.21 g | LCMS (Method A): Rt = 6.92 min, [MH]+ = 314.85 |
| 87 2-({[2-bromo-3-(methyloxy)phenyl]oxy}-methyl)pyrazine | 2-(chloromethyl) pyrazine | (Br, HO, OMe phenyl structure) | 2.10 g | LCMS (Method C): Rt = 1.51 min, [MH]+ = 295, 296.9 |

*Intermediate 8 was purified by column chromatography, eluting with 0-20% ethyl acetate in hexane
*Purified through silica eluting with a gradient of ethyl acetate in hexane, increasing ethyl acetate until product eluted
Work up by partitioning between ethyl acetate and aqueous ammonium chloride. Organics dried with sodium sulphate and concentrated in vacuo to yield the title compound.

Intermediate 34, 1-(3-bromo-4-{[(4-chloro-2-pyridinyl)methyl]oxy}phenyl)ethanone

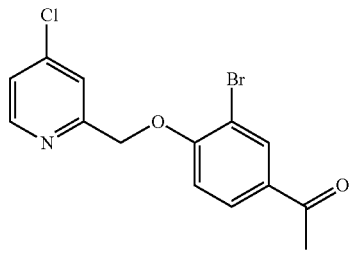 [SMILES: CC(=O)c1ccc(OCc2cc(Cl)ccn2)c(Br)c1]

To a stirred solution of (4-chloro-2-pyridinyl)methanol (Commercial eg Aldrich) (0.2 g) in THF (5 ml) were added 1-(3-bromo-4-hydroxyphenyl)ethanone (0.3 g) and triphenylphosphine (0.547 g). This was stirred for 10 min before cooling and adding slowly DEAD (0.363 g). This was stirred for 16 h. The reaction mixture was partitioned between water and ethyl acetate. The aqueous was reextracted with ethyl acetate and the combined organics were washed with brine, dried over sodium sulfate and concentrated in vacuo. This was purified through silica eluting with 0-35% ethyl acetate in hexane to give the title compound, 0.30 g Mass Spec: [MH]+=340, 342

Prepared similarly were:

| Intermediate | Alcohol | Phenol | Amount | Characterisation |
|---|---|---|---|---|
| 35 1-(3-bromo-4-{[(4-ethyl-2-pyridinyl)methyl]oxy}-phenyl)ethanone | (4-ethyl-2-pyridinyl)-methanol | (Br, HO, phenyl ethanone structure) | 0.45 g | Mass Spec: [MH]+ = 333.9 |

-continued

| Intermediate | Alcohol | Phenol | Amount | Characterisation |
|---|---|---|---|---|
| 36 2-bromo-3-{[(4-ethyl-2-pyridinyl)methyl]oxy}-6-methylpyridine | (4-ethyl-2-pyridinyl)-methanol | (2-bromo-6-methylpyridin-3-ol structure) | 4.0 g | LCMS (Method B): Rt = 5.08 min, [MH]+ = 307, 309 |

Intermediate 10: 1,1-dimethylethyl 7-(3-{[(4-methyl-2-pyridinyl)methyl]oxy}-2-pyridinyl)-1,2,4,5-tetrahydro-3H-3-benzazepine-3-carboxylate

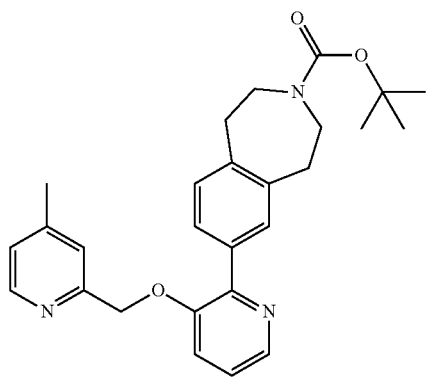 [SMILES: Cc1ccnc(COc2cccnc2-c2ccc3c(c2)CCN(C(=O)OC(C)(C)C)CC3)c1]

To a degassed mixture of 2-bromo-3-{[(4-methyl-2-pyridinyl)methyl]oxy}pyridine (2.83 g), 1,1-dimethylethyl 7-(4,4,5,5-tetramethyl-1,3,2-dioxaborolan-2-yl)-1,2,4,5-tetrahydro-3H-3-benzazepine-3-carboxylate (4.54 g) and cesium carbonate (9.9 g) in dioxane:water (4:1, 40 ml) was added PdCl$_2$.dppf (0.828 g). The reaction mixture was heated at 120° C. overnight. The reaction mixture was added to water and extraction was carried out with ethyl acetate. The organic layer was dried over sodium sulphate and the filtrate was concentrated in vacuo. The crude product was purified through silica, eluting with 0-40% ethyl acetate in hexane. Appropriate fractions were concentrated in vacuo to yield the title compound, 3.8 g (84%).

LCMS (Method A): Rt=5.70 min, [MH]+=446

The following intermediates were similarly prepared:

| Intermediate | Aromatic bromide | Purification | Amount | Characterisation |
|---|---|---|---|---|
| 11 1,1-dimethylethyl 7-(2-(methyloxy)-6-{[(4-methyl-2-pyridinyl)methyl]oxy}-phenyl)-1,2,4,5-tetrahydro-3H-3-benzazepine-3-carboxylate | (structure) | 0-15% ethyl acetate in hexane | 2.57 g (89%) | LCMS (Method A): Rt = 6.76 min, [MH]+ = 475 |
| 12 1,1-dimethylethyl 7-(4-(methyloxy)-2-{[(4-methyl-2-pyridinyl)methyl]oxy}-phenyl)-1,2,4,5-tetrahydro-3H-3-benzazepine-3-carboxylate | (structure) | 0-20% ethyl acetate in hexane | 4.8 g (quant.) | LCMS (Method A): Rt = 7.13 min, [MH]+ = 475 |
| 13 1,1-dimethylethyl 7-(5-acetyl-2-{[(4-methyl-2-pyridinyl)methyl]oxy}-phenyl)-1,2,4,5-tetrahydro-3H-3-benzazepine-3-carboxylate | (structure) | 0-20% ethyl acetate in hexane | 3.0 g (77%) | LCMS (Method A): Rt = 6.77 min, [MH]+ = 487 |

| Intermediate | Aromatic bromide | Purification | Amount | Characterisation |
|---|---|---|---|---|
| 14 1,1-dimethylethyl 7-[2-({[4-(methyloxy)-2-pyridinyl]methyl}oxy)-phenyl]-1,2,4,5-tetrahydro-3H-3-benzazepine-3-carboxylate | | 0-20% ethyl acetate in hexane | 3.1 g (71%) | LCMS (Method A): Rt = 6.23 min, [MH]+ = 461 |
| 37 1,1-dimethylethyl 7-(6-(1,1-dimethylethyl)-3-{[(4-methyl-2-pyridinyl)methyl]oxy}-2-pyridinyl)-1,2,4,5-tetrahydro-3H-3-benzazepine-3-carboxylate | | 0-15% ethyl acetate in hexane | 3.7 g | Mass Spec: [MH]+ = 502 |
| 38 1,1-dimethylethyl 7-(6-methyl-3-{[(4-methyl-2-pyridinyl)methyl]oxy}-2-pyridinyl)-1,2,4,5-tetrahydro-3H-3-benzazepine-3-carboxylate | | 0-40% EA/hexane | 15 g | Mass Spec: [MH]+ = 460.2 LCMS (Method A): Rt = 7.40 min, [MH]+ = 460 |
| 39 1,1-dimethylethyl 7-(3-{[(4-ethyl-2-pyridinyl)methyl]oxy}-6-methyl-2-pyridinyl)-1,2,4,5-tetrahydro-3H-3-benzazepine-3-carboxylate | | 0-20% EA/hexane | 4.3 g | Mass Spec: [MH]+ = 474 |
| 40 1,1-dimethylethyl 7-(5-methyl-2-{[(4-methyl-2-pyridinyl)methyl]oxy}-phenyl)-1,2,4,5-tetrahydro-3H-3-benzazepine-3-carboxylate | | 0-15% EA/hexane | 0.271 g | LCMS (Method A): Rt = 8.21 min, [MH]+ = 459.15 |
| 41 1,1-dimethylethyl 7-(5-(ethyloxy)-2-{[(4-methyl-2-pyridinyl)methyl]oxy}-phenyl)-1,2,4,5-tetrahydro-3H-3-benzazepine-3-carboxylate | | 0-15% EA/hexane | 0.241 g | LCMS (Method B): Rt = 8.06 min, [MH]+ = 489.25 |
| 42 1,1-dimethylethyl 7-(5-fluoro-2-{[(4-methyl-2-pyridinyl)methyl]oxy}-phenyl)-1,2,4,5-tetrahydro-3H-3-benzazepine-3-carboxylate | | 0-25% EA/hexane | 0.304 g | LCMS (Method A): Rt = 7.97 min, [MH]+ = 463.25 |

| Intermediate | Aromatic bromide | Purification | Amount | Characterisation |
|---|---|---|---|---|
| 43<br>1,1-dimethylethyl 7-(5-cyano-2-{[(4-methyl-2-pyridinyl)methyl]oxy}-phenyl)-1,2,4,5-tetrahydro-3H-3-benzazepine-3-carboxylate | | 0-30% EA/hexanes | 0.24 g | LCMS (Method B): Rt = 7.60 min, [MH]+ = 470.2 |
| 44<br>1,1-dimethylethyl 7-(5-(1,1-dimethylethyl)-2-{[(4-methyl-2-pyridinyl)methyl]oxy}-phenyl)-1,2,4,5-tetrahydro-3H-3-benzazepine-3-carboxylate | | 0-37% EA/hexane | 0.296 g | LCMS (Method A): Rt = 8.53 min, [MH]+ = 501.3 |
| 45<br>1,1-dimethylethyl 7-[2-{[(4-methyl-2-pyridinyl)methyl]oxy}-5-(trifluoromethyl)-phenyl]-1,2,4,5-tetrahydro-3H-3-benzazepine-3-carboxylate | | 0-18% EA/hexane | 0.315 g | LCMS (Method A): Rt = 8.06 min, [MH]+ = 513.2 |
| 76<br>1,1-dimethylethyl 7-(5-[(methylamino)carbonyl]-2-{[(4-methyl-2-pyridinyl)methyl]oxy}-phenyl)-1,2,4,5-tetrahydro-3H-3-benzazepine-3-carboxylate | | 0-2% methanol in DCM | 0.28 g | LCMS (Method A): Rt = 9.03 min, [MH]+ = 502 |
| 77<br>1,1-dimethylethyl 7-(5-(aminocarbonyl)-2-{[(4-methyl-2-pyridinyl)methyl]oxy}-phenyl)-1,2,4,5-tetrahydro-3H-3-benzazepine-3-carboxylate | | 0-2% methanol in DCM | 0.297 g | LCMS (Method A): Rt = 7.13 min, [MH]+ = 488 |
| 78<br>1,1-dimethylethyl 7-(2,3-bis(methyloxy)-6-{[(4-methyl-2-pyridinyl)methyl]oxy}-phenyl)-1,2,4,5-tetrahydro-3H-3-benzazepine-3-carboxylate | | 0-20% EA/hexane | 0.225 g | LCMS (Method A): Rt = 6.59 min, [MH]+ = 505 |

| Intermediate | Aromatic bromide | Purification | Amount | Characterisation |
|---|---|---|---|---|
| 79<br>1,1-dimethylethyl 7-(5-chloro-2-{[(4-methyl-2-pyridinyl)methyl]oxy}-phenyl)-1,2,4,5-tetrahydro-3H-3-benzazepine-3-carboxylate | | 0-25% EA/ hexane | 0.24 g | LCMS (Method A): Rt = 8.17 min, [MH]+ = 479.15 |
| 88<br>1,1-dimethylethyl 7-(6-chloro-3-{[(4-methyl-2-pyridinyl)methyl]oxy}-2-pyridinyl)-1,2,4,5-tetrahydro-3H-3-benzazepine-3-carboxylate | | 0-25% EA/ hexane | 0.094 g | LCMS (Method B): Rt = 7.76 min, [MH]+ = 480.15 |
| 89<br>1,1-dimethylethyl 7-{2'-(methyloxy)-6'-[(2-pyrazinylmethyl)oxy]-4-biphenylyl}-1,2,4,5-tetrahydro-3H-3-benzazepine-3-carboxylate | | 25% EA/ hexane | 1.0 g | LCMS (Method C): Rt = 1.77 min, [MH]+ = 462.2 |

The following intermediate was prepared similarly using 1,1-dimethylethyl 7-(4,4,5,5-tetramethyl-1,3,2-dioxaborolan-2-yl)-3,4-dihydro-2(1H)-isoquinolinecarboxylate rather than 1,1-dimethylethyl 7-(4,4,5,5-tetramethyl-1,3,2-dioxaborolan-2-yl)-1,2,4,5-tetrahydro-3H-3-benzazepine-3-carboxylate

| Intermediate | Aromatic bromide | Purification | Amount | Characterisation |
|---|---|---|---|---|
| 90<br>1,1-dimethylethyl 7-(6-chloro-3-{[(4-methyl-2-pyridinyl)methyl]oxy}-2-pyridinyl)-3,4-dihydro-2(1H)-isoquinoline-carboxylate | | 0-35% EA/ hexane | 0.037 g | LCMS (Method B): Rt = 7.59 min, [MH]+ = 480.15 |

Intermediate 15: 1,1-dimethylethyl 7-(5-fluoro-2-{[(4-methyl-2-pyridinyl)methyl]oxy}phenyl)-3,4-dihydro-2(1H)-isoquinolinecarboxylate

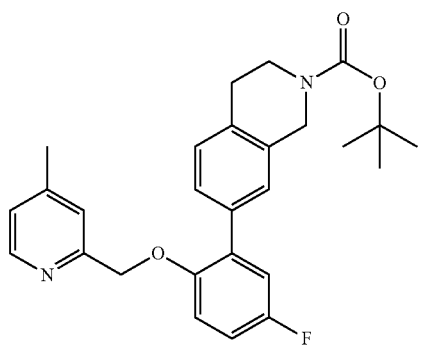 [SMILES: Cc1ccnc(COc2ccc(F)cc2-c2ccc3c(c2)CN(C(=O)OC(C)(C)C)CC3)c1]

To a degassed mixture 2-{[(2-bromo-4-fluorophenyl)oxy]methyl}-4-methylpyridine (0.09 g), 1,1-dimethylethyl 7-(4,4,5,5-tetramethyl-1,3,2-dioxaborolan-2-yl)-3,4-dihydro-2(1H)-isoquinolinecarboxylate (0.131 g) (for preparation see WO 2007/056710) and caesium carbonate (0.296 g) in dioxane:water (4:1, 5 ml) was added PdCl₂.dppf (0.025 g). The reaction mixture was heated at 120° C. overnight. The reaction mixture was added to water and extraction was carried out with ethyl acetate. The organic layer was dried over sodium sulphate and the filtrate was concentrated in vacuo. The crude product was purified through silica, eluting with 0-12% ethyl acetate in hexane. Appropriate fractions were concentrated in vacuo to yield the title compound, 0.169 g, quantitative yield.

LCMS (Method B): Rt=7.95 min, [MH]+=449

The following intermediates were similarly prepared:

| Intermediate | Aromatic bromide | Amount | Characterisation |
|---|---|---|---|
| 46<br>1,1-dimethylethyl 7-(5-methyl-2-{[(4-methyl-2-pyridinyl)methyl]oxy}-phenyl)-3,4-dihydro-2(1H)-isoquinolinecarboxylate | | 0.157 g | LCMS (Method A): Rt = 8.20 min, [MH]+ = 445.15 |
| 47<br>1,1-dimethylethyl 7-(5-(methyloxy)-2-{[(4-methyl-2-pyridinyl)methyl]oxy}-phenyl)-3,4-dihydro-2(1H)-isoquinolinecarboxylate | | 0.137 g | LCMS (Method A): Rt = 7.89 min, [MH]+ = 461.2 |
| 48<br>1,1-dimethylethyl 7-[2-{[(4-methyl-2-pyridinyl)methyl]oxy}-5-(trifluoromethyl)phenyl]-3,4-dihydro-2(1H)-isoquinolinecarboxylate | | 0.153 g | LCMS (Method B): Rt = 8.05 min, [MH]+ = 499.15 |
| 49<br>1,1-dimethylethyl 7-(2-(methyloxy)-6-{[(4-methyl-2-pyridinyl)methyl]oxy}-phenyl)-3,4-dihydro-2(1H)-isoquinolinecarboxylate | | 0.145 g | LCMS (Method A): Rt = 7.71 min, [MH]+ = 461 |
| 50<br>1,1-dimethylethyl 7-(5-cyano-2-{[(4-methyl-2-pyridinyl)methyl]oxy}-phenyl)-3,4-dihydro-2(1H)-isoquinolinecarboxylate | | 0.139 g | LCMS (Method A): Rt = 7.55 min, [MH]+ = 456.15 |
| 51<br>1,1-dimethylethyl 7-(5-(ethyloxy)-2-{[(4-methyl-2-pyridinyl)methyl]oxy}-phenyl)-3,4-dihydro-2(1H)-isoquinolinecarboxylate | | 0.128 g | LCMS (Method B): Rt = 8.05 min, [MH]+ = 475 |

-continued

| Intermediate | Aromatic bromide | Amount | Characterisation |
|---|---|---|---|
| 52<br>1,1-dimethylethyl 7-(5-(1,1-dimethylethyl)-2-{[(4-methyl-2-pyridinyl)methyl]oxy}-phenyl)-3,4-dihydro-2(1H)-isoquinolinecarboxylate | | 0.13 g | LCMS (Method A):<br>Rt = 8.54 min,<br>[MH]+ = 487.2 |
| 80<br>1,1-dimethylethyl 7-(5-[(dimethylamino)carbonyl]-2-{[(4-methyl-2-pyridinyl)methyl]oxy}-phenyl)-3,4-dihydro-2(1H)-isoquinolinecarboxylate | | 0.21 g | LCMS (Method B):<br>Rt = 7.17 min,<br>[MH]+ = 502 |
| 81<br>1,1-dimethylethyl 7-(5-(aminocarbonyl)-2-{[(4-methyl-2-pyridinyl)methyl]oxy}-phenyl)-3,4-dihydro-2(1H)-isoquinolinecarboxylate | | 0.40 g | LCMS (Method A):<br>Rt = 5.30 min,<br>[MH]+ = 474 |
| 82<br>1,1-dimethylethyl 7-(2,3-bis(methyloxy)-6-{[(4-methyl-2-pyridinyl)methyl]oxy}-phenyl)-3,4-dihydro-2(1H)-isoquinolinecarboxylate | | 0.21 g | LCMS (Method A):<br>Rt = 6.40 min,<br>[MH]+ = 491 |
| 83<br>1,1-dimethylethyl 7-(5-chloro-2-{[(4-methyl-2-pyridinyl)methyl]oxy}-phenyl)-3,4-dihydro-2(1H)-isoquinolinecarboxylate | | 0.28 g | LCMS (Method B):<br>Rt = 8.10 min,<br>[MH]+ = 465.1 |

Intermediate 16: 1,1-dimethylethyl 7-{5-acetyl-2-[(2-pyrazinylmethyl)oxy]phenyl}-1,2,4,5-tetrahydro-3H-3-benzazepine-3-carboxylate

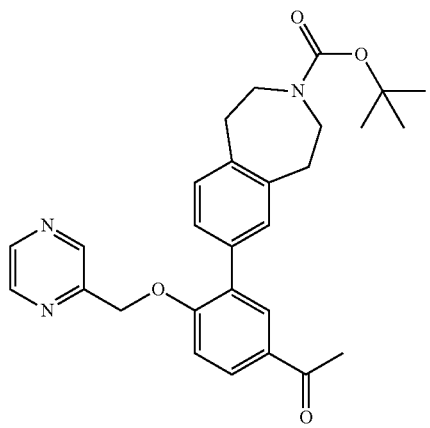 [SMILES: CC(=O)c1ccc(OCc2cnccn2)c(-c2ccc3c(c2)CCN(C(=O)OC(C)(C)C)CC3)c1]

To a stirred solution of 1-{3-bromo-4-[(2-pyrazinylmethyl)oxy]phenyl}ethanone (0.2 g) and 1,1-dimethylethyl 7-(4,4,5,5-tetramethyl-1,3,2-dioxaborolan-2-yl)-1,2,4,5-tetrahydro-3H-3-benzazepine-3-carboxylate (0.34 g) in DME (4 ml) was added aqueous sodium carbonate (2M, 0.98 ml). This was degassed with nitrogen for 15 min before adding Tetrakis (37 mg). The reaction was heated under reflux overnight. TLC indicated the reaction had gone to completion and so it was cooled, diluted with water and extracted with ethyl acetate. The combined organics were dried over sodium sulphate and concentrated in vacuo to yield a crude product which was purified by column chromatography, eluting with 0-18% ethyl acetate in hexane. The appropriate fractions were concentrated in vacuo to yield the title compound, 0.093 g, 30% yield.

Mass Spec.: [MH]+=474.2

Intermediate 17 was similarly prepared using different aromatic bromides:

| Intermediate | Aromatic bromide | Purification | Amount | Characterisation |
|---|---|---|---|---|
| 17 1,1-dimethylethyl 7-{5-acetyl-2-[(2-pyridinylmethyl)-oxy]phenyl}-1,2,4,5-tetrahydro-3H-3-benzazepine-3-carboxylate | | 0-18% ethyl acetate in hexane | 0.056 g (50.5%) | Mass Spec: [MH]+ = 473.2 |
| 53 1,1-dimethylethyl 7-{6-methyl-3-[(2-pyrazinylmethyl)-oxy]-2-pyridinyl}-1,2,4,5-tetrahydro-3H-3-benzazepine-3-carboxylate | | EA/hexane | 0.247 g | Mass Spec: [MH]+ = 447.2 |
| 54 1,1-dimethylethyl 7-{5-(methyloxy)-2-[(2-pyrazinylmethyl)-oxy]phenyl}-1,2,4,5-tetrahydro-3H-3-benzazepine-3-carboxylate | | EA/hexane | 0.193 g | Mass Spec: [MH]+ = 462.2 |
| 55 1,1-dimethylethyl 7-[5-(methyloxy)-2-({[4-(methyloxy)-2-pyridinyl]methyl}-oxy)phenyl]-1,2,4,5-tetrahydro-3H-3-benzazepine-3-carboxylate | | EA/hexane | 0.268 g | Mass Spec: [MH]+ = 491.3 |

-continued

| Intermediate | Aromatic bromide | Purification | Amount | Characterisation |
|---|---|---|---|---|
| 56 1,1-dimethylethyl 7-(5-(methyloxy)-2-{[(4-methyl-2-pyridinyl)methyl]oxy}phenyl)-1,2,4,5-tetrahydro-3H-3-benzazepine-3-carboxylate | | EA/hexane | 0.273 g | Mass Spec: [MH]+ = 475.3 |
| 57 1,1-dimethylethyl 7-[5-acetyl-2-({[4-(methyloxy)-2-pyridinyl]methyl}oxy)phenyl]-1,2,4,5-tetrahydro-3H-3-benzazepine-3-carboxylate | | EA/hexane | 0.291 | Mass Spec: [MH]+ = 503.2 |
| 58 1,1-dimethylethyl 7-(5-acetyl-2-{[(4-chloro-2-pyridinyl)methyl]oxy}phenyl)-1,2,4,5-tetrahydro-3H-3-benzazepine-3-carboxylate | | EA/hexane | 0.97 g | Mass Spec: [MH]+ = 507.2 |
| 59 1,1-dimethylethyl 7-(5-acetyl-2-{[(4-ethyl-2-pyridinyl)methyl]oxy}phenyl)-1,2,4,5-tetrahydro-3H-3-benzazepine-3-carboxylate | | 0-4% MeOH in DCM | 0.217 g | Mass Spec: [MH]+ = 501.2 |
| 91 1,1-dimethylethyl 7-[6-methyl-3-({[4-(methyloxy)-2-pyridinyl]methyl}oxy)-2-pyridinyl]-1,2,4,5-tetrahydro-3H-3-benzazepine-3-carboxylate | | EA/hexane | 0.283 g | Mass Spec: [MH]+ = 476.2 |

The following intermediate was prepared similarly using 1,1-dimethylethyl 7-(4,4,5,5-tetramethyl-1,3,2-dioxaborolan-2-yl)-3,4-dihydro-2(1H)-isoquinolinecarboxylate rather than 1,1-dimethylethyl 7-(4,4,5,5-tetramethyl-1,3,2-dioxaborolan-2-yl)-1,2,4,5-tetrahydro-3H-3-benzazepine-3-carboxylate

| 84 1,1-dimethylethyl 7-{5-acetyl-2-[(2-pyridinylmethyl)oxy]-phenyl}-3,4-dihydro-2(1H)-isoquinolinecarboxylate | 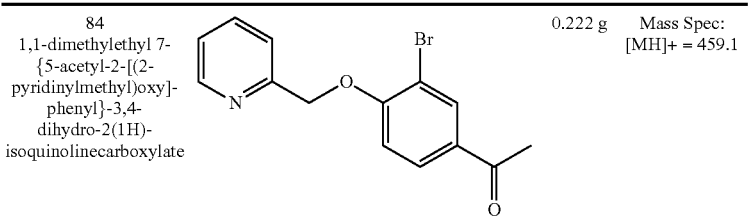 | 0.222 g | Mass Spec: [MH]+ = 459.1 |

The following intermediate was prepared similarly using 1,1-dimethylethyl 5-(4,4,5,5-tetramethyl-1,3,2-dioxaborolan-2-yl)-1,3-dihydro-2H-isoindole-2-carboxylate (Preparation e.g. WO2010145202) rather than 1,1-dimethylethyl 7-(4,4,5,5-tetramethyl-1,3,2-dioxaborolan-2-yl)-1,2,4,5-tetrahydro-3H-3-benzazepine-3-carboxylate

| 92 1,1-dimethylethyl 5-{5-acetyl-2-[(2-pyridinylmethyl)oxy]-phenyl}-1,3-dihydro-2H-isoindole-2-carboxylate | 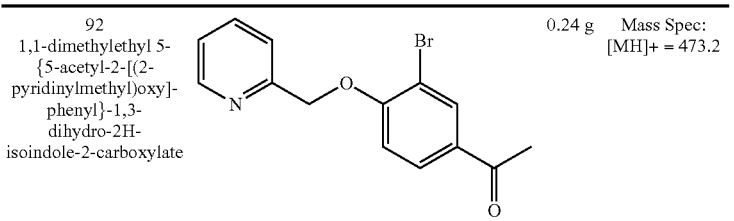 | 0.24 g | Mass Spec: [MH]+ = 473.2 |

The following intermediate was prepared similarly using 1,1-dimethylethyl 6-(4,4,5,5-tetramethyl-1,3,2-dioxaborolan-2-yl)-3,4-dihydro-2(1H)-isoquinolinecarboxylate (preparation e.g. WO2008079277) rather than 1,1-dimethylethyl 7-(4,4,5,5-tetramethyl-1,3,2-dioxaborolan-2-yl)-1,2,4,5-tetrahydro-3H-3-benzazepine-3-carboxylate

| 93 1,1-dimethylethyl 6-{5-acetyl-2-[(2-pyridinylmethyl)oxy]-phenyl}-3,4-dihydro-2(1H)-isoquinolinecarboxylate | 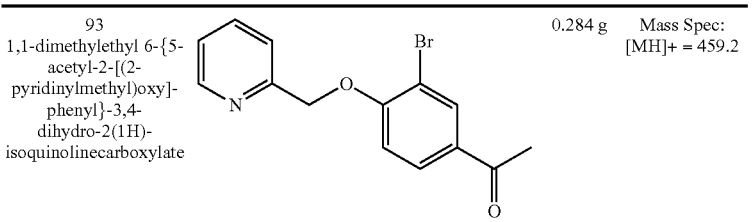 | 0.284 g | Mass Spec: [MH]+ = 459.2 |

Intermediate 60, 2-bromo-5-[(phenylmethyl)oxy]pyridine

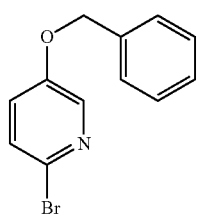 [SMILES: Brc1ccc(OCc2ccccc2)cn1]

To a stirred solution of 6-bromo-3-pyridinol (10 g, Commercial eg Apollo Scientific Ltd.) in DMF (100 ml) was added potassium carbonate (17.8 g). The reaction mixture was stirred for 15 min at 25-30 C before cooling to 15° C. To this was added slowly benzyl bromide (7.5 ml) and this was stirred at 25-30° C. for 48 h. The reaction mixture was poured into cold water and the solid was collected by filtration to give the title compound, 14.5 g Mass Spec: [MH]+=265.9

Intermediate 61, 2-(1,1-dimethylethyl)-5-[(phenylmethyl)oxy]pyridine

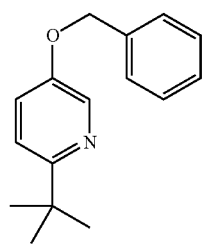 [SMILES: CC(C)(C)c1ccc(OCc2ccccc2)cn1]

To a stirred solution of copper (I) cyanide (18.31 g) in dry THF (400 ml) was added, at −78 C, tertbutylmagnesium chloride (1M in THF, 409 ml). The reaction mixture was stirred at this temperature for 15 min before slowly adding a solution of 2-bromo-5-[(phenylmethyl)oxy]pyridine (13.5 g) in THF. This was stirred for 2 h at −78 C before warming to 25-30 C and stirring for a further 20 h. The reaction mixture was poured into water and extracted with ethyl acetate. This was concentrated in vacuo and purified through silica, eluting with 0-2% ethyl acetate in hexane. Appropriate fractions were combined and concentrated in vacuo to yield the title compound, 6.3 g LCMS (Method B): Rt=5.61 min, [MH]+=242

Intermediate 62, 6-(1,1-dimethylethyl)-3-pyridinol

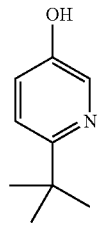

To a stirred solution of 2-(1,1-dimethylethyl)-5-[(phenylmethyl)oxy]pyridine, (5.3 g) in ethanol (150 ml) was added 20% Pd(OH)$_2$ (12.3 g) at 25-30 C. The above mixture was purged with hydrogen for 3 h until it had gone to completion by tlc. The reaction mixture was filtered through celite and the filtrate concentrated in vacuo and purified to give the title compound, 3.9 g LCMS (Method B): Rt=3.14 min, [MH]+=152

Intermediate 63, 2-bromo-6-(1,1-dimethylethyl)-3-pyridinol

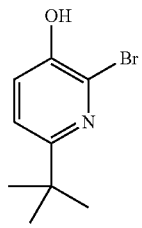

To a stirred solution of 6-(1,1-dimethylethyl)-3-pyridinol, (3.8 g) in pyridine (150 ml) was added bromine (1.29 ml), diluted in pyridine, dropwise at 20 C. The reaction mixture was allowed to stir at 25-30 C for 1 h. The reaction had gone to completion by tlc. It was poured into brine and extracted with ethyl acetate. The organics were dried over sodium sulphate and concentrated under reduced pressure. The crude material was subjected to flash chromatography using a 0-5% gradient of ethyl acetate in hexane to give the title compound, 2.9 g LCMS (Method B): Rt=6.16 min, [MH]+=229.9

Intermediate 64 1,1-dimethylethyl 7-[5-acetyl-2-({[4-(ethyloxy)-2-pyridinyl]methyl}oxy)phenyl]-1,2,4,5-tetrahydro-3H-3-benzazepine-3-carboxylate

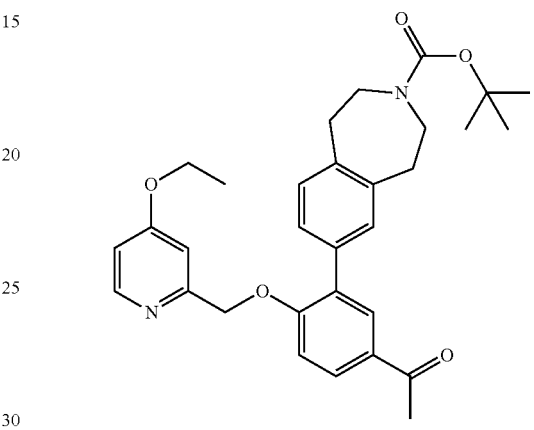

Potassium tert-butoxide (0.132 g) in ethanol (4 ml) was stirred for 15 min before adding 1,1-dimethylethyl 7-(5-acetyl-2-{[(4-chloro-2-pyridinyl)methyl]oxy}phenyl)-1,2,4,5-tetrahydro-3H-3-benzazepine-3-carboxylate, (0.4 g) and this was heated in a microwave at 110 C for 1.5 h. Water (20 ml) was added to the cooled mixture and this was extracted with DCM (2×30 ml). The combined organics were washed with brine, dried over sodium sulphate and concentrated in vacuo. The crude product was purified through silica eluting with 0-45% ethyl acetate in hexane to give the title compound, 0.16 g Mass Spec: [MH]+=517.3

Prepared similarly was Intermediate:

| Intermediate | Starting Materials | Amount | LCMS |
|---|---|---|---|
| 94 1,1-dimethylethyl 7-(5-acetyl-2-{[(4-{[2-(methyloxy)-ethyl]oxy}-2-pyridinyl)methyl]-oxy}phenyl)-1,2,4,5-tetrahydro-3H-3-benzazepine-3-carboxylate | and MeO(CH$_2$)$_2$OH | 0.045 g | Mass Spec: [MH]+ = 547.3 |

Example 1

7-(3-{[(4-methyl-2-pyridinyl)methyl]oxy}-2-pyridinyl)-2,3,4,5-tetrahydro-1H-3-benzazepine

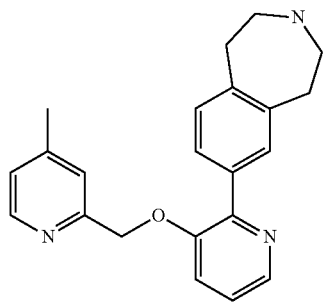 [SMILES: Cc1ccnc(COc2cccnc2-c2ccc3c(c2)CCNCC3)c1]

1,1-dimethylethyl 7-(3-{[(4-methyl-2-pyridinyl)methyl]oxy}-2-pyridinyl)-1,2,4,5-tetrahydro-3H-3-benzazepine-3-carboxylate (3.8 g) was dissolved in dioxane (20 ml). Gaseous hydrogen chloride was passed through the reaction mixture for 1.5 h. The reaction was monitored by TLC. On completion the solid formed was collected by filtration and washed with acetone. The solid was then dissolved in water and the mixture neutralised with aqueous sodium hydroxide (1M). The sticky solid formed was extracted with DCM. The organic phase was dried over sodium sulphate and concentrated in vacuo to give a solid. This was purified through silica, eluting the product with 0-12% methanol in DCM. The solid from this was triturated in diethyl ether to give the title compound, 2 g (69%) yield.

LCMS (Method A): Rt=3.25 min, [MH]+=346

NMR $^1$H NMR (400 MHz, DMSO-d6) δ ppm 8.43 ppm (1H, d, CH), 8.27 ppm (1H, d, CH), 7.77 ppm (1H, s, CH), 7.70-7.64 ppm (2H, 2×d, 2×CH), 7.35 ppm (2H, m, 2×CH), 7.20 ppm (2H, m, 2×CH), 5.23 ppm (2H, s, CH$_2$), 2.97 ppm (8H, br.m, 4×CH$_2$), 2.32 ppm (3H, s, CH$_3$)

Example 2

7-(2-(methyloxy)-6-{[(4-methyl-2-pyridinyl)methyl]oxy}phenyl)-2,3,4,5-tetrahydro-1H-3-benzazepine

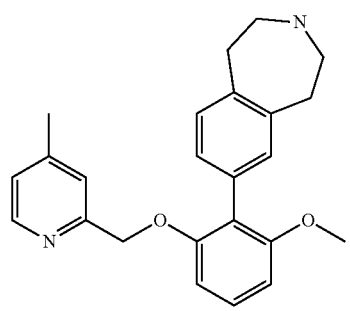 [SMILES: COc1cccc(OCc2cc(C)ccn2)c1-c1ccc2c(c1)CCNCC2]

1,1-dimethylethyl 7-(2-(methyloxy)-6-{[(4-methyl-2-pyridinyl)methyl]oxy}phenyl)-1,2,4,5-tetrahydro-3H-3-benzazepine-3-carboxylate (2.57 g) was dissolved in dioxane (20 ml). Gaseous hydrogen chloride was passed through the reaction mixture for about 1.5 h. The reaction was monitored by TLC. On completion the solid formed was collected by filtration and washed with acetone. The solid was then dissolved in water and the mixture neutralised with aqueous sodium hydroxide (1M). The sticky solid formed was extracted with DCM. The organic phase was dried over sodium sulphate and concentrated in vacuo to give a solid. This was purified by silica column chromatography eluting with 0-8% methanol in DCM. The appropriate fractions were combined and concentrated in vacuo to yield a solid. This was triturated with diethyl ether to yield the title compound, 1.34 g (67%).

LCMS (Method A): Rt=3.89 min, [MH]+=375

NMR $^1$H NMR (400 MHz, DMSO-d6) δ ppm 8.35 ppm (1H, d, CH), 7.24 ppm (1H, m, CH), 7.21-7.08 ppm (4H, m, 4×CH), 6.94 ppm (1H, br.s, CH), 6.78 ppm (2H, m, 2×CH), 5.10 ppm (2H, s, CH$_2$), 3.68 ppm (3H, s, OCH$_3$), 3.09 ppm (8H, br.m, 4×CH$_2$), 2.23 ppm (3 h, S, CH$_3$)

Example 2A

7-(2-(methyloxy)-6-{[(4-methyl-2-pyridinyl)methyl]oxy}phenyl)-2,3,4,5-tetrahydro-1H-3-benzazepine methanesulfonate 7-(2-(methyloxy)-6-{[(4-methyl-2-pyridinyl)methyl]oxy}phenyl)-2,3,4,5-tetrahydro-1H-3-benzazepine (300.0 mg; 1.0 eq) was weighed into a 20-mL vial containing a stir bar and combined with 2-propanol (6.0 mL). The suspension was heated to 40° C. and stirred for 15 min (solids dissolved). Seeds of the methanesulfonate salt were added (~1 mg). Methanesulfonic acid (3M in water; 1.1 eq.; 293.0 uL in aliquots: 43, 50, 100, and 100 µL) was added. White solid precipitated after the first aliquot (43 µL). The suspension was re-seeded with the methansulfonate salt (~1 mg). After all aliquots of the counterion solution were added, the suspension was stirred at 40° C. for 1 hr. The suspension was cooled to 5° C. at 0.5° C./min and stirred for 15 min. The product was isolated on a Büchner funnel using #1 Whatman filter paper, air-dried for 30 min, and dried at 40° C. under vacuum for 12 hrs. The title compound was produced as a white crystalline powder. A yield of 82% was obtained.

Example 3

7-(4-(methyloxy)-2-{[(4-methyl-2-pyridinyl)methyl]oxy}phenyl)-2,3,4,5-tetrahydro-1H-3-benzazepine

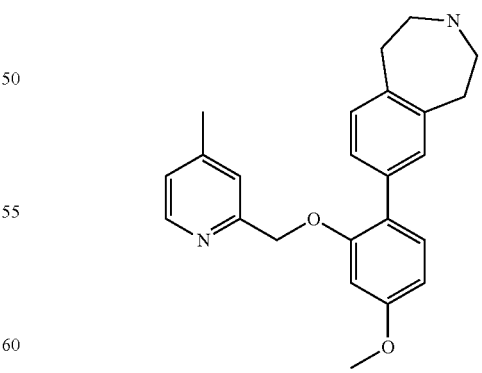

1,1-dimethylethyl 7-(4-(methyloxy)-2-{[(4-methyl-2-pyridinyl)methyl]oxy}phenyl)-1,2,4,5-tetrahydro-3H-3-benzazepine-3-carboxylate (4.8 g) was dissolved in dioxane (20 ml). Gaseous hydrogen chloride was passed through the reaction mixture for 1.5 h. The reaction was monitored by TLC.

On completion the solid formed was collected by filtration and washed with acetone. The solid was then dissolved in water and the mixture was brought to pH8 using aqueous sodium bicarbonate. The sticky solid observed was extracted with DCM. The organics were dried over sodium sulphate and concentrated in vacuo to yield a solid. This was purified by column chromatography eluting with 0-8% methanol in DCM. Appropriate fractions were combined and concentrated in vacuo to yield a solid. This was triturated in diethyl ether to yield the title compound, 1.7 g (45%).

LCMS (Method A): Rt=4.11 min, [MH]+=375

NMR $^1$H NMR (400 MHz, DMSO-d6) δ ppm 8.41 ppm (1H, d, CH), 7.38 ppm (1H, br.s, CH), 7.29-7.23 ppm (3H, m, 3×CH), 7.19-7.15 ppm (2H, m, 2×CH), 6.76 ppm (1H, br.s, CH), 6.63 ppm (1H, d, CH), 5.14 ppm (2H, s, CH$_2$), 3.79 ppm (3H, s, OCH$_3$), 3.00 ppm (8H, br.m, 4×CH$_2$), 2.30 ppm (3H, s, CH$_3$)

Example 4

1-[4-{[(4-methyl-2-pyridinyl)methyl]oxy}-3-(2,3,4,5-tetrahydro-1H-3-benzazepin-7-yl)phenyl]ethanone

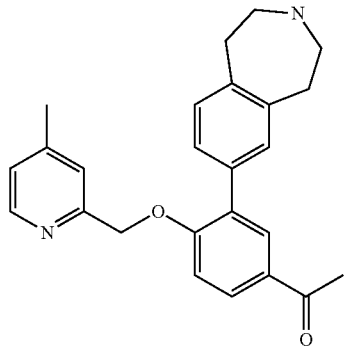 [SMILES: CC(=O)c1ccc(OCc2cc(C)ccn2)c(-c2ccc3c(c2)CCNCC3)c1]

1,1-dimethylethyl 7-(5-acetyl-2-{[(4-methyl-2-pyridinyl)methyl]oxy}phenyl)-1,2,4,5-tetrahydro-3H-3-benzazepine-3-carboxylate (3.0 g) was dissolved in dioxane (20 ml). Gaseous hydrogen chloride was passed through the reaction mixture for 1.5 h. The reaction was monitored by TLC. On completion the solid formed was collected by filtration and washed with acetone. The solid was then dissolved in water and the mixture neutralised with aqueous sodium hydroxide (1M). Solid was obtained which was collected by filtration. This was triturated with diethyl ether to yield the title compound, 2.1 g (88%).

LCMS (Method A): Rt=3.77 min, [MH]+=387

NMR $^1$H NMR (400 MHz, DMSO-d6) δ ppm 8.42 ppm (1H, d, CH), 7.98 ppm (1H, d, CH), 7.95 ppm (1H, s, CH), 7.42 ppm (1H, br.s, CH), 7.36-7.30 ppm (2H, m, 2×CH), 7.25-7.17 ppm (3H, m, 3×CH), 5.26 ppm (2H, s, CH$_2$), 2.94 ppm (8H, m, 4×CH$_2$), 2.57 ppm (3H, s, CH$_3$), 2.26 ppm (3H, s, CH$_3$)

Prepared similarly were the following examples:

| Example | Starting Material | Amount | Characterisation |
|---|---|---|---|
| 9<br>7-(6-methyl-3-{[(4-methyl-2-pyridinyl)methyl]oxy}-2-pyridinyl)-2,3,4,5-tetrahydro-1H-3-benzazepine | | 1.35 g | Mass Spec.:<br>[MH]+ = 360.1<br>HPLC:<br>Rt = 5.28 min |

Example 5

1-[4-[(2-pyrazinylmethyl)oxy]-3-(2,3,4,5-tetrahydro-1H-3-benzazepin-7-yl)phenyl]ethanone, trifluoroacetate

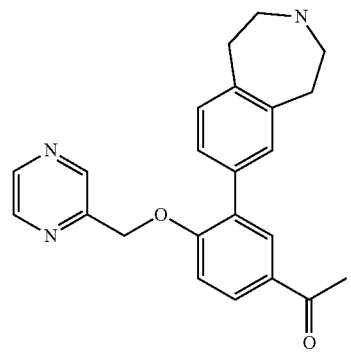 [SMILES: CC(=O)c1ccc(OCc2cnccn2)c(-c2ccc3c(c2)CCNCC3)c1]

To a stirred solution of 1,1-dimethylethyl 7-{5-acetyl-2-[(2-pyrazinylmethyl)oxy]phenyl}-1,2,4,5-tetrahydro-3H-3-benzazepine-3-carboxylate (0.093 g) in DCM (2 ml) at 0° C. was added dropwise trifluoroacetic acid (0.08 ml). This was stirred at room temperature overnight. The reaction had gone to completion by TLC and so was concentrated in vacuo and azeotroped with diethyl ether (5×10 ml). The compound obtained was washed with diethyl ether and pentane to yield a crude compound that was purified by preparative HPLC. Appropriate fractions were concentrated in vacuo to yield the title compound as the TFA salt, 0.040 g.

NMR $^1$H NMR (400 MHz, DMSO-d$_6$) δ ppm 8.88 (br. s., 2H), 8.71 (s, 1H), 8.68 (d, J=2.3 Hz, 1H), 8.62 (d, J=2.3 Hz, 1H), 8.00 (dd, J=8.6, 2.0 Hz, 1H), 7.89 (d, J=2.3 Hz, 1H), 7.49 (s, 1H), 7.45 (d, J=7.8 Hz, 1H), 7.38 (d, J=8.8 Hz, 1H), 7.29 (d, J=7.8 Hz, 1H), 5.41 (s, 2H), 3.19-3.27 (m, 4H), 3.04-3.17 (m, 4H), 2.58 (s, 3H)

Mass Spec.: [MH]+=374.1

Example 6

7-(5-fluoro-2-{[(4-methyl-2-pyridinyl)methyl]oxy}phenyl)-1,2,3,4-tetrahydroisoquinoline

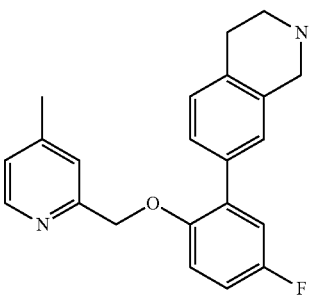 [SMILES: Cc1ccnc(COc2ccc(F)cc2-c2ccc3c(c2)CNCC3)c1]

1,1-Dimethylethyl 7-(5-fluoro-2-{[(4-methyl-2-pyridinyl)methyl]oxy}phenyl)-3,4-dihydro-2(1H)-isoquinolinecarboxylate (0.169 g) was dissolved in dioxane (1 ml). This was ice cooled before adding dropwise a solution of hydrogen chloride in dioxane (2 ml). This was stirred at room temperature overnight before concentrating in vacuo. The residue obtained was dissolved in water and backwashed with ethyl acetate. The aqueous layer was neutralised with aqueous sodium hydroxide (1M) and extracted with ethyl acetate. The organics were concentrated in vacuo and purified by preparative HPLC. Appropriate fractions were concentrated, neutralised with aqueous sodium bicarbonate and extracted with ethyl acetate. The organics were concentrated in vacuo to yield the title compound, 0.061 g (47%).

LCMS (Method A): Rt=6.37 min, [MH]+=349

Prepared similarly were the following examples:

| Example | Starting Material | Amount | LCMS |
|---|---|---|---|
| 10 | 7-(5-methyl-2-{[(4-methyl-2-pyridinyl)methyl]oxy}phenyl)-1,2,3,4-tetrahydroisoquinoline | 72 mg | LCMS (Method B): Rt = 6.61 min, [MH]+ = 345 |
| 11 | 7-(2-(methyloxy)-6-{[(4-methyl-2-pyridinyl)methyl]oxy}phenyl)-1,2,3,4-tetrahydroisoquinoline | 46 mg | LCMS (Method B): Rt = 6.06 min, [MH]+ = 361.1 |
| 12 | 7-(5-(ethyloxy)-2-{[(4-methyl-2-pyridinyl)methyl]oxy}phenyl)-1,2,3,4-tetrahydroisoquinoline | 50 mg | LCMS (Method A): Rt = 6.59 min, [MH]+ = 375 |

-continued

| Example | Starting Material | Amount | LCMS |
|---|---|---|---|
| 14<br>4-{[(4-methyl-2-pyridinyl)methyl]-oxy}-3-(1,2,3,4-tetrahydro-7-isoquinolinyl)-benzonitrile | | 50 mg | LCMS (Method A):<br>Rt = 5.94 min,<br>[MH]+ = 356 |
| 15<br>7-[2-{[(4-methyl-2-pyridinyl)methyl]-oxy}-5-(trifluoromethyl)-phenyl]-1,2,3,4-tetrahydroisoquinoline | | 84 mg | LCMS (Method B):<br>Rt = 6.72 min,<br>[MH]+ = 399.1 |
| 16<br>7-(5-(methyloxy)-2-{[(4-methyl-2-pyridinyl)methyl]-oxy}phenyl)-1,2,3,4-tetrahydroisoquinoline | | 84 mg | LCMS (Method A):<br>Rt = 6.18 min,<br>[MH]+ = 361.1 |
| 17<br>7-(5-(1,1-dimethylethyl)-2-{[(4-methyl-2-pyridinyl)methyl]-oxy}phenyl)-1,2,3,4-tetrahydroisoquinoline | | 45 mg | LCMS (Method B):<br>Rt = 7.10 min,<br>[MH]+ = 387.2 |

| Example | Starting Material | Amount | LCMS |
|---|---|---|---|
| 39 N-methyl-4-{[(4-methyl-2-pyridinyl)methyl]-oxy}-3-(2,3,4,5-tetrahydro-1H-3-benzazepin-7-yl)benzamide | | 0.065 g | LCMS (Method A): Rt = 5.38 min, [MH]+ = 402 |
| 40 4-{[(4-methyl-2-pyridinyl)methyl]-oxy}-3-(2,3,4,5-tetrahydro-1H-3-benzazepin-7-yl)benzamide | | 0.1 g | LCMS (Method B): Rt = 5.21 min, [MH]+ = 388 |
| 41 N,N-dimethyl-4-{[(4-methyl-2-pyridinyl)methyl]-oxy}-3-(1,2,3,4-tetrahydro-7-isoquinolinyl)-benzamide | | 0.06 g | LCMS (Method A): Rt = 5.43 min, [MH]+ = 402 |

-continued

| Example | Starting Material | Amount | LCMS |
|---|---|---|---|
| 42<br>4-{[(4-methyl-2-pyridinyl)methyl]-oxy}-3-(1,2,3,4-tetrahydro-7-isoquinolinyl)-benzamide | | 0.06 g | LCMS (Method A):<br>Rt = 3.01 min,<br>[MH]+ = 374 |
| 43<br>7-(2,3-bis(methyloxy)-6-{[(4-methyl-2-pyridinyl)methyl]-oxy}phenyl)-1,2,3,4-tetrahydroisoquinoline | | 0.100 g | LCMS (Method A):<br>Rt = 3.49 min,<br>[MH]+ = 391 |
| 44<br>7-(2,3-bis(methyloxy)-6-{[(4-methyl-2-pyridinyl)methyl]-oxy}phenyl)-2,3,4,5-tetrahydro-1H-3-benzazepine | | 0.07 g | LCMS (Method A):<br>Rt = 3.56 min,<br>[MH]+ = 405 |

Example 7

7-[2-({[4-(methyloxy)-2-pyridinyl]methyl}oxy)phenyl]-2,3,4,5-tetrahydro-1H-3-benzazepine

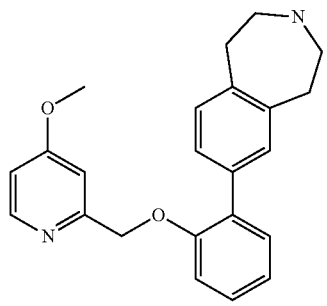 [SMILES: COc1ccnc(COc2ccccc2-c2ccc3c(c2)CCNCC3)c1]

To a stirred solution of 1,1-dimethylethyl 7-[2-({[4-(methyloxy)-2-pyridinyl]methyl}oxy)phenyl]-1,2,4,5-tetrahydro-3H-3-benzazepine-3-carboxylate (3.0 g) in dioxane (30 ml) was added hydrogen chloride gas for 2 h at 10-20° C. This was concentrated in vacuo. The residue was dissolved in water, washed with ethyl acetate and basified by adding aqueous sodium bicarbonate. This was extracted with 10% methanol in DCM. The organics were dried over sodium sulphate and concentrated in vacuo to yield the title compound, 2.14 g (91%).

LCMS (Method B): Rt=6.18 min, [MH]+=361

Example 8

1-[4-[(2-pyridinylmethyl)oxy]-3-(2,3,4,5-tetrahydro-1H-3-benzazepin-7-yl)phenyl]ethanone, trifluoroacetate

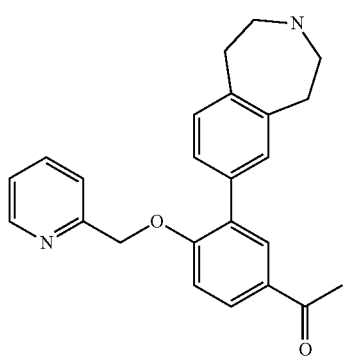 [SMILES: CC(=O)c1ccc(OCc2ccccn2)c(-c2ccc3c(c2)CCNCC3)c1]

To a cooled, stirred solution of 1,1-dimethylethyl 7-{5-acetyl-2-[(2-pyridinylmethyl)oxy]phenyl}-1,2,4,5-tetrahydro-3H-3-benzazepine-3-carboxylate (0.056 g) in DCM (1 ml) was added TFA (0.2 ml). This was stirred overnight. The reaction had gone to completion and so was concentrated in vacuo and tritutrated with pentane/ether to yield the title compound as the TFA salt, 0.028 g (63.6%).

Mass Spec.: [MH]+=373.1
HPLC: Rt=5.71 min.
Prepared similarly were the following examples:

| Example | Starting Material | Amount | Characterisation |
|---|---|---|---|
| 18<br>7-{6-methyl-3-[(2-pyrazinylmethyl)-oxy]-2-pyridinyl}-2,3,4,5-tetrahydro-1H-3-benzazepine, trifluoroacetate | | 100 mg | HPLC<br>Rt = 5.51 min<br>Mass Spec:<br>[MH]+ = 347.1 |
| 19<br>7-(6-methyl-3-{[(4-methyl-2-pyridinyl)methyl]-oxy}-2-pyridinyl)-2,3,4,5-tetrahydro-1H-3-benzazepine, trifluoroacetate | | 22 mg | HPLC<br>Rt = 5.23 min<br>Mass Spec:<br>[MH]+ = 360.1 |

-continued

| Example | Starting Material | Amount | Characterisation |
|---|---|---|---|
| 20<br>7-{5-(methyloxy)-2-[(2-pyrazinylmethyl)oxy]phenyl}-2,3,4,5-tetrahydro-1H-3-benzazepine, trifluoroacetate | | 80 mg | HPLC<br>Rt = 8.00 min<br>Mass Spec:<br>[MH]+ = 362.1 |
| 21<br>7-[5-(methyloxy)-2-({[4-(methyloxy)-2-pyridinyl]methyl}oxy)phenyl]-2,3,4,5-tetrahydro-1H-3-benzazepine | | 150 mg<br>(after prep HPLC) | HPLC<br>Rt = 6.88 min<br>Mass Spec:<br>[MH]+ = 391.1 |
| 22<br>7-(5-(methyloxy)-2-{[(4-methyl-2-pyridinyl)methyl]oxy}phenyl)-2,3,4,5-tetrahydro-1H-3-benzazepine, trifluoroacetate (TFA salt of example 29) | | 75 mg | HPLC<br>Rt = 6.89 min<br>Mass Spec:<br>[MH]+ = 375.1 |
| 23<br>1-[4-({[4-(methyloxy)-2-pyridinyl]methyl}oxy)-3-(2,3,4,5-tetrahydro-1H-3-benzazepin-7-yl)phenyl]ethanone | | 120 mg<br>(after prep HPLC) | HPLC<br>Rt = 6.55 min<br>Mass Spec:<br>[MH]+ = 403.2 |

| Example | Starting Material | Amount | Characterisation |
|---|---|---|---|
| 24<br>1-[4-{[(4-methyl-2-pyridinyl)-methyl]oxy}-3-(2,3,4,5-tetrahydro-1H-3-benzazepin-7-yl)phenyl]ethanone, trifluoroacetate (TFA salt of example 4) | | 26 mg | HPLC<br>Rt = 5.65 min<br>Mass Spec:<br>[MH]+ = 387.1 |
| 25<br>7-[2-({[4-(methyloxy)-2-pyridinyl]methyl}-oxy)phenyl]-2,3,4,5-tetrahydro-1H-3-benzazepine, trifluoroacetate | | 0.908 g | HPLC<br>Rt = 5.92 min<br>Mass Spec:<br>[MH]+ = 361.1 |
| 47<br>7-[6-methyl-3-({[4-(methyloxy)-2-pyridinyl]methyl}-oxy)-2-pyridinyl]-2,3,4,5-tetrahydro-1H-3-benzazepine | | 0.118 g (after prep HPLC) | HPLC<br>Rt = 4.35 min<br>Mass Spec:<br>[MH]+ = 376.1 |

Example 26

7-(5-fluoro-2-{[(4-methyl-2-pyridinyl)methyl]oxy}phenyl)-2,3,4,5-tetrahydro-1H-3-benzazepine

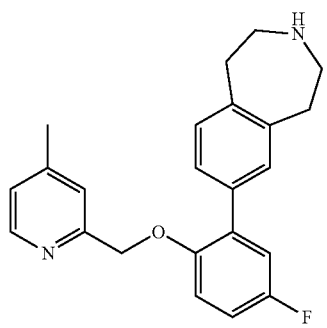 [SMILES: Cc1ccnc(COc2ccc(F)cc2-c2ccc3c(c2)CCNCC3)c1]

1,1-dimethylethyl 7-(5-fluoro-2-{[(4-methyl-2-pyridinyl)methyl]oxy}phenyl)-1,2,4,5-tetrahydro-3H-3-benzazepine-3-carboxylate, (0.304 g) was dissolved in a minimum amount of dioxane. The solution was cooled in ice and to this was added a solution of HCl in dioxane (2 ml). This was stirred until the reaction had gone to completion by tlc. The reaction mixture was concentrated in vacuo. The product salt was dissolved in water and backwashed with ethyl acetate. The aqueous was neutralised with aqueous sodium hydroxide (1M). This was extracted with ethyl acetate. The organics were dried over sodium sulphate and concentrated to give the title compound, 100 mg.

LCMS (Method B): Rt=6.34 min, [MH]+=363.1

Prepared similarly were the following examples:

| Example | Starting Material | Amount | LCMS |
|---|---|---|---|
| 27 | 7-(5-methyl-2-{[(4-methyl-2-pyridinyl)methyl]-oxy}phenyl)-2,3,4,5-tetrahydro-1H-3-benzazepine | 56 mg | LCMS (Method B): Rt = 6.67 min, [MH]+ = 359.2 |
| 28 | 7-(5-(ethyloxy)-2-{[(4-methyl-2-pyridinyl)methyl]-oxy}phenyl)-2,3,4,5-tetrahydro-1H-3-benzazepine | 158 mg | LCMS (Method A): Rt = 6.59 min, [MH]+ = 389.2 |
| 29 | 7-(5-(methyloxy)-2-{[(4-methyl-2-pyridinyl)methyl]-oxy}phenyl)-2,3,4,5-tetrahydro-1H-3-benzazepine | 65 mg | LCMS (Method A): Rt = 6.22 min, [MH]+ = 375.1 |
| 30 | 4-{[(4-methyl-2-pyridinyl)methyl]-oxy}-3-(2,3,4,5-tetrahydro-1H-3-benzazepin-7-yl)benzonitrile | 70 mg | LCMS (Method A): Rt = 5.82 min, [MH]+ = 370.1 |

-continued

| Example | Starting Material | Amount | LCMS |
|---|---|---|---|
| 31<br>7-[2-{[(4-methyl-2-pyridinyl)-methyl]oxy}-5-(trifluoromethyl)phenyl]-2,3,4,5-tetrahydro-1H-3-benzazepine | | 70 mg | LCMS (Method A):<br>Rt = 6.67 min,<br>[MH]+ = 413.1 |
| 32<br>7-(5-(1,1-dimethylethyl)-2-{[(4-methyl-2-pyridinyl)methyl]-oxy}phenyl)-2,3,4,5-tetrahydro-1H-3-benzazepine | | 144 mg | LCMS (Method B):<br>Rt = 7.08 min,<br>[MH]+ = 401.2 |
| 45<br>7-(5-chloro-2-{[(4-methyl-2-pyridinyl)methyl]-oxy}phenyl)-2,3,4,5-tetrahydro-1H-3-benzazepine | | 0.16 g | LCMS (Method B):<br>Rt = 6.71 min,<br>[MH]+ = 379 |

Example 33

7-(3-{[(4-ethyl-2-pyridinyl)methyl]oxy}-6-methyl-2-pyridinyl)-2,3,4,5-tetrahydro-1H-3-benzazepine

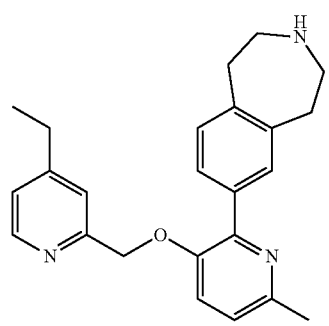 [SMILES: CCc1ccnc(COc2ccc(C)nc2-c2ccc3c(c2)CCNCC3)c1]

To a stirred solution of 1,1-dimethylethyl 7-(3-{[(4-ethyl-2-pyridinyl)methyl]oxy}-6-methyl-2-pyridinyl)-1,2,4,5-tetrahydro-3H-3-benzazepine-3-carboxylate, (4.3 g) in dioxane (30 ml) was passed through HCl (gas) for 30 min at 20° C. After completion of reaction by TLC, the solvent was removed in vacuo. The solid obtained was washed with acetone and dissolved in water. This was neutralised with sodium bicarbonate, extracted with DCM and concentrated in vacuo to give a crude product. This was purified through silica using 6% methanol in DCM. Appropriate fractions were combined and concentrated in vacuo to give a product. This was triturated in diethyl ether to yield the title compound, 1.5 g.

LCMS (Method B): Rt=3.29 min, [MH]+=374

The following example was prepared similarly:

Example 35

1-[4-{[(4-ethyl-2-pyridinyl)methyl]oxy}-3-(2,3,4,5-tetrahydro-1H-3-benzazepin-7-yl)phenyl]ethanone

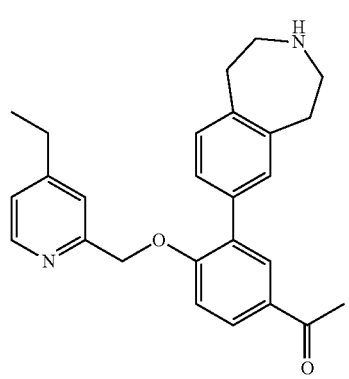 [SMILES: CCc1ccnc(COc2ccc(C(C)=O)cc2-c2ccc3c(c2)CCNCC3)c1]

To a solution of 1,1-dimethylethyl 7-(5-acetyl-2-{[(4-ethyl-2-pyridinyl)methyl]oxy}phenyl)-1,2,4,5-tetrahydro-3H-3-benzazepine-3-carboxylate, (0.217 g) in DCM (3 ml) was added TFA (0.4 ml). This was stirred at room temperature. After completion of reaction by tlc, the reaction mixture was concentrated in vacuo and purified by preparative hplc. Product fractions were concentrated in vacuo and the product obtained was partitioned between DCM and aqueous sodium bicarbonate. The organics were dried over sodium sulphate and concentrated in vacuo to yield the title compound, 0.035 g LCMS (Method A): Rt=5.28 min, [MH]+=401.05
HPLC: 6.89 min.

| Example | Starting Material | Amount | LCMS |
|---|---|---|---|
| 34<br>7-(6-(1,1-dimethylethyl)-3-{[(4-methyl-2-pyridinyl)methyl]oxy}-2-pyridinyl)-2,3,4,5-tetrahydro-1H-3-benzazepine | | 2.7 g | LCMS (Method B):<br>Rt = 4.73 min,<br>[MH]+ = 402 |

Example 36

1-[4-({[4-(ethyloxy)-2-pyridinyl]methyl}oxy)-3-(2,3,4,5-tetrahydro-1H-3-benzazepin-7-yl)phenyl]ethanone

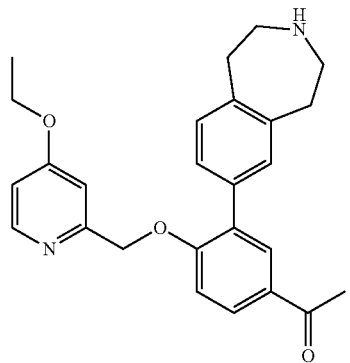 [SMILES: CCOc1ccnc(COc2ccc(C(C)=O)cc2-c2ccc3c(c2)CCNCC3)c1]

To a stirred solution of 1,1-dimethylethyl 7-[5-acetyl-2-({[4-(ethyloxy)-2-pyridinyl]methyl}oxy)phenyl]-1,2,4,5-tetrahydro-3H-3-benzazepine-3-carboxylate, (0.16 g) in DCM (2 ml) at 0 C. was added TFA (0.247 g). This was stirred at room temperature for 16 h before concentrating and purifying by preparative hplc. The title compound was isolated as the TFA salt, 0.058 g Mass Spec: [MH]+=417.2
HPLC: 6.81 min.
Similarly prepared was example 50:

(3-{[(1,1-dimethylethyl)oxy]carbonyl}-2,3,4,5-tetrahydro-1H-3-benzazepin-7-yl)boronic acid (Preparation in WO2004056369) (0.125 g) was added to a stirred solution of R19158/5/TC-1,2-({[2-bromo-4-(methyloxy)phenyl]oxy}methyl)pyridine, (0.085 g) in DME (2 ml) under an argon atmosphere at room temperature. After 1 min, aqueous sodium carbonate (2M, 3 mole equiv.) was added. After 2 min, tetrakis (0.016 g) was added and this was heated at 90 C until completion of the reaction by tlc. The crude product was partitioned between DCM and water. The aqueous was reextracted twice with DCM. The combined organics were dried over sodium sulphate, filtered and concentrated in vacuo to yield a crude product. This was purified by column chromatography (silica) using a gradient of ethyl acetate in cyclohexane to yield the BOC-protected product. This was stirred in a solution of HCl in ethyl acetate until reaction had gone to completion by tlc. This yielded the title compound as the hydrochloride salt, 0.03 g.

Mass Spec: [MH]+=361.1
HPLC: 6.06 min.

| Example | Starting Material | Amount | Characterisation |
|---|---|---|---|
| 50<br>1-[4-{[(4-{[2-(methyloxy)ethyl]oxy}-2-pyridinyl)methyl]oxy}-3-(2,3,4,5-tetrahydro-1H-3-benzazepin-7-yl)phenyl]-ethanone | 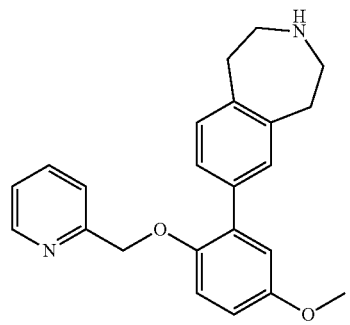 [SMILES: COc1ccc(OCc2ccccn2)c(-c2ccc3c(c2)CCNCC3)c1] | 0.045 g | HPLC<br>Rt = 6.66 min<br>Mass Spec:<br>[MH]+ = 447 |

Example 37

7-{5-(methyloxy)-2-[(2-pyridinylmethyl)oxy]phenyl}-2,3,4,5-tetrahydro-1H-3-benzazepine

Example 38

1-[4-[(2-pyridinylmethyl)oxy]-3-(1,2,3,4-tetrahydro-7-isoquinolinyl)phenyl]ethanone

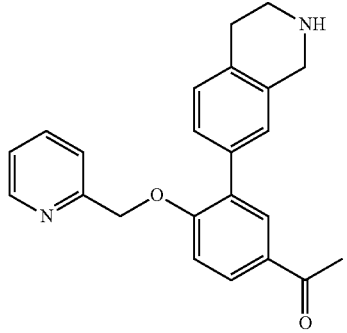 [SMILES: CC(=O)c1ccc(OCc2ccccn2)c(-c2ccc3c(c2)CNCC3)c1]

To a solution of 1,1-dimethylethyl 7-{5-acetyl-2-[(2-pyridinylmethyl)oxy]phenyl}-3,4-dihydro-2(1H)-isoquinolinecarboxylate (0.21 g) in dioxane was added a solution of HCl in dioxane (5 ml). The reaction mixture was stirred at room temperature until it was complete (by TLC). It was concentrated in vacuo and the residue was purified by preparative hplc to yield the title compound as the TFA salt, 0.055 g.

Mass Spec: [MH]+=359.1
HPLC: 6.59 min.

Example 46

7-{5-chloro-2-[(2-pyridinylmethyl)oxy]phenyl}-1,2,3,4-tetrahydroisoquinoline

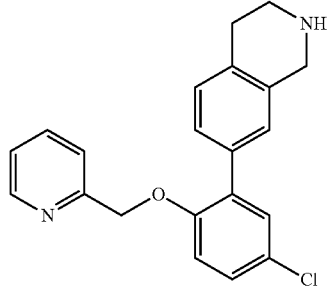 [SMILES: Clc1ccc(OCc2ccccn2)c(-c2ccc3c(c2)CNCC3)c1]

To an ice cooled solution of, 1,1-dimethylethyl 7-(5-chloro-2-{[(4-methyl-2-pyridinyl)methyl]oxy}phenyl)-3,4-dihydro-2(1H)-isoquinolinecarboxylate, (0.28 g) in DCM (1 ml) was added TFA (1 ml) and this was stirred at room temperature overnight. The reaction mixture was dissolved in water and backwashed with ethyl acetate. The aqueous layer was neutralised with aqueous sodium bicarbonate and extracted with ethyl acetate. The organics were dried over sodium sulphate and concentrated in vacuo to yield the title compound, 0.12 g LCMS (Method A): Rt=6.66 min, [MH]+=365

Example 48

7-(6-chloro-3-{[(4-methyl-2-pyridinyl)methyl]oxy}-2-pyridinyl)-2,3,4,5-tetrahydro-1H-3-benzazepine

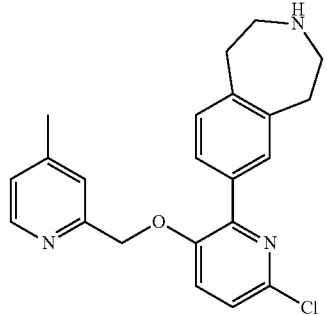 [SMILES: Cc1ccnc(COc2ccc(Cl)nc2-c2ccc3c(c2)CCNCC3)c1]

To an ice cooled solution of 1,1-dimethylethyl 7-(6-chloro-3-{[(4-methyl-2-pyridinyl)methyl]oxy}-2-pyridinyl)-1,2,4,5-tetrahydro-3H-3-benzazepine-3-carboxylate in DCM (1 ml) was added dropwise TFA (1 ml) and the reaction mixture stirred at room temperature until the starting material had been consumed. The reaction mixture was concentrated in vacuo, dissolved in water and backwashed with ethyl acetate. The aqueous layer was neutralised with aqueous sodium bicarbonate then extracted with ethyl acetate, dried over sodium sulphate and concentrated in vacuo to yield the title compound, 27 mg.

LCMS (Method A): Rt=6.33 min, [MH]+=380.1
Prepared similarly were the following examples:

| Example | Starting Material | Amount | Characterisation |
|---|---|---|---|
| 49<br>7-(6-chloro-3-{[(4-methyl-2-pyridinyl)methyl]oxy}-2-pyridinyl)-1,2,3,4-tetrahydroisoquinoline | | 0.027 g | LCMS (Method B):<br>Rt = 6.30 min,<br>[MH]+ = 366.1 |
| 51<br>1-{3-(2,3-dihydro-1H-isoindol-5-yl)-4-[(2-pyridinylmethyl)oxy]phenyl}ethanone | | 0.035 g | HPLC<br>Rt = 5.46 min<br>Mass Spec:<br>[MH]+ = |

| Example | Starting Material | Amount | Characterisation |
|---|---|---|---|
| 52 1-[4-[(2-pyridinylmethyl)-oxy]-3-(1,2,3,4-tetrahydro-6-isoquinolinyl)-phenyl]ethanone | 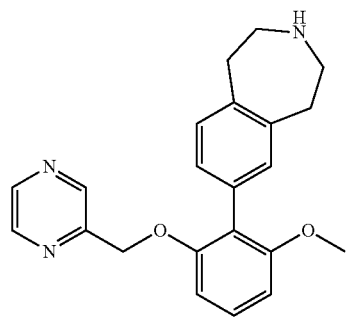 [SMILES: COc1cccc(OCc2cnccn2)c1-c1ccc2c(c1)CCNCC2] | 0.063 g | HPLC Rt = 5.57 min Mass Spec: [MH]+ = 359.1 |

Example 13

7-{2-(methyloxy)-6-[(2-pyrazinylmethyl)oxy]phenyl}-2,3,4,5-tetrahydro-1H-3-benzazepine, hydrochloride To a solution of 1,1-dimethylethyl 7-{2'-(methyloxy)-6'-[(2-pyrazinylmethyl)oxy]-4-biphenylyl}-1,2,4,5-tetrahydro-3H-3-benzazepine-3-carboxylate (1.0 g) in DCM was bubbled dry HCl gas for 2 hours. The solvent was removed under reduced pressure and the residue was washed with diethyl ether. The precipitated solid was collected by filtration to give the title compound, 0.700 g LCMS (Method C): Rt=1.49 min, [MH]+=362.2

Preparation of Polymorphic forms of 7-(2-(methyloxy)-6-{[(4-methyl-2-pyridinyl)methyl]oxy}phenyl)-2,3,4,5-tetrahydro-1H-3-benzazepine Form 1

The crystalline form of 7-(2-(methyloxy)-6-{[(4-methyl-2-pyridinyl)methyl]oxy}phenyl)-2,3,4,5-tetrahydro-1H-3-benzazepine was produced by a scale up 8 g of the method used to produce the compound of Example 2A. It was characterised by one or more of the methods described below and was designated as Form 1.

Preparation of Form 2 Batch 1

40.0 mg of the Form 1 was combined with 1 mL of LC-grade water, mixed and temperature-cycled from 40° C. to 5° C. for 72 hours, then equilibrated at 20° C. for 1 hour. The solids were isolated from the filtrate by vacuum-filtration on a stainless steel analytical plate with 10"-15" vacuum at RT for ~30 minutes.

Preparation of Form 2 Batch 2

237 mg of the input material was combined with 4 mL of HPLC-grade water. The slurry was seeded and thermocycled from 40° C. to 5° C. over 20 hours. Raman assay of a filtered aliquot showed Form 2. Solids were filtered by vacuum and dried in a vacuum oven at 20" vacuum and 40° C. for 4 hours. Yield=197.6 mg. 150 mg of Form 1 was combined with 3 mL of HPLC-grade water and stirred at RT (~23° C.) for 18 hours. A small aliquot was withdrawn, filtered, and assayed by Raman. The spectrum was consistent with Form 1. The slurry was seeded with Form 1 and stirred at 40° C. for 4 hours. Raman assay of a filtered aliquot showed a mixture of Form 1 and Form 2 with approximately 30% Form 2. The slurry was thermocycled from 40° C. to 5° C. over 72 hours. Raman assay of a filtered aliquot showed only Form 2. The rest of the slurry was filtered. Raman assay of the isolated solid showed only Form 2. The filtered sample was dried at 30° C. with 20" vacuum for 3.5 hours. Raman assay showed only Form 1 consistent with batch 1. Dried yield=95 mg.

Characterisation Methods

Powder X-ray diffractograms were acquired using either a PANalytical X'Pert Pro diffractometer on Si zero-background wafers. All diffractograms were collected using a monochromatic Cu Kα (45 kV/40 mA) radiation and a step size of 0.02°2θ. Peak positions were determined using Highscore software and the margin of error in peak positions is approximately ±0.1°2θ.

FIG. 1 shows the XRPD diffraction pattern for FORM 1. Table 1 shows the main degrees 2 theta peaks observed for FORM 1.

FIG. 4 shows the XRPD diffraction pattern for FORM 2. Table 2 shows the main degrees 2 theta peaks observed for FORM 2.

Table 3 shows the distinguishing features between the XRPD diffraction pattern for FORM 1 and FORM 2.

TABLE 1

| XRPD peak positions for Form 1 | |
|---|---|
| Position/°2θ | d-spacing/Å |
| 11.7 | 7.5 |
| 12.7 | 7.0 |
| 13.7 | 6.5 |

TABLE 1-continued

XRPD peak positions for Form 1

| Position/°2θ | d-spacing/Å |
|---|---|
| 14.6 | 6.1 |
| 16.0 | 5.5 |
| 17.8 | 5.0 |
| 18.9 | 4.7 |
| 19.4 | 4.6 |
| 20.2 | 4.4 |
| 21.2 | 4.2 |
| 22.6 | 3.9 |
| 23.0 | 3.9 |
| 23.7 | 3.8 |
| 24.0 | 3.7 |
| 24.4 | 3.6 |
| 25.1 | 3.5 |
| 25.5 | 3.5 |
| 26.1 | 3.4 |
| 26.9 | 3.3 |
| 27.5 | 3.2 |
| 28.1 | 3.2 |

TABLE 2

XRPD peak positions for Form 2

| Position/°2θ | d-spacing/Å |
|---|---|
| 8.9 | 9.9 |
| 9.9 | 9.0 |
| 13.3 | 6.6 |
| 14.6 | 6.1 |
| 14.8 | 6.0 |
| 15.2 | 5.8 |
| 16.5 | 5.4 |
| 16.7 | 5.3 |
| 17.9 | 4.9 |
| 18.9 | 4.7 |
| 19.1 | 4.6 |
| 21.3 | 4.2 |
| 22.9 | 3.9 |
| 23.1 | 3.8 |
| 23.4 | 3.8 |
| 23.8 | 3.7 |
| 24.3 | 3.7 |
| 25.1 | 3.6 |
| 25.6 | 3.5 |
| 26.5 | 3.4 |
| 26.9 | 3.3 |
| 27.6 | 3.2 |

TABLE 3

XRPD peak d-spacing/Å

| Form 1 | Form 2 |
|---|---|
| 11.7 | 8.9 |
| 12.7 | 9.9 |
| 13.7 | 13.3 |
| 16.0 | 15.2 |
|  | 16.7 |

FT-Raman Spectroscopy

Raman spectra were collected with a Nicolet NXR9650 (Thermo Electron) equipped with 1064 nm Nd:YVO4 excitation laser, InGaAs and liquid-N2 cooled Ge detectors, and a MicroStage. All spectra were acquired at 4 cm$^{-1}$ resolution, 64-128 scans, using Happ-Genzel apodization function and 2-level zero-filling. Band positions were determined using Omnic software and the margin of error in band positions is approximately ±1 cm$^{-1}$.

FIG. 2 shows the FT-Raman Spectrum for FORM 1. Table 4 shows the main peaks observed for FORM 1.

FIG. 5 shows the FT-Ramen Spectrum for FORM 2. Table 5 shows the main peaks observed for FORM 2.

Table 6 shows the distinguishing features between the Raman Spectra for FORM 1 and FORM 2.

TABLE 4

Raman band positions for Form 1
Position/cm$^{-1}$

| |
|---|
| 202 |
| 226 |
| 250 |
| 312 |
| 354 |
| 462 |
| 521 |
| 532 |
| 541 |
| 551 |
| 562 |
| 570 |
| 609 |
| 715 |
| 766 |
| 784 |
| 851 |
| 994 |
| 1018 |
| 1041 |
| 1103 |
| 1177 |
| 1189 |
| 1208 |
| 1236 |
| 1276 |
| 1295 |
| 1363 |
| 1415 |
| 1448 |
| 1464 |
| 1569 |
| 1610 |
| 2832 |
| 2865 |
| 2912 |
| 2945 |
| 2958 |
| 3059 |

TABLE 5

Raman band positions for Form 2
Position/cm$^{-1}$

| |
|---|
| 207 |
| 243 |
| 254 |
| 316 |
| 337 |
| 388 |
| 442 |
| 463 |
| 537 |
| 554 |
| 572 |
| 614 |
| 715 |
| 736 |
| 748 |
| 777 |
| 856 |
| 964 |
| 1005 |
| 1022 |
| 1037 |

TABLE 5-continued

Raman band positions for Form 2
Position/cm$^{-1}$ 1107
1193
1210
1242
1289
1371
1422
1475
1571
1614
2787
2921
2934
2957
2973
2990
3014
3022
3043
3062
3084

TABLE 6

Raman band position/cm$^{-1}$

| Form 1 | Form 2 |
|---|---|
| 2945 | 2934 |
| 2832 | 1614 |
| 1610 | 1371 |
| 1363 | 1005 |
| 994 | 777 |
| 784 | |

Differential Scanning calorimetry (DSC)

Differential scanning calorimetry was conducted with a TAInstruments Q100 differential scanning calorimeter equipped with an autosampler and a refrigerated cooling system under 40 mL/min N$_2$ purge. DSC thermograms were obtained at 15° C./min in crimped Al pans.

FIG. 3 shows the DSC thermogram of FORM 1.
FIG. 6 shows DSC thermogram of FORM 2.

The invention claimed is:
1. A compound which is:

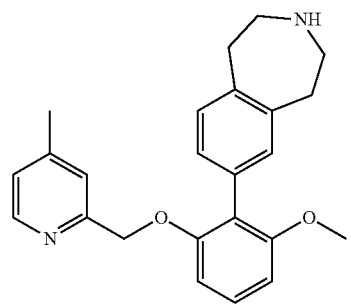 [SMILES: COc1cccc(OCc2cc(C)ccn2)c1-c1ccc2c(c1)CCNCC2]

7-(2-(methyloxy)-6-{[(4-methyl-2-pyridinyl)methyl]oxyl phenyl)-2,3,4,5-tetrahydro-1H-3-benzazepine;
or a salt thereof.

2. The compound or salt according to claim 1, wherein the salt is a pharmaceutically acceptable salt.

3. The compound or salt according to claim 1, wherein the salt is mesylate.

4. A pharmaceutical composition which comprises the compound or pharmaceutically acceptable salt as defined in claim 2, and a pharmaceutically acceptable carrier, diluent or excipient.

5. The pharmaceutical composition according to claim 4, wherein the composition is adapted for topical dermal administration.

6. A method of treating an autoimmune condition selected from systemic lupus erythematosus, discoid lupus, Sjorgens syndrome, Wegners granulomatosis and other vasculitides, bullous pemphigoid and pemphigus, idiopathic thrombocytopenic purpura, giant cell arteriosis, chronic idiopathic urticaria with and without auto-antibody status, glomerulonephritis, chronic transplant rejection and rheumatoid arthritis, wherein the method comprises administering to a human subject in need thereof a therapeutically effective amount of the compound or pharmaceutically acceptable salt as defined in claim 2.

7. The method of treatment according to claim 6, wherein the autoimmune condition is chronic idiopathic urticaria with and without auto-antibody status.

8. The method of treatment according to claim 6, wherein the autoimmune condition is discoid lupus.

9. The compound according to claim 1, which is:

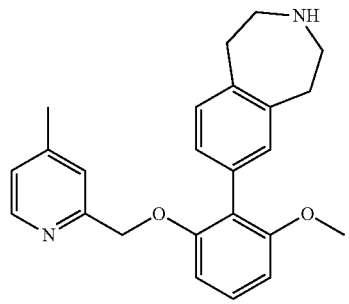 [SMILES: COc1cccc(OCc2cc(C)ccn2)c1-c1ccc2c(c1)CCNCC2]

7-(2-(methyloxy)-6-{[(4-methyl-2-pyridinyl)methyl] oxy}phenyl)-2,3,4,5-tetrahydro-1H-3-benzazepine.

10. A pharmaceutical composition which comprises the mesylate salt as defined in claim 3, and a pharmaceutically acceptable carrier, diluent or excipient.

11. The pharmaceutical composition according to claim 10, wherein the composition is adapted for topical dermal administration.

12. A method of treating an autoimmune condition selected from systemic lupus erythematosus, discoid lupus, Sjorgens syndrome, Wegners granulomatosis and other vasculitides, bullous pemphigoid and pemphigus, idiopathic thrombocytopenic purpura, giant cell arteriosis, chronic idiopathic urticaria with and without auto-antibody status, glomerulonephritis, chronic transplant rejection and rheumatoid arthritis, wherein the method comprises administering to a human subject in need thereof a daily dose of between 1 µg and 2 g of the compound or pharmaceutically acceptable salt as defined in claim 2.

13. The method of treatment according to claim 12, wherein the autoimmune condition is chronic idiopathic urticaria with and without auto-antibody status.

14. The method of treatment according to claim 12, wherein the autoimmune condition is discoid lupus.

* * * * *